(12) United States Patent
Ishibashi et al.

(10) Patent No.: US 6,280,402 B1
(45) Date of Patent: Aug. 28, 2001

(54) ULTRASOUND THERAPEUTIC APPARATUS

(75) Inventors: Yoshiharu Ishibashi, Tokyo; Katsuhiko Fujimoto, Urawa; Mariko Shibata, Yokohama; Takuji Suzuki, Kawasaki; Satoshi Aida, Tokyo, all of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/335,914

(22) Filed: Jun. 18, 1999

Related U.S. Application Data

(62) Division of application No. 08/624,104, filed on Mar. 29, 1996, now Pat. No. 5,984,881.

(30) Foreign Application Priority Data

Mar. 31, 1995 (JP) .................................. 7/097474
Aug. 9, 1995 (JP) .................................. 7-203576

(51) Int. Cl.⁷ ............................................ A61B 8/00
(52) U.S. Cl. ............................................ 601/2; 600/439
(58) Field of Search .................... 601/2, 3; 600/439, 600/440, 441, 443

(56) References Cited

U.S. PATENT DOCUMENTS

| | | |
|---|---|---|
| 5,553,618 | * 9/1996 | Suzuki et al. . |
| 5,632,277 | 5/1997 | Chapman et al. . |
| 5,675,554 | 10/1997 | Cole et al. . |
| 5,706,819 | 1/1998 | Hwang et al. . |
| 5,827,188 | 10/1998 | Wright et al. . |
| 5,984,881 | * 11/1999 | Ishibashi et al. . |
| 6,086,535 | * 7/2000 | Ishibashi et al. . |

FOREIGN PATENT DOCUMENTS

| | | |
|---|---|---|
| 42 29 817 | 3/1994 | (DE) . |
| 0 627 206 | 12/1994 | (EP) . |

* cited by examiner

*Primary Examiner*—Marvin M. Lateef
*Assistant Examiner*—Shawna J Shaw
(74) *Attorney, Agent, or Firm*—Oblon, Spivak, McClelland, Maier & Neustadt, P.C.

(57) ABSTRACT

An ultrasonic therapeutic apparatus consisting of a therapeutic ultrasonic wave generating source driven by a driver circuit to generate therapeutic ultrasonic waves, an in vivo imaging probe so as to obtain a tissue tomographic image in the vicinity of the focus of the therapeutic ultrasonic waves. The imaging probe is used to receive echoes of the ultrasonic pulses emitted from therapeutic ultrasonic wave generating source. The driving conditions for the therapeutic ultrasonic wave generating source is adjusted on the basis of a received echo signal. The received echo signal contains information about actual intensity of the therapeutic ultrasonic waves within a living body, thus improving the safety and reliability of therapy.

2 Claims, 35 Drawing Sheets

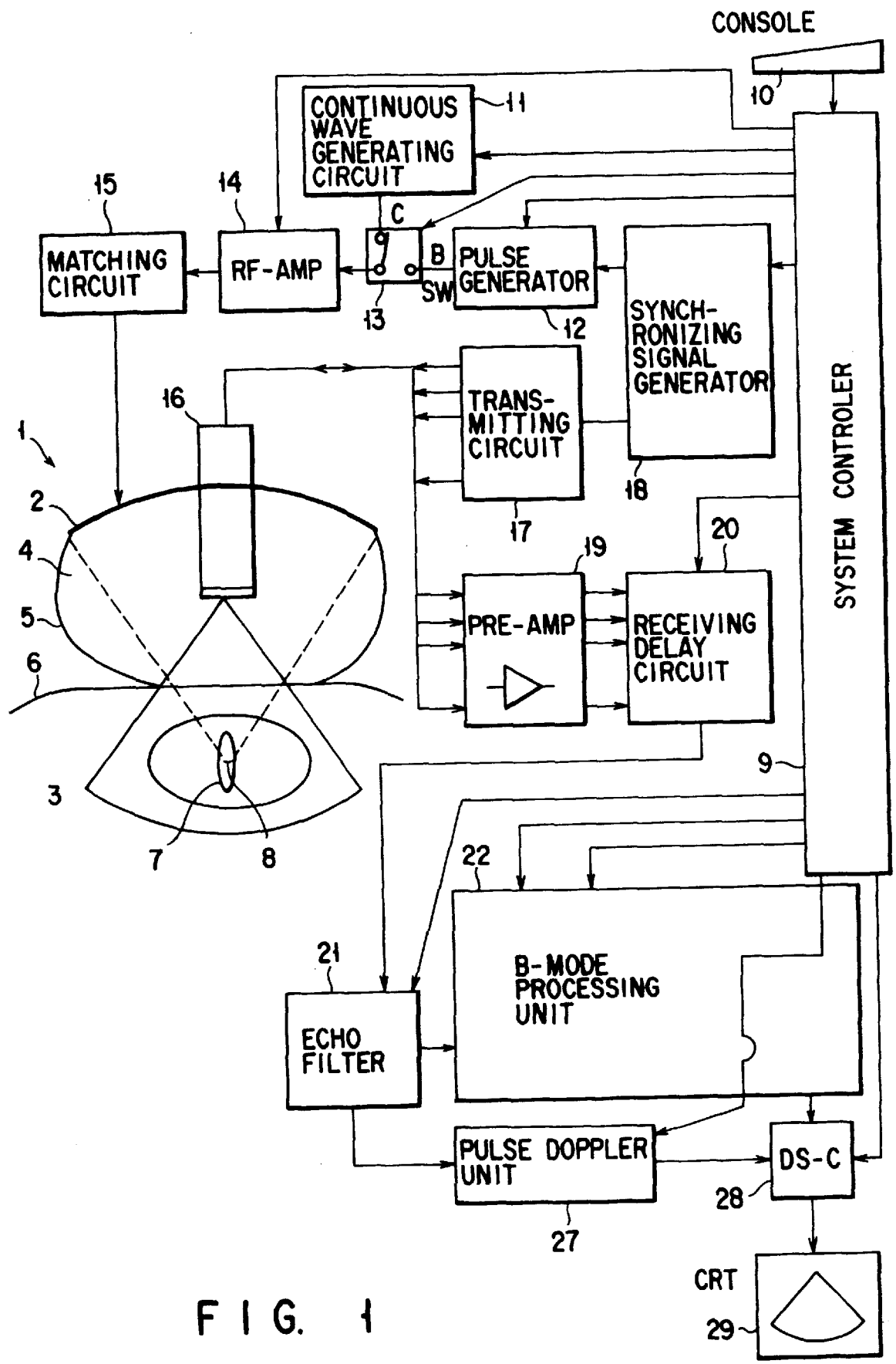
F I G. 1

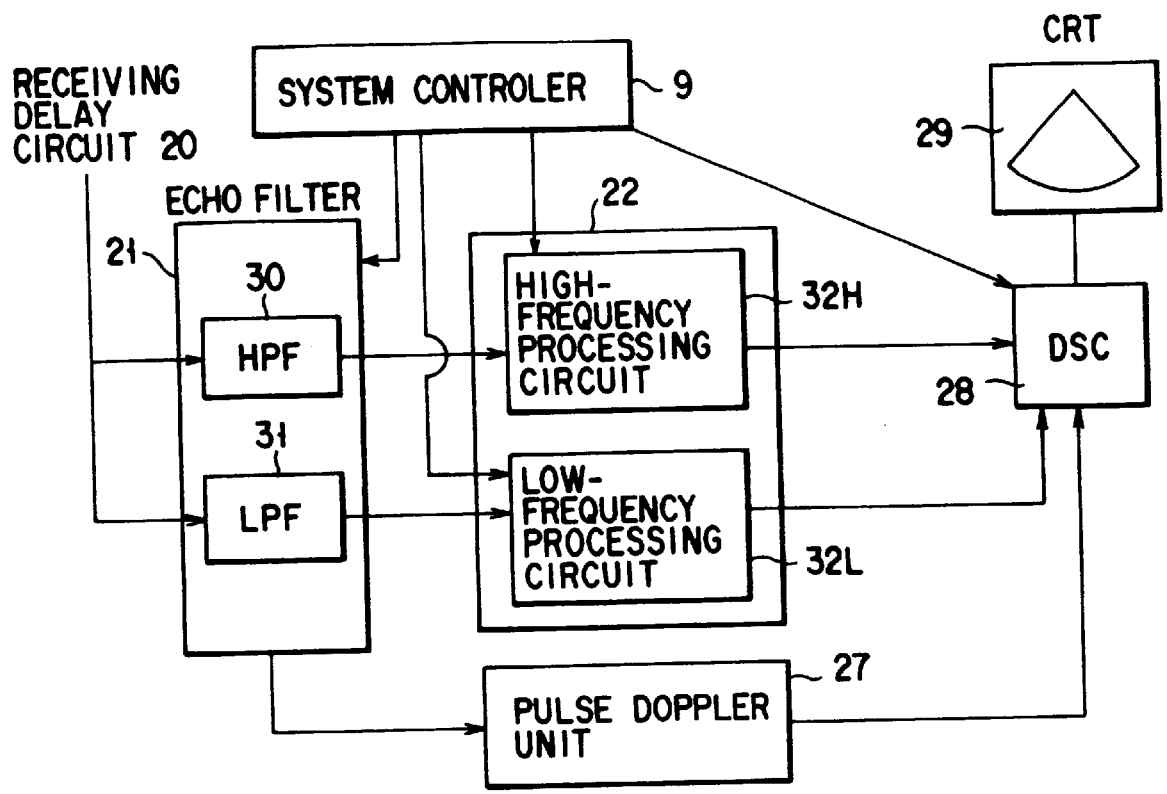
F I G. 2
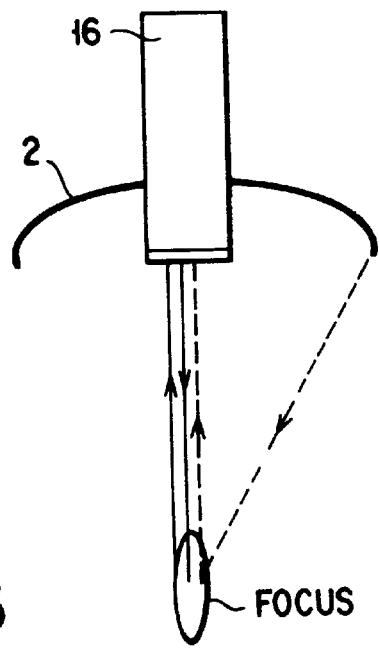
F I G. 3

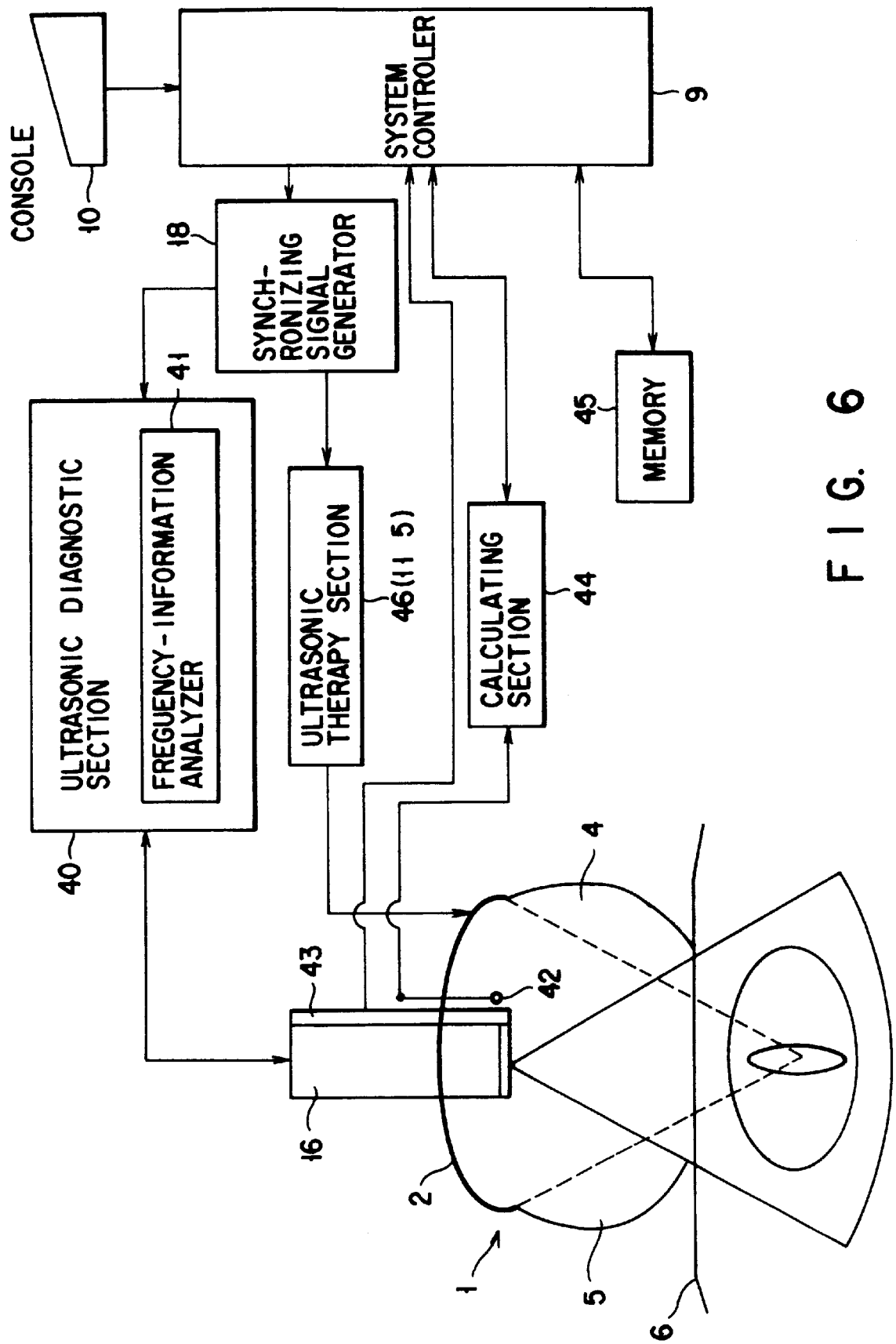
F I G. 6

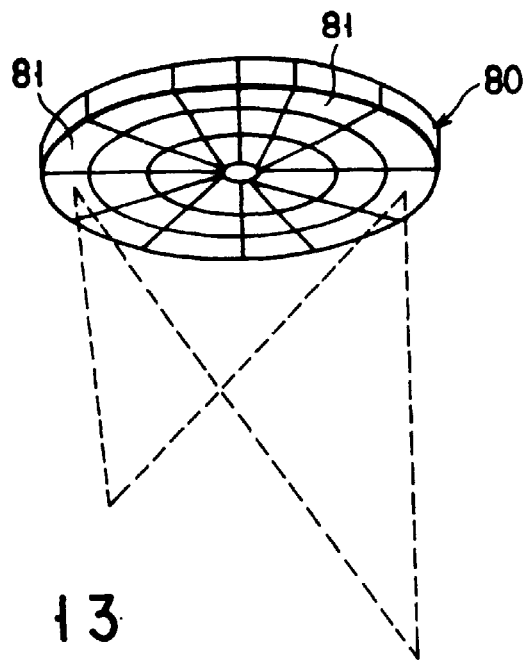
F I G. 13
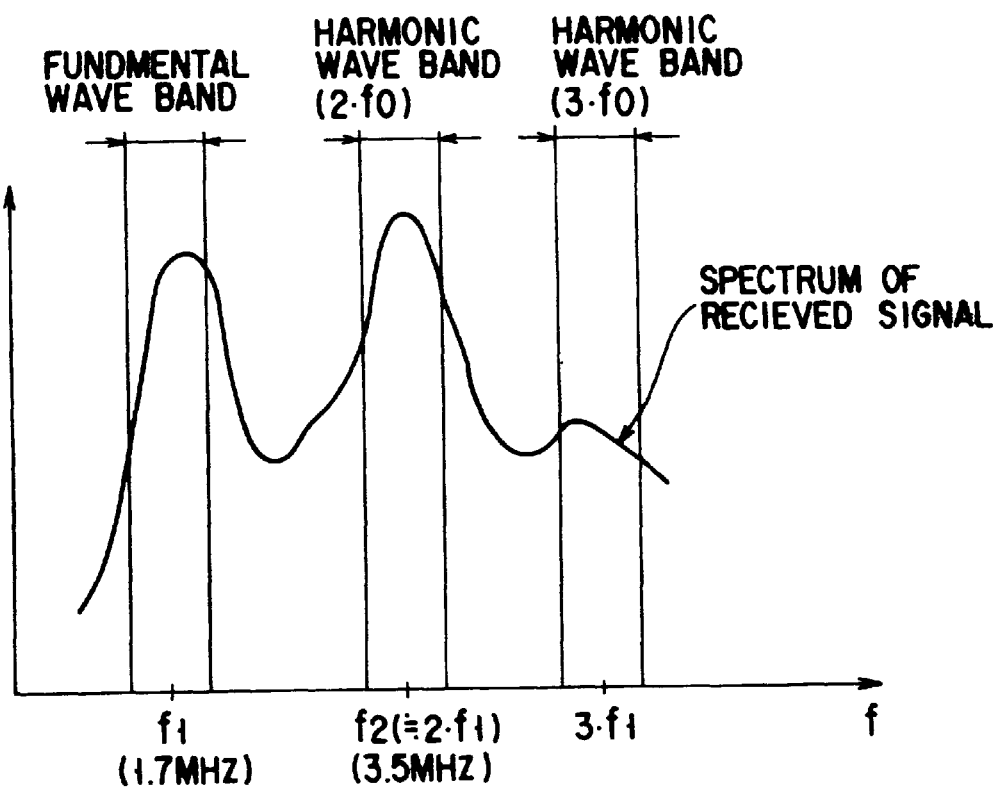
F I G. 14

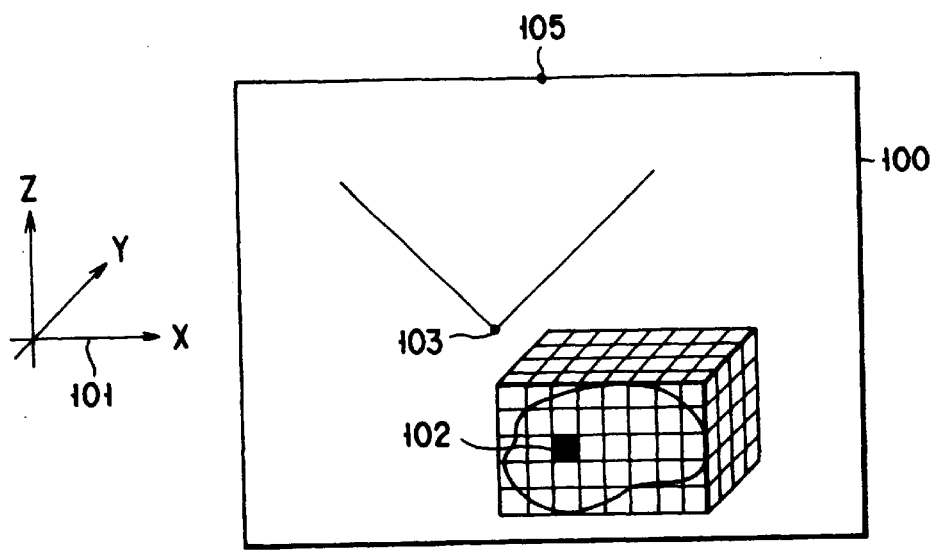
F I G. 15
$$104 \begin{cases} \blacksquare = (0,8,0) \\ \bullet = (-1,6,0) \end{cases}$$
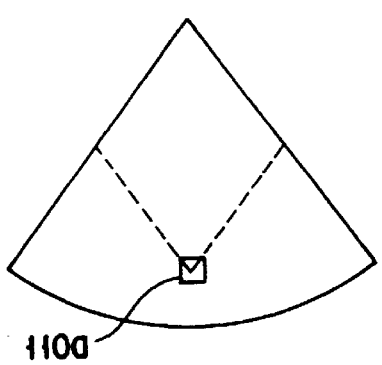
F I G. 16A
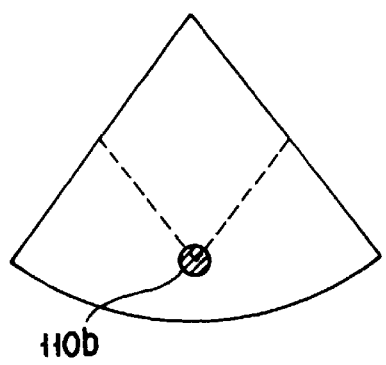
F I G. 16B
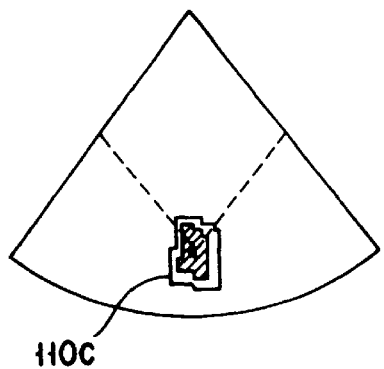
F I G. 16C

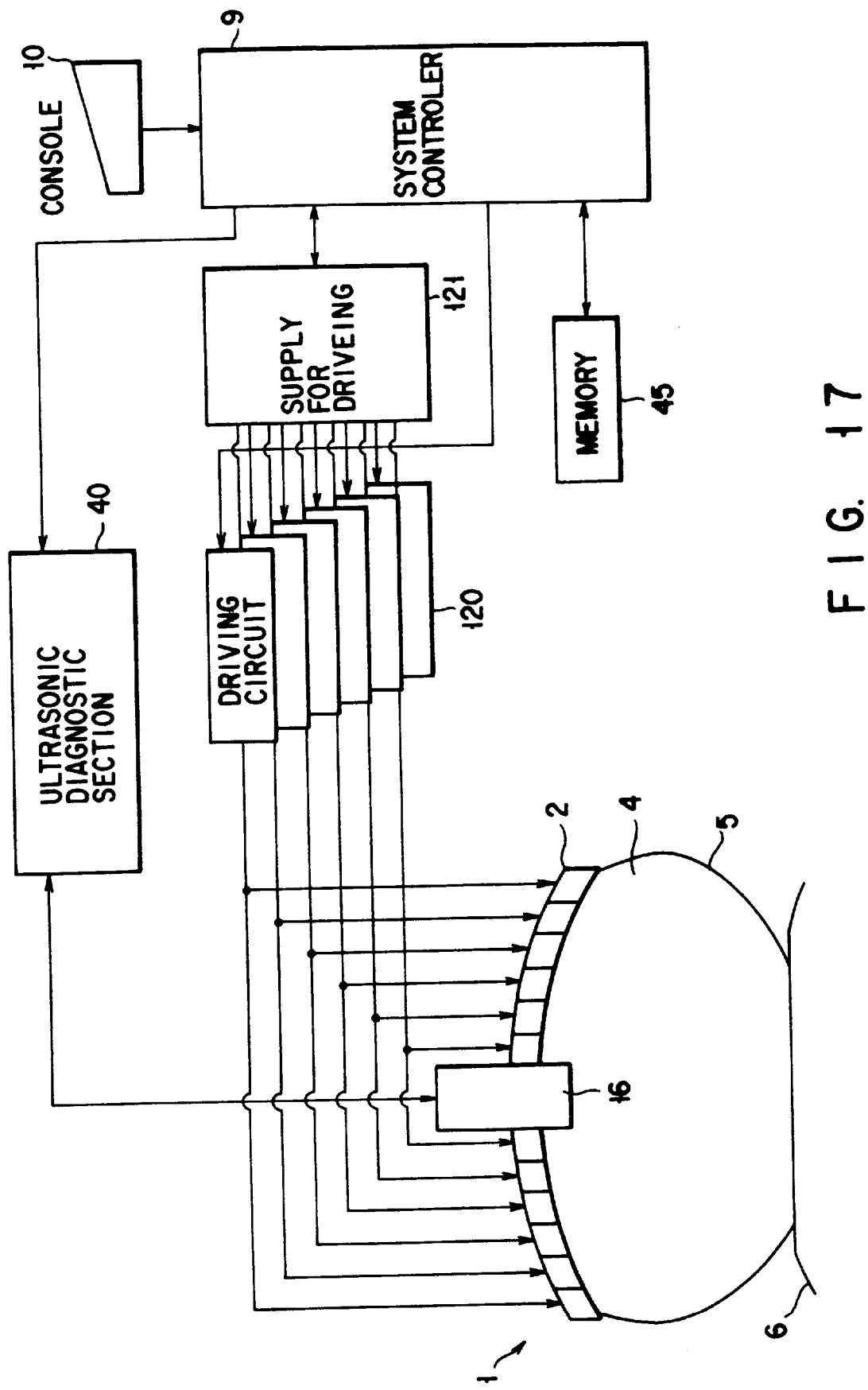
F I G. 17

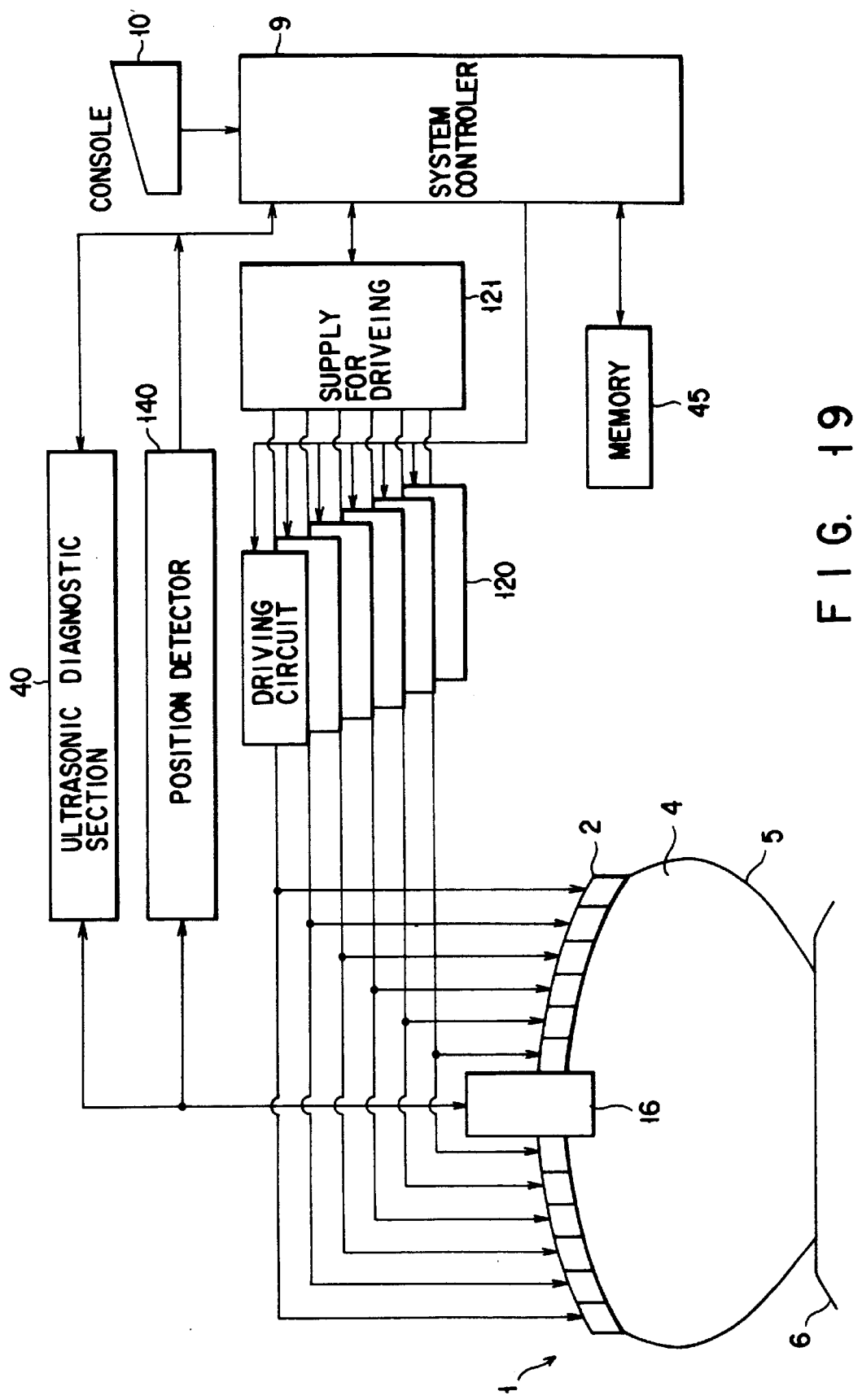
F I G. 19

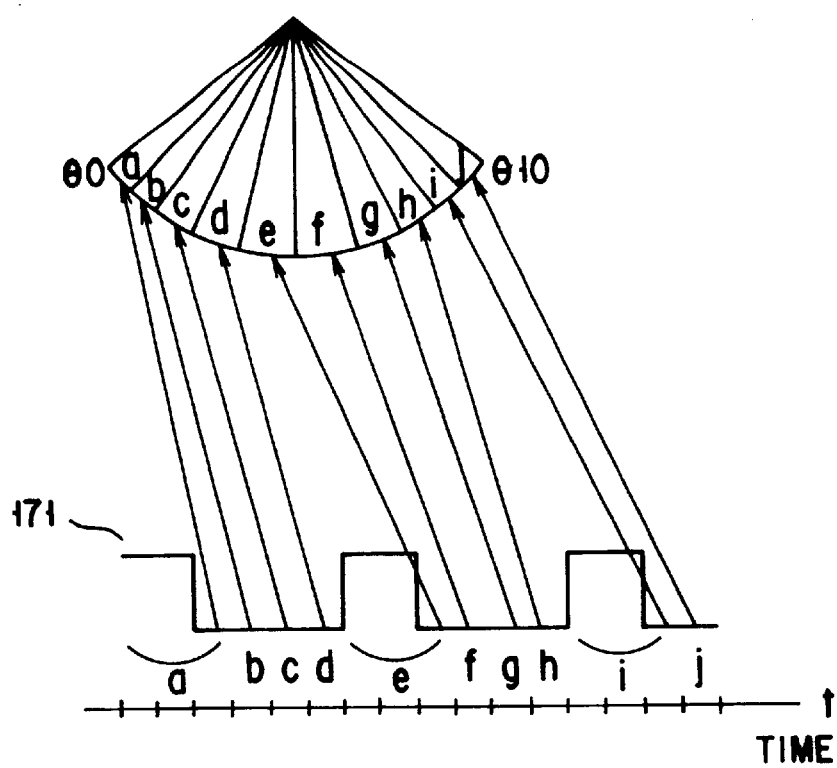
F I G. 23
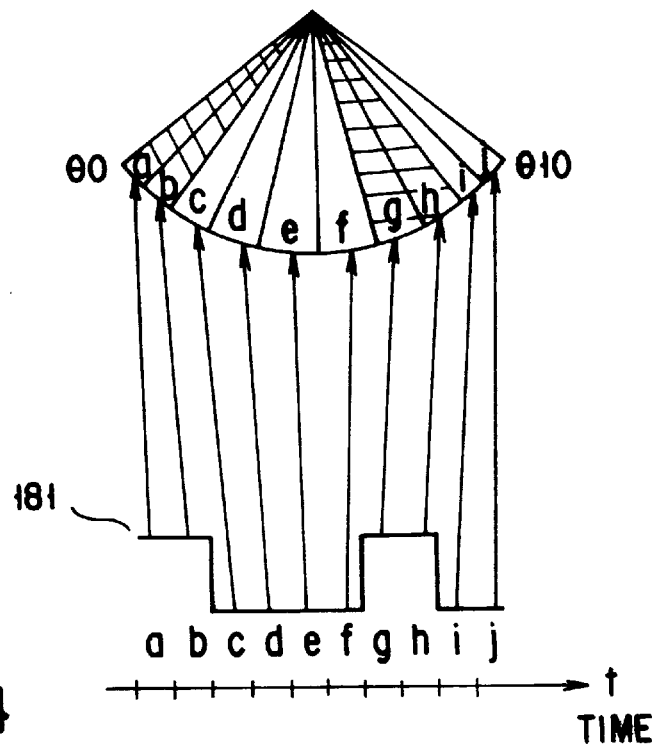
F I G. 24

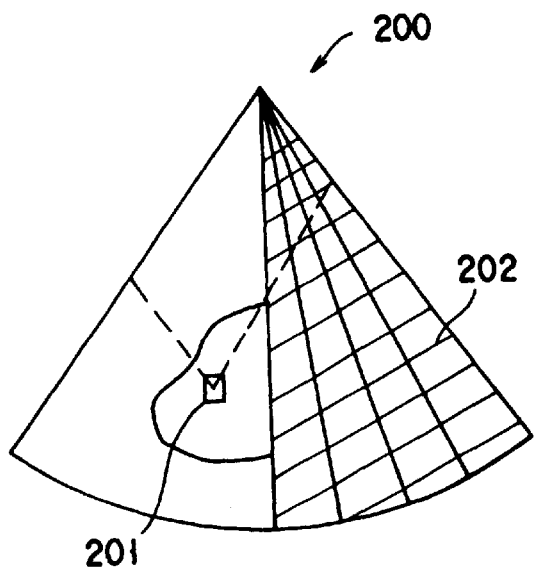
F I G. 26A
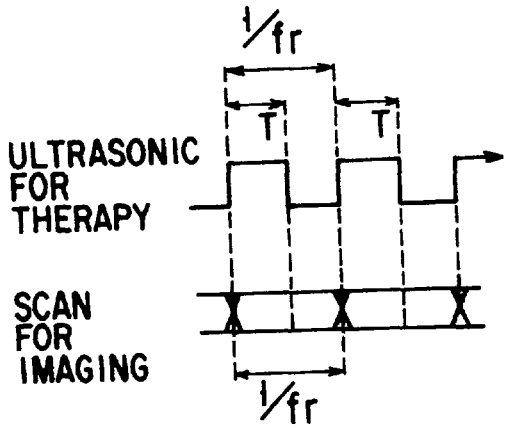
F I G. 26B
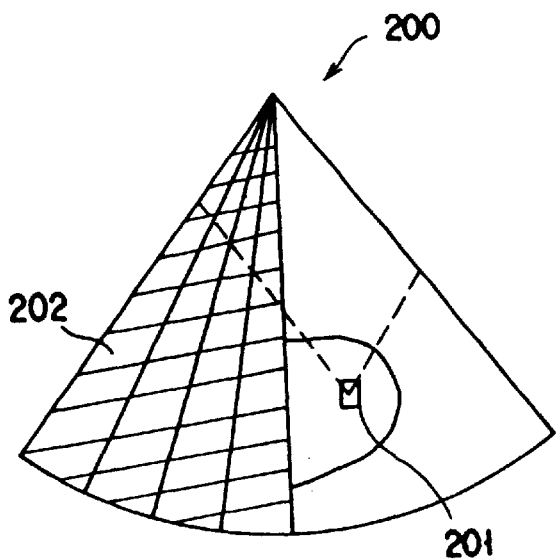
F I G. 26C
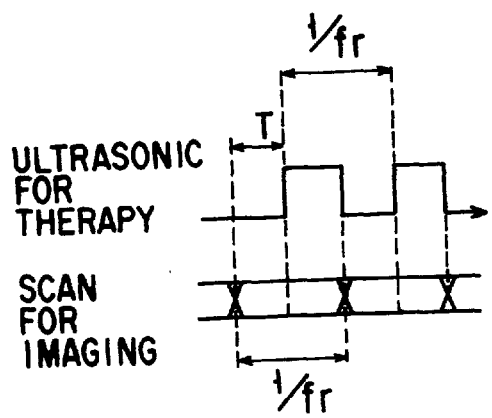
F I G. 26D

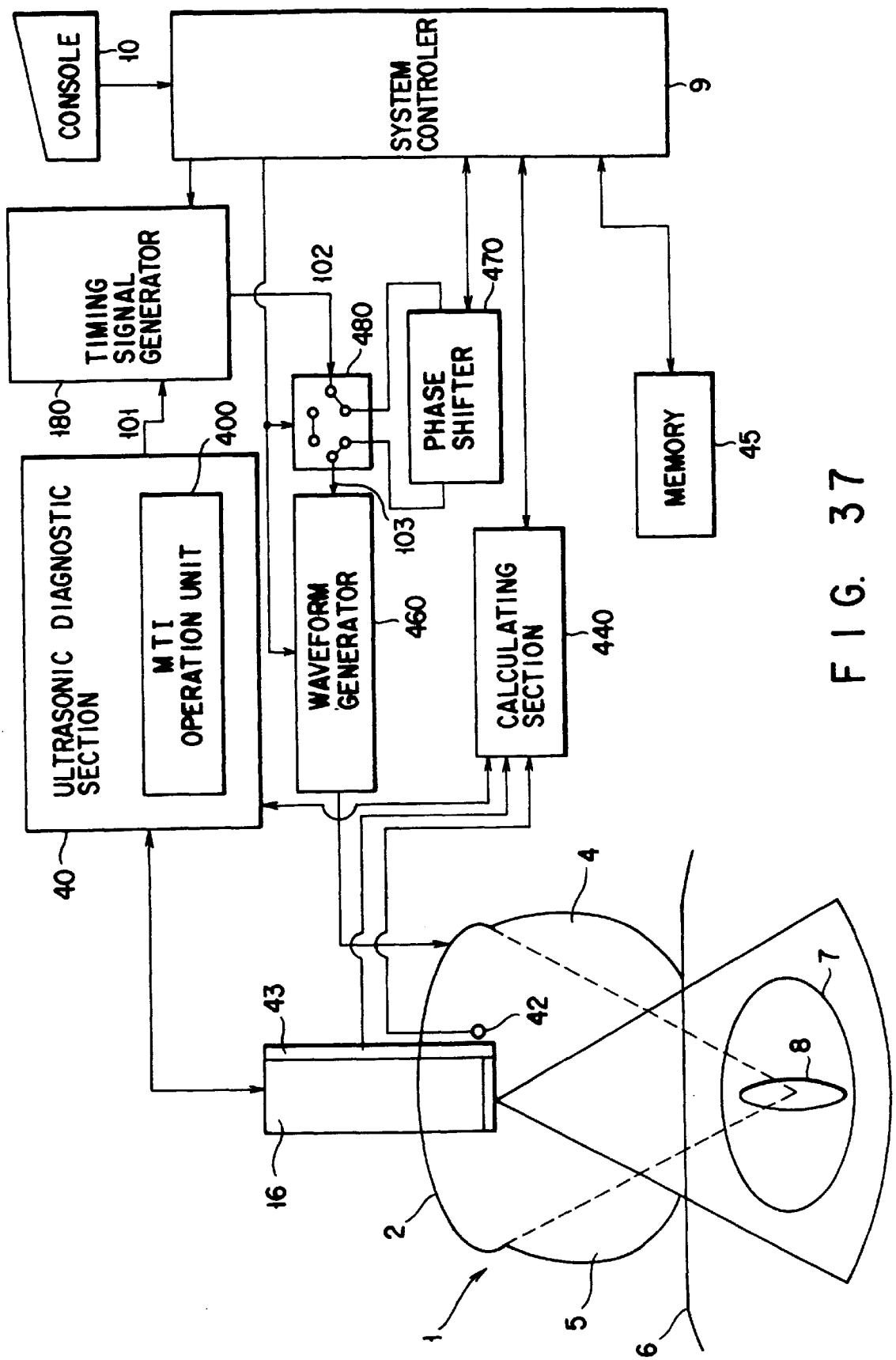
F I G. 37

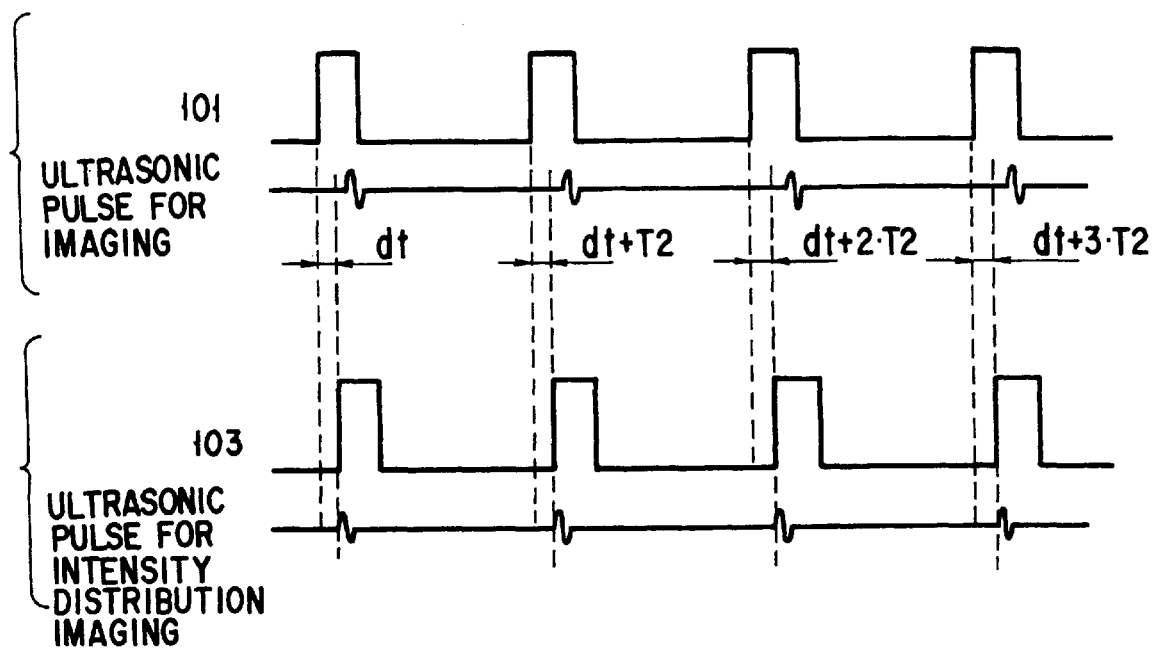
F I G. 39
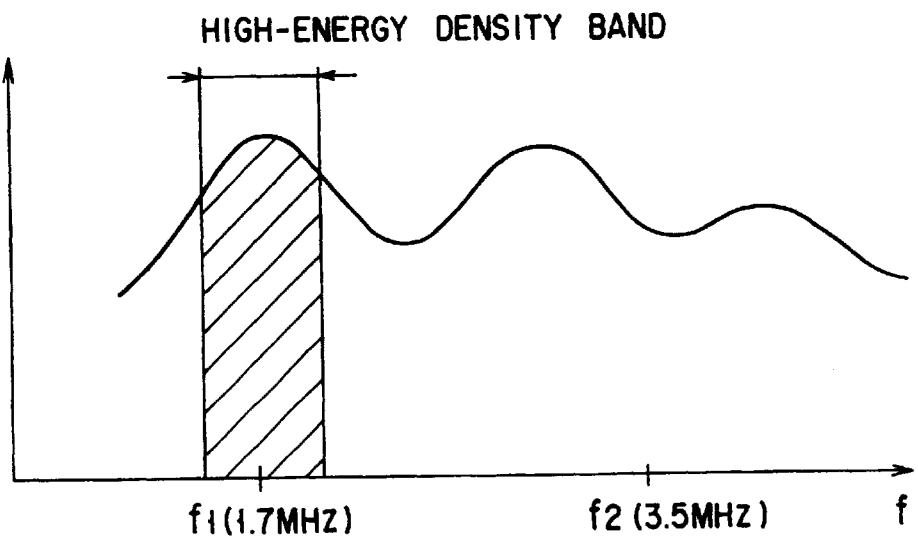
F I G. 41

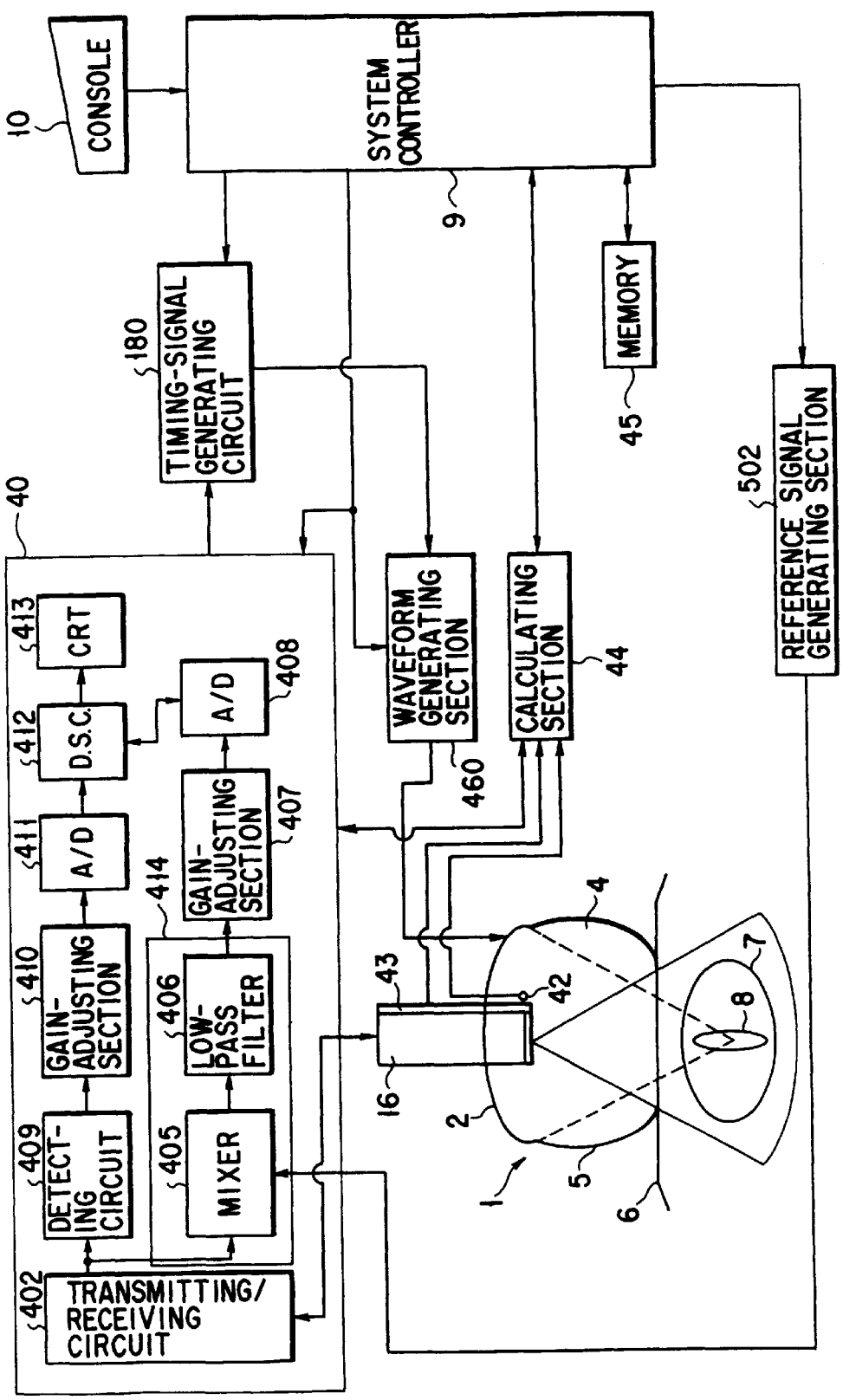
F I G. 40

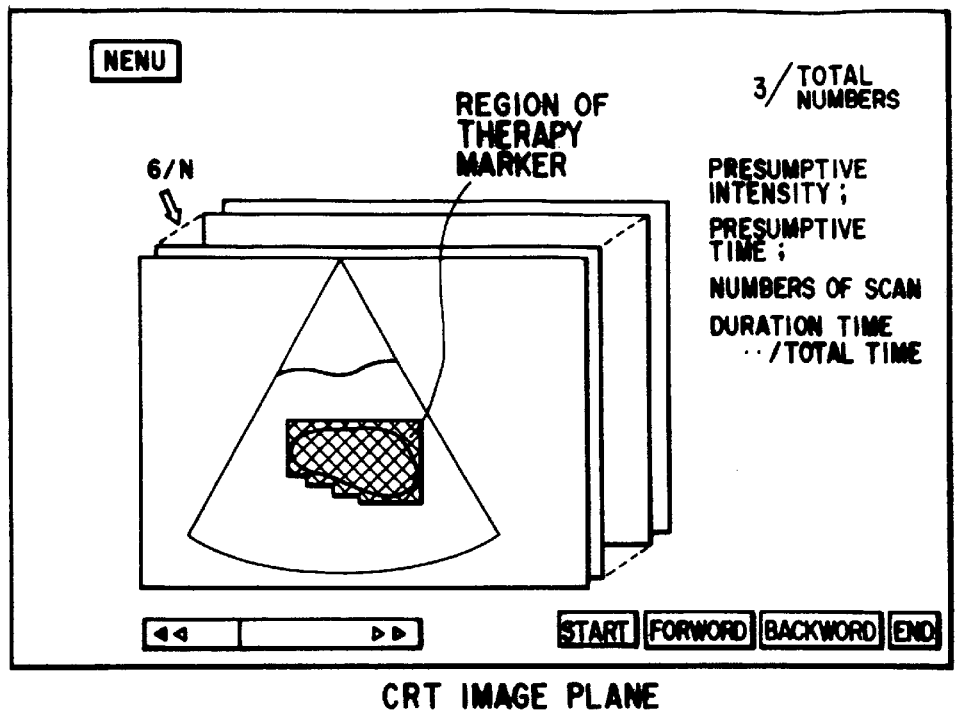
F I G. 47
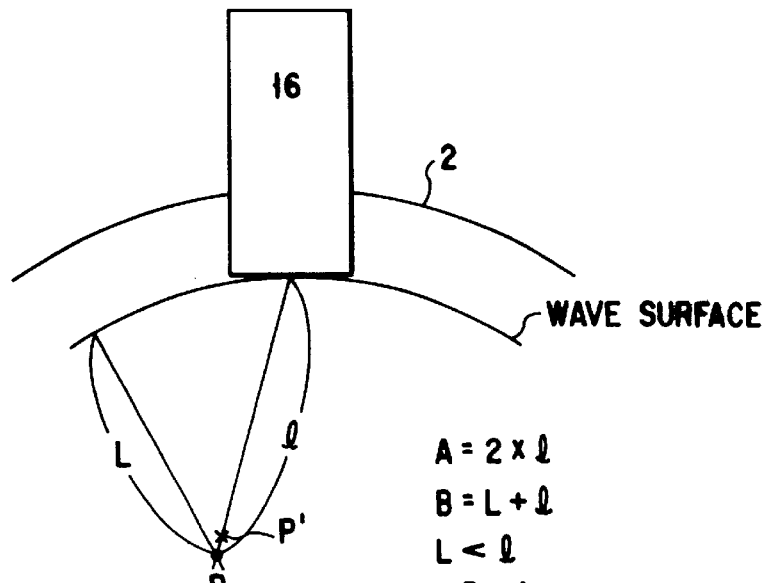
· FOCUS
F I G. 48

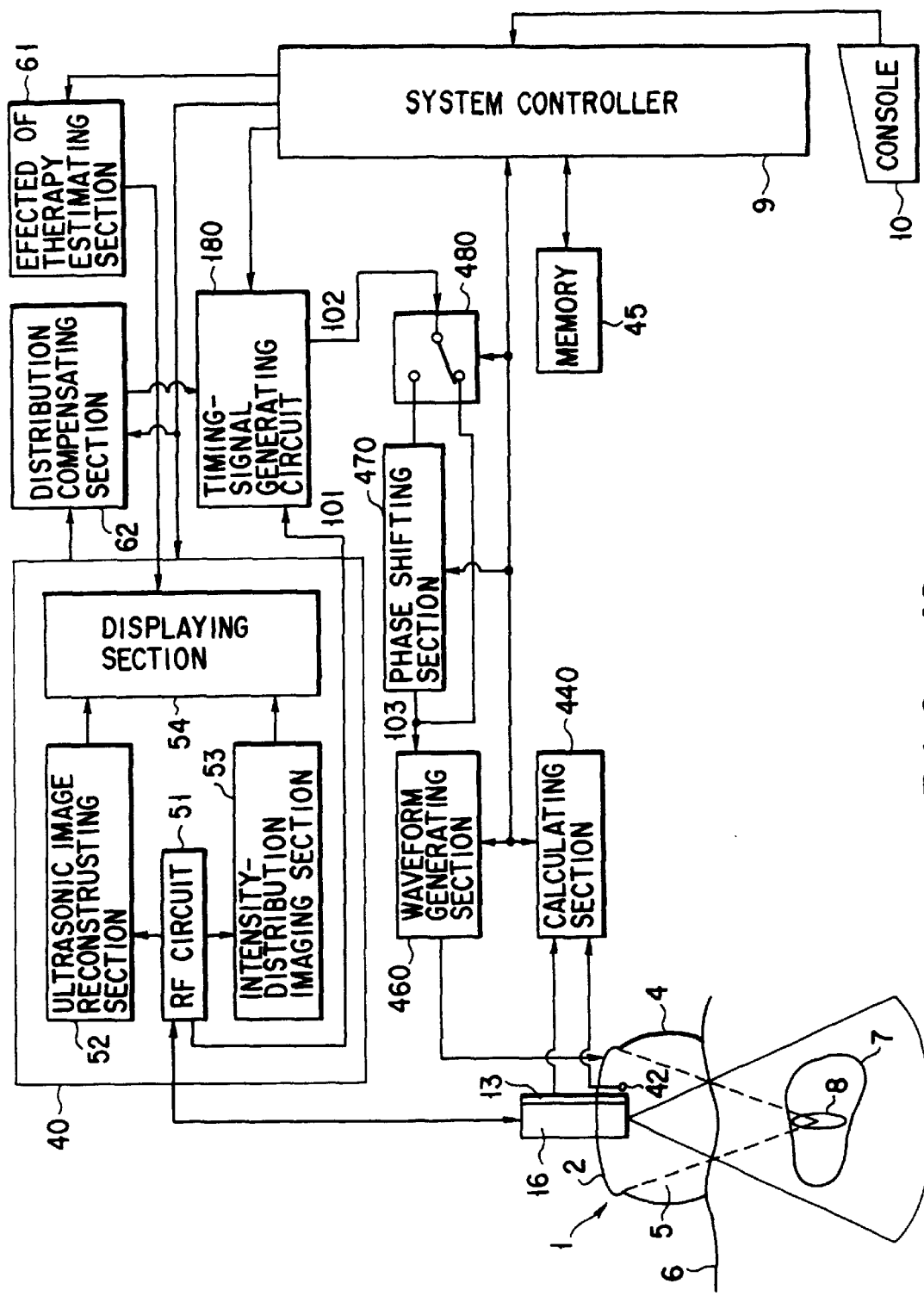
F I G. 49

ULTRASOUND THERAPEUTIC APPARATUS

This application is a Division of application Ser. No. 08/624,104 filed on Mar. 29, 1996 now U.S. Pat. No. 5,984,881.

BACKGROUND OF THE INVENTION

1. Field of the Invention

The invention relates to an ultrasound therapeutic apparatus which irradiates a diseased part of a patient with focused ultrasound beam for therapy thereof.

2. Description of the Related Art

In recent years, attention has been paid to minimally invasive treatment (MIT) a part of which is performed by ultrasonic therapeutic apparatus. Ultrasonic (Ultrasound) therapeutic apparatuses include shock wave lighotriptor which break a calculus with a focused ultrasonic beam and thermotherapy apparatuses which heat and necrotize a diseased part, such as a cancer, with focused ultrasonic beam.

A typical example of a strong ultrasound generating device is a piezoelectric type of device. This type of ultrasound generating device has great advantages that the focus of ultrasonic waves can be localized, few expendable parts are involved, intensity control is easy, the position of the focus can be changed easily by phase control (delay control) of drive voltages to a plurality of piezoelectric transducer elements, etc. (refer to Japanese Unexamined Patent Publication No. 60-145131 and U.S. Pat. No. 4,526,168).

The MIT is also a key word in the field of cancer therapy. Under the present conditions, most of cancer therapies rely on surgical operations. Thus, the outward form and the inherent function of an organ having cancer are destroyed very frequently. In such a case, so much strain will be put on a patient even if he or she lives long after operation. From a viewpoint of quality of life (QOL), therefore, the development of a new therapy (equipment) that is little invasive is being desired.

Under such circumstances, as one of therapies for malignant tumors, or cancers, the therapy by hyperthermia has drawn attention, which, using a difference in sensitivity to heat between tumor tissues and normal tissues, selectively destroys only cancer cells by heating a diseased part to 42.5° C. or more for a long period of time. As a method of application of heat to the body, a method of using electromagnetic waves such as microwaves has preceded. With this method, however, the electrical characteristics of a living body make it difficult to selectively heating a tumor in the deep of the body. Satisfactory results cannot therefore be expected for tumors existing 5 cm or more deep in the body. For this reason, a method of utilizing ultrasonic energy has been proposed for therapy for tumors existing in the deep of the body (refer to Japanese Unexamined Patent Publication No. 61-13955).

The ultrasound-based thermotherapy has been developed into a therapy which, by sharply focusing ultrasonic waves generated by piezoelectric transducer elements onto a diseased part, heats a tumor to 80° C. or more and necrotizes tumor tissues in an instant (refer to U.S. Pat. No. 5,150,711). In this therapy, unlike the conventional hyperthermia, it is a very important subject to precisely match the focus or point of application of focused ultrasonic waves with a diseased part in order to introduce ultrasonic waves at a very great intensity (some hundreds to some thousands of $W/cm^2$) into a restricted region in the vicinity of the focus of the ultrasonic waves and necrotize the diseased part instantly.

Methods of solving that problem are disclosed in Japanese Unexamined Patent Publications Nos. 61-13954, 61-13956, and 60-145131. According to these methods, the spatial intensity distribution of therapeutic ultrasonic waves is obtained by first detecting by an imaging probe echoes from the focus region of the waves pulses emitted from a therapeutic ultrasonic source, and then performing a B-mode process on the received echo signal.

However, these methods have the following problem. Whereas the frequency of the therapeutic ultrasonic waves is in the range of 1 to 3 MHz, the frequency of in vivo imaging ultrasonic waves is 3.5 MHz or more. The resonant frequency of imaging transducer elements coincides with the frequency of the imaging ultrasonic waves. Thus, the imaging probe will receive echoes of therapeutic ultrasonic waves with a very low sensitivity, failing to obtain the intensity distribution with precision.

According to one of these methods, an imaging probe receives echoes of imaging ultrasonic waves generated by that probe and echoes of ultrasonic pulses at the same time. The received signal having two components mixed in is then processed. Thus, this method has a problem that each image contrast cannot be adjusted individually.

According to another of these methods, imaging ultrasonic waves and ultrasonic pulses for intensity distribution are transmitted/received alternately. This approach has an advantage that each image contrast can be adjusted individually, but has a disadvantage that the frame rate is low, making it difficult to accomplish real-time processing.

Moreover, the above methods have the following problem. In general, in cautery treatment based on focusing of high-intensity ultrasonic waves, the location of a region onto which ultrasonic waves are focused and the location of a region to be treated do not match due to changes in acoustic characteristic of a cauterized region. Thus, even if the focus is matched to the part to be treated, the therapy will result in imperfection. Moreover, an adverse effect will also be produced on normal parts.

Furthermore, the above methods have the following problem. Ultrasonic pulses generated from a source of therapeutic ultrasonic waves are reflected from a region in the vicinity of the focus and the resulting echoes are received by an imaging probe. Likewise, imaging ultrasonic waves generated from the imaging probe are reflected from a region in the vicinity of the focus and the resulting echoes are received by the imaging probe. In order to cause a match to occur between the location of the focus on an intensity distribution image and the location of the focus on a B-mode tomographic image, the therapeutic ultrasonic waves and the imaging ultrasonic waves are generated at different times so that the resulting echoes corresponding to both types of waves from the focus will arrive at the probe at the same time. However, the timing of receiving of each echo from the same location other than the focus differs because of differences in propagation path. Thus, a spatial mismatch occurs between an intensity distribution image and a B-mode tomographic image.

SUMMARY OF THE INVENTION

It is an object of the invention to provide an ultrasonic therapeutic apparatus which permits the focus of ultrasonic waves to be matched to a treating region with high precision.

According to the present invention is provided an apparatus an ultrasonic therapeutic apparatus comprising:

a therapeutic ultrasonic wave generating source having resonant characteristics for a first fundamental frequency;

an ultrasonic probe having resonant characteristics for the first fundamental frequency and a second fundamental frequency;

driving means for driving the therapeutic ultrasonic wave generating source with a drive signal of the first fundamental frequency;

driving means for driving the ultrasonic probe with a drive signal of the second fundamental frequency to generate in vivo imaging ultrasonic waves;

receiving means for receiving echoes of first ultrasonic waves generated by the therapeutic ultrasonic wave generating source and echoes of second ultrasonic waves generated by the ultrasonic probe through the ultrasonic probe; and forming means for forming at least an intensity distribution image of the therapeutic ultrasonic waves in a subject or a tomographic image of the subject on the basis of a received echo signal output from the receiving means.

According to the present invention is provided an other apparatus an ultrasonic therapeutic apparatus comprising:

a therapeutic ultrasonic wave generating source having resonant characteristics for first and second fundamental frequencies;

an ultrasonic probe having resonant characteristics for the second fundamental frequency;

driving means for driving the therapeutic ultrasonic wave generating source with a drive signal of the first fundamental frequency at therapy time and with a drive signal of the second fundamental frequency at intensity distribution imaging time;

driving means for driving the ultrasonic probe with a drive signal of the second fundamental frequency to generate in vivo imaging ultrasonic waves;

receiving means for, at intensity distribution imaging time, receiving echoes of the therapeutic ultrasonic waves having a spectrum centered at the second fundamental frequency and echoes of the imaging ultrasonic waves having a spectrum centered at the second fundamental frequency; and forming means for forming at least an intensity distribution image of the therapeutic ultrasonic waves in a subject or a tomographic image of the subject on the basis of a received echo signal output from the receiving means.

According to the present invention is provided an other apparatus an ultrasonic therapeutic apparatus comprising:

a therapeutic ultrasonic wave generating source having resonant characteristics for a first fundamental frequency;

an ultrasonic probe having resonant characteristics for a second fundamental frequency;

driving means for driving the therapeutic ultrasonic wave generating source with a drive signal of the first fundamental frequency;

driving means for driving the ultrasonic probe with a drive signal of the second fundamental frequency to generate in vivo imaging ultrasonic waves;

receiving means for receiving echoes of first ultrasonic waves generated by the therapeutic ultrasonic wave generating source and echoes of second ultrasonic waves generated by the ultrasonic probe through the ultrasonic probe;

intensity distribution forming means for forming the intensity distribution image of the therapeutic ultrasonic waves in a subject on the basis of components in a specific band corresponding to the first fundamental frequency that are contained in a received echo signal from the receiving means; and forming means for forming a tomographic image of the subject on the basis of components in a band having the second fundamental frequency that are contained in the received echo signal output from the receiving means.

According to the present invention is provided an other apparatus an ultrasonic therapeutic apparatus comprising:

a source of therapeutic ultrasonic waves;

an ultrasonic probe;

driving means for driving the source to generate first ultrasonic waves; and adjust means for adjusting drive conditions of the driving means on the basis of echoes of the first ultrasonic waves received through the ultrasonic probe.

According to the present invention is provided an other apparatus an ultrasonic therapeutic apparatus comprising:

a source of therapeutic ultrasonic waves;

an ultrasonic probe;

first driving means for driving the source to generate first ultrasonic waves;

second driving means for driving the ultrasonic probe to generate imaging ultrasonic waves;

means for forming the intensity distribution of the first ultrasonic waves and a tomographic image of a subject on the basis of echoes of the first ultrasonic waves and echoes of the imaging ultrasonic waves received through the ultrasonic probe; and determination means for determining the presence or absence of an obstruction to ultrasonic waves on the basis of the shape of the intensity distribution.

According to the present invention is provided an other apparatus an ultrasonic therapeutic apparatus comprising:

a source of therapeutic ultrasonic waves;

an ultrasonic probe;

means for driving the source to generate therapeutic ultrasonic waves;

means for driving the ultrasonic probe to generate imaging ultrasonic pulses;

receiving means for receiving echoes through the ultrasonic probe;

means for forming a tomographic image of a subject on the basis of the echoes received; and means for adjusting the timing of the therapeutic ultrasonic waves so that noise resulting from the therapeutic ultrasonic waves being stronger than the imaging ultrasonic pulses will appear in other portions of the tomographic image than a portion of interest.

According to the present invention is provided an other apparatus an ultrasonic therapeutic apparatus comprising:

a source of therapeutic ultrasonic waves;

driving means for driving the source to generate therapeutic ultrasonic waves;

a magnetic resonance diagnostic apparatus for measuring the temperature distribution in the vicinity of the focus onto which the therapeutic ultrasonic waves converge; and means for adjusting drive conditions of the drive means according to the temperature distribution.

According to the present invention is provided an other apparatus an ultrasonic therapeutic apparatus comprising:

a source of therapeutic ultrasonic waves;

an ultrasonic probe;

driving means for driving the source to generate first ultrasonic waves;

forming means for forming intensity distribution of the first ultrasonic waves on the basis of echoes of the first ultrasonic waves received through the ultrasonic probe;

magnetic resonance diagnostic means for measuring one-dimensional temperature distribution; and estimation means for estimating two-dimensional temperature distribution on the basis of the intensity distribution and the one-dimensional temperature distribution.

According to the present invention is provided an other apparatus an ultrasonic therapeutic apparatus comprising:

a source of therapeutic ultrasonic waves;

an ultrasonic probe;

sync signal generating means for generating first and second sync signals;

driving means for driving the source of therapeutic ultrasonic waves according to the first sync signal;

driving means for driving the ultrasonic probe according to the second sync signal;

phase shift means for changing the difference of the first sync signal in time relative to the second sync signal to impart phase differences to echoes of first ultrasonic wave generated by the therapeutic ultrasonic wave generating means.

receiving means for receiving echoes of the first ultrasonic waves and echoes of second ultrasonic waves generated by the ultrasonic probe through the ultrasonic probe; and forming means for forming an image on the basis of received signals output repeatedly from the receive means, the received signals being phase-shifted by the phase shift means.

According to the present invention is provided an other apparatus an ultrasonic therapeutic apparatus comprising:

a source of therapeutic ultrasonic waves;

an ultrasonic probe;

means for driving the source of therapeutic ultrasonic waves;

means for driving the ultrasonic probe to generate imaging ultrasonic waves;

receiving means for receiving echoes of first ultrasonic waves generated by the therapeutic ultrasonic wave generating source and echoes of second ultrasonic waves generated by the ultrasonic probe through the ultrasonic probe;

first filtering means for extracting a first component within a first specific band corresponding to the fundamental frequency of the first ultrasonic waves from an output of the receiving means;

second filtering means for extracting a second component within a specific band corresponding to the fundamental frequency of the second ultrasonic waves from the output of the receiving means;

means for amplifying each of the first and second components individually; and means for forming an image on the basis of the first and second components amplified by the amplifying means.

According to the present invention is provided an other apparatus an ultrasonic therapeutic apparatus comprising:

a therapeutic ultrasonic wave generating source having first resonant characteristics for a first frequency;

an ultrasonic probe having second resonant characteristics for a second frequency;

means for applying to the therapeutic ultrasonic wave generating source a drive signal of a frequency between the first and second frequencies;

means for driving the ultrasonic probe to generate imaging ultrasonic waves;

receiving means for receiving echoes of ultrasonic waves from emitted the therapeutic ultrasonic wave generating source and echoes of the imaging ultrasonic ultrasonic waves through the ultrasonic probe; and means for constructing an image on the basis of an output of the receiving means.

According to the present invention is provided an other apparatus an ultrasonic therapeutic apparatus comprising:

a source of therapeutic ultrasonic waves;

an ultrasonic probe;

first drive means for driving the source of therapeutic ultrasonic waves;

second drive means for driving the ultrasonic probe to generate in vivo imaging ultrasonic waves;

constructing means for constructing the intensity distribution of the therapeutic ultrasonic waves and a tomographic image of a subject on the basis of echoes of first ultrasonic waves from the source and echoes of second ultrasonic waves from the ultrasonic probe received through the ultrasonic probe; and means for estimating a treating region which is heated to a predetermined temperature or more on the basis of the intensity distribution.

According to the present invention is provided an other apparatus an ultrasonic therapeutic apparatus comprising:

a source of therapeutic ultrasonic waves;

an ultrasonic probe;

drive means for driving the source of therapeutic ultrasonic waves to generate ultrasonic waves that converge onto a focus;

drive means for driving the ultrasonic probe to generate in vivo imaging ultrasonic waves;

constructing means for constructing the intensity distribution of the ultrasonic waves and a tomographic image of a subject on the basis of echoes of the ultrasonic waves from the source and echoes of the imaging ultrasonic waves from the ultrasonic probe received through the ultrasonic probe; and means for detecting a focal region of therapeutic ultrasonic waves on the basis of the intensity distribution;

means for forming the focus of therapeutic ultrasonic waves in a first focal position and a second focal position; and means for displaying a combined region of a first focal region corresponding to the first focal position and a second focal region corresponding to the second focal position on the tomographic image.

According to the present invention is provided an apparatus an ultrasonic therapeutic apparatus comprising:

a source of therapeutic ultrasonic waves;

an ultrasonic probe;

drive means for driving the source of therapeutic ultrasonic waves to generate first ultrasonic waves;

drive means for driving the ultrasonic probe to generate second ultrasonic waves for in vivo imaging;

constructing means for constructing the intensity distribution of the first ultrasonic waves and a tomographic image of a subject on the basis of echoes of the first ultrasonic waves from the source and echoes of the second ultrasonic waves from the ultrasonic probe received through the ultrasonic probe; and means for correcting spatial displacement of the intensity distribution with respect to the tomographic image on the basis of differences among propagation paths of ultrasonic waves.

According to the present invention is provided an other apparatus an ultrasonic therapeutic apparatus comprising:

a source of therapeutic ultrasonic waves;

an ultrasonic probe;

drive means for driving the source of therapeutic ultrasonic waves to generate first ultrasonic waves;

drive means for driving the ultrasonic probe to generate second ultrasonic waves for in vivo imaging;

constructing means for constructing the intensity distribution of the first ultrasonic waves and a tomographic image of a subject on the basis of echoes of the first ultrasonic waves from the source and echoes of the second ultrasonic waves from the ultrasonic probe received through the ultrasonic probe; and means for adjusting the timing of the first ultrasonic waves relative to the second ultrasonic waves to correct spatial displacement of the intensity distribution with respect to the tomographic image on the basis of differences among propagation paths of ultrasonic waves.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 1 shows an arrangement of an ultrasonic therapeutic apparatus according to a first embodiment of the invention;

FIG. 2 is a block diagram of the ultrasonic diagnostic section of FIG. 1;

FIG. 3 shows propagation paths of ultrasonic waves;

FIG. 6 shows an arrangement of an ultrasonic therapeutic apparatus according to a third embodiment of the invention;

FIG. 13 is a schematic representation of a source of therapeutic ultrasonic waves;

FIG. 14 shows a high-frequency band;

FIG. 15 shows a deviation between the recognized focus and the presumed heated region;

FIGS. 16A, 16B and 16C show a focus marker and a heated region marker;

FIG. 17 shows an arrangement of an ultrasonic therapeutic apparatus according to a sixth embodiment of the invention;

FIG. 19 shows an arrangement of an ultrasonic therapeutic apparatus according to a seventh embodiment of the invention;

FIG. 23 is a diagram for use in explanation of a second method of solving the problems associated with FIGS. 20A and 20B;

FIG. 24 is a diagram for use in explanation of a third method of solving the problems associated with FIGS. 20A and 2OB;

FIGS. 26A through 26D are diagrams for use in explanation of a fourth method of solving the problems associated with FIGS. 20A and 20B;

FIG. 37 shows an arrangement of an ultrasonic therapeutic apparatus according to a tenth embodiment of the invention;

FIG. 39 is a diagram for use in explanation of phase shifts of a sync signal;

FIG. 40 shows an arrangement of an ultrasonic wave application apparatus according to an eleventh embodiment of the invention;

FIG. 41 shows frequency characteristics of the quadrature detector of FIG. 40;

FIG. 47 shows an example of a display image on the display unit of FIG. 46;

FIG. 48 is a diagram useful in explaining the principle of the occurrence of spatial mismatch between a B-mode image and an intensity distribution image;

FIG. 49 shows an arrangement of an ultrasonic wave application apparatus according to a thirteenth embodiment of the invention;

DETAILED DESCRIPTION OF THE PREFERRED EMBODIMENTS

Figure 4:
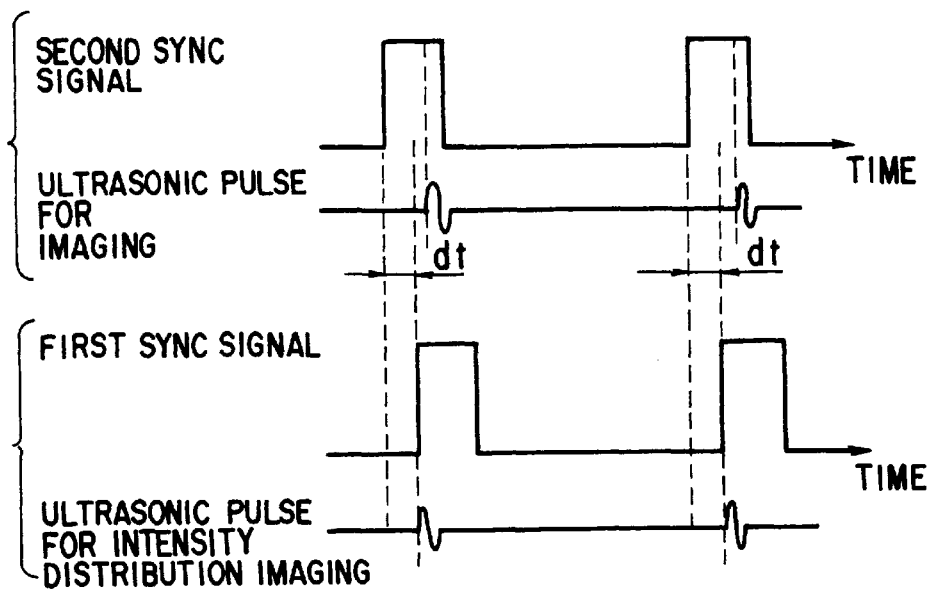
FIG. 4 shows a difference between the timing of an in vivo imaging ultrasonic pulse and the timing of an intensity distribution imaging ultrasonic pulse.

Ultrasonic therapeutic apparatuses include calculus breaking apparatuses which break a calculus by a focused beam of ultrasound and thermotherapeutic apparatuses which heat and necrotize a diseased part, such as a cancer, by a focused beam of ultrasound. A thermotherapeutic apparatus will be described herein by way of example.

First Embodiment

Referring now to FIG. 1, there is shown an arrangement of an ultrasonic therapeutic apparatus according to a first embodiment of the invention. An ultrasonic applicator 1 has a source (transducer array) 2 of therapeutic ultrasonic waves, which has, for example, a plurality of piezoelectric transducer elements arranged in a spherical bowl. Ultrasonic waves generated from the transducer elements converge on the center of the spherical bowl. The point of the convergence is referred to as the geometrical focus. In the vicinity of the center of the therapeutic ultrasonic source 2 is formed an opening into which an imaging probe 16 is inserted for generating in vivo imaging ultrasonic waves. A water bag 5 that contains a coupling liquid 4 is provided on the front side of the therapeutic ultrasonic source 2. Ultrasonic waves generated from the therapeutic ultrasonic source 2 and the imaging probe 16 travel through the coupling liquid to a patient 3.

In this description, it is supposed that therapeutic ultrasonic source 2 is comprised one piezoelectric element. Of course, source 2 may be comprise of several successive elements.

A synchronization circuit 18 supplies a pulse generator 12 with a first sync signal. In responsive to this, the pulse generator 12 generates signal pulses of a first fundamental frequency f1 that coincides with the resonant frequency of the piezoelectric transducer elements which corresponds to their thickness. The frequency f1 is 1.7 MHz by way of example. The signal pulses are applied to an RF amplifier 14 via a switch 13. At the time of imaging the intensity distribution (operation mode B), the switch 13 is set to the B position.

The RF amplifier 14 amplifies the signal pulses to produce drive pulses, which are applied to the piezoelectric elements of the treatment transducer array 2 via a matching circuit 15, thereby producing strong ultrasonic waves for intensity distribution imaging.

The ultrasonic waves for intensity distribution are produced from the ultrasonic transducer array 2 in a frequency band centered at the first fundamental frequency f1. Echoes of these ultrasonic waves are received by the imaging probe 16.

A continuous wave generator 11 continuously generates a continuous signal of the first fundamental frequency f1, which is applied to the RF amplifier 14 via the switch 13. At the time of treatment (operation mode C), the switch 13 is placed to the C position. The RF amplifier 14 amplifies the continuous signal to produce a drive signal continuously. The magnitude of the drive signal is selected to be greater than that of the drive pulse for intensity distribution. The drive signal is applied continuously to the piezoelectric elements of the therapeutic transducer array 2 via the matching circuit 15. The therapeutic ultrasonic waves are generated continuously from the source 2 in a frequency band centered at the first fundamental frequency f1 and converge on the focus, thereby heating and necrotizing an abnormal tissue such as a cancer.

The imaging probe 16 has an array of a plurality of tiny piezoelectric transducer elements. The probe may be of any type of scan, including sector scan, linear scan, etc. The probe will be described herein as being of the sector scan type.

The piezoelectric transducer elements of the imaging probe 16 have peaks of sensitivity in both a low-frequency band containing the first fundamental frequency f1 of the ultrasonic waves for therapy and intensity distribution and a high-frequency band containing a second fundamental frequency f2 for imaging ultrasonic waves. For this reason, the piezoelectric elements of the probe 16 are fabricated to have a two-layer structure or a hybrid structure, as disclosed in Japanese Unexamined Patent Publication No. 4-211599. With the two-layer structure, an array of piezoelectric elements having a thickness corresponding to the first fundamental frequency f1 and an array of piezoelectric elements having a thickness corresponding to the second fundamental frequency f2 are stacked one on top of the other with a common electrode sandwiched therebetween. With the hybrid structure, an array of piezoelectric elements of a thickness corresponding to the first frequency f1 and an array of piezoelectric elements of a thickness corresponding to the second frequency f2 are juxtaposed. Each piezoelectric element is coated on top and bottom with electrode metal.

The synchronization circuit 18 applies a second sync signal to a transmission circuit 17 that includes a pulse generator, a transmit delay circuit, and a pulser. The pulse generator periodically generates signal pulses of the second fundamental frequency f2 in response to the second sync signal. The second frequency f2 is different from the first frequency f1 and coincides with a resonant frequency corresponding to the thickness of the piezoelectric elements of the probe 16. It is assumed here that the frequency f2 is higher than the frequency f1. The second frequency is 3.5 MHz by way of example. The signal pulses are distributed to the respective channels and imparted, in the transmit delay circuit, with a different delay time for each channel so as to focus ultrasonic waves into a beam and steer a focused beam of ultrasonic waves in a desired direction. The delayed signal pulses are then fed into the pulser. The pulser amplifies the signal pulses and produces drive pulses which are applied to the piezoelectric elements of the imaging probe 16. Thus, in vivo imaging ultrasonic waves are produced. Echoes of the ultrasonic waves are received by the imaging probe 16. Received echo signals are applied through a preamplifier circuit 19 to a receive delay circuit 20 for each channel. The receive delay circuit 20 provides different delay times to the received echo signals each associated with a respective one of channels and sums the received echo signals, thereby determining receive directivity.

An output signal of the receive delay circuit 20 is applied through an echo filter 21 to a B-mode processing unit 22, which produces B-mode image data and intensity distribution data. The B-mode image data and the intensity distribution data are converted by a digital scan converter (DSC) to television video signals which, in turn, are displayed on a CRT 29.

The output signal of the receive delay circuit 20 is also applied through the echo filter 21 to a pulsed Doppler unit 27, which comprises a quadrature detector, an analog-to-digital converter, an MTI filter, an auto-correlator, and an operation unit and produces a color Doppler image data. This image data is displayed on the CRT 29 after being processed by the digital scan converter 28.

As shown in FIG. 2, the echo filter 21 comprises a highpass filter (HPF) 30 and a lowpass filter (LPF) 31. The B-mode processing unit 22 has a high-frequency processing circuit 32H and a low-frequency processing circuit 32L. High-frequency components in the output signal of the receive delay circuit 20 are applied through the highpass filter 30 to the high-frequency processing circuit 32H, which produces tissue tomographic image data from the high-frequency components. The low-frequency processing circuit 32L produces intensity distribution data from the low-frequency components (components corresponding to the first fundamental frequency f1). Each of the high-frequency and low-frequency processing circuits 32H and 32L comprises a sensitive time control (STC) circuit which makes changes in attenuation with depth uniform, a log amplifier, a detector, and an analog-to-digital converter.

Next, the operation of the first embodiment will be described. There are three modes of operation, A, B and C. In the operation mode A, the therapeutic ultrasonic transducer 2 is not driven, while the imaging probe 16 is driven. The imaging probe generates ultrasonic waves to scan a plane section of the patient 7 in the vicinity of his or her diseased part 7. This operation mode A allows the patient's diseased part 7 to be identified and an initial plan for therapy to be made.

The operation mode B is carried out next. The switch 13 is set to the B position. In the operation mode B, both the therapeutic transducer 2 and the imaging probe 16 are driven. Ultrasonic waves for intensity distribution are generated from the ultrasonic transducer 2 according to the first sync signal. Ultrasonic waves for imaging are generated by the imaging probe 16 upon lapse of a specific time from the leading edge of the second sync signal.

As shown in FIG. 3, the propagation path of the ultrasonic waves for intensity distribution differs from that of the ultrasonic waves for imaging. Therefore, the timings of generating these two sets of ultrasonic waves must be adjusted, so that echoes of the ultrasonic waves for intensity distribution reflected from the focus and echoes of the ultrasonic waves for imaging reflected from the focus will arrive at the imaging probe 16 at the same time. As shown in FIG. 4, ultrasonic pulses for diagnostic from probe 16 imaging are emitted after a time interval on the basis of the sound sync signal. Ultrasonic pulses for intensity distribution imaging from transducer 2 are synchronized with the first sync signal which is delayed by a specific time interval dt with respect to the second sync signal. This pulse sequence makes the pulses from probe 16 to be emitted when the pulses from transducer 2 transverse the emitting surface of probe 16.

The echoes of the ultrasonic waves for intensity distribution and the echoes of the ultrasonic waves for imaging are received by the imaging probe 16. The echoes of the ultrasonic waves for intensity distribution contain many low-frequency components corresponding to the first fundamental frequency f1. The echoes of the ultrasonic waves for imaging contain many high-frequency components corresponding to the second fundamental frequency f2.

As described previously, the piezoelectric transducer elements of the imaging probe 16 are highly sensitive to both the first fundamental frequency f1 of the ultrasonic waves for intensity distribution imaging and the second fundamental frequency f2 of the imaging ultrasonic waves. On the other hand, the piezoelectric transducer elements of the conventional imaging probe are highly sensitive to the second fundamental frequency f2 of the imaging ultrasonic waves but are insensitive to the first fundamental frequency f1 of the ultrasonic waves for intensity distribution imaging. In the prior art, therefore, high-frequency components contained in echoes of ultrasonic waves for intensity distribution are used mainly for intensity distribution imaging, and the image had but a low S/N ratio. The high-frequency components are emphasized by non-linearity of the propagation of ultrasonic waves. Note that the quality of intensity distribution imaging is improved by increasing the intensity of ultrasonic waves for intensity distribution imaging. However, increasing the intensity of ultrasonic waves for intensity distribution imaging is not preferable because there arises the likelihood that it will promote the generation of cavitation at the focus and shock waves produced at the time of its collapse will cause not a little damage to tissues in the focus region. In contrast, in the present embodiment, the piezoelectric transducer elements of the imaging probe 16 are arranged to be highly sensitive to the first fundamental frequency f1 of the ultrasonic waves for intensity distribution imaging and the second fundamental frequency f1 of the imaging ultrasonic waves. Consequently, the damage to tissues can be suppressed as much as possible and the degradation in the time resolution can be avoided to improve the quality of an intensity distribution image and a tomographic image. The intensity distribution imaging quality can also be improved by gain adjustment in a direction to increase the reception sensitivity. In this case, at least one gain adjusting circuit is provided in the path connecting the echo filter 21 and the B-mode processing unit 22 (FIG. 2). (Preferably, one gain adjusting circuit is provided in each path.)

The received signal output from the receive delay circuit 20, which is produced by delaying echo signals on the respective channels by different amounts and then summing them, is applied to the echo filter 21. The received signal has mainly low-frequency components corresponding to the first fundamental frequency f1 of the ultrasonic waves for imaging intensity distribution and high-frequency components corresponding to the second fundamental frequency f2 of the ultrasonic waves for tomography. The highpass filter 30 in the echo filter extracts the high-frequency components, while the lowpass filter 31 extracts the low-frequency components. The high-frequency processing circuit 32H produces a tomographic image from the high-frequency components, while the low-frequency processing circuit 32L produces an intensity distribution image from the low-frequency components. The low-frequency processing circuit 32L may extract an area of pixels which exceed a predetermined threshold value in the intensity distribution as the actual focus, in which case only the actual focus will be displayed.

Since the low-frequency components and the high-frequency components are processed separately in this manner, a first gain and a second gain can be applied to the low-frequency components and the high-frequency components, respectively, to implement suitable STC for the respective components. This is due to the fact that the ultrasonic attenuation factor depends on frequency.

Next, in the operation mode C, therapeutic ultrasonic waves that are stronger than the intensity distribution ultrasonic waves are generated continuously from the ultrasonic transducer 2 for the purpose of treatment of the diseased part.

In general, the higher the frequency of an ultrasonic wave from the ultrasonic transducer 2 is, the closer it is focused to the focus. Therefore, in the prior art case where the intensity distribution is imaged on the basis of high-frequency components contained in echoes of ultrasonic waves for imaging intensity distribution, the focus region would be displayed smaller than actual. This is not desirable. In contrast, in the present embodiment, the intensity distribution is imaged on the basis of low-frequency components (corresponding to the first frequency f1) contained in echoes of ultrasonic waves for imaging intensity distribution, allowing an intensity distribution faithful to the actual intensity distribution to be obtained. This increases the reliability of quantitative evaluation, permitting presumption of a heating region based on the intensity distribution to be performed with high precision.

Second Embodiment

Figure 5:
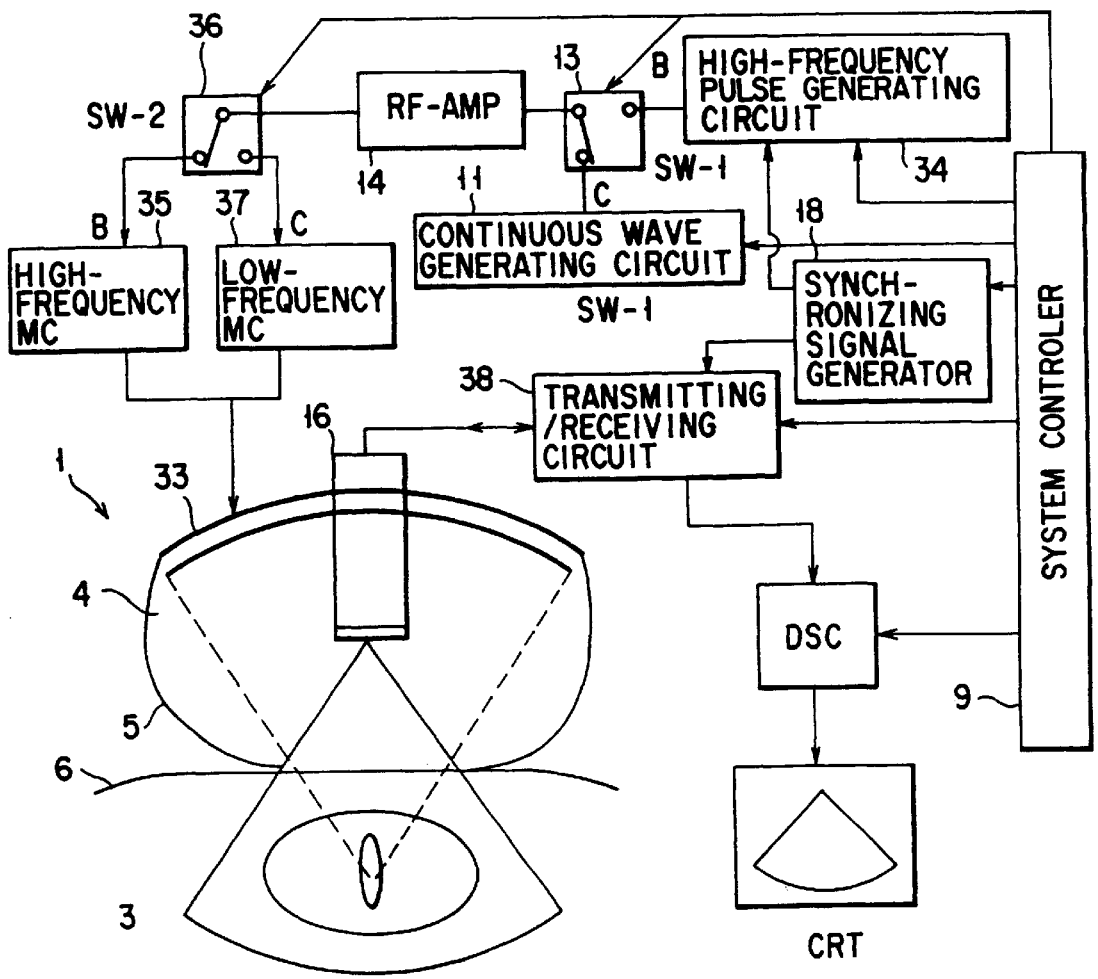
FIG. 5 shows an arrangement of an ultrasonic therapeutic apparatus according to a second embodiment of the invention.

FIG. 5 shows an arrangement of an ultrasonic therapeutic apparatus according to a second embodiment of the invention. In this figure, like reference numerals are used to denote corresponding parts to those in FIG. 1 and description thereof is omitted.

A therapeutic ultrasonic transducer 33 uses piezoelectric transducer elements having a peak of sensitivity to a first fundamental frequency f1 corresponding to therapeutic ultrasonic waves and a second fundamental frequency f2 corresponding to in vivo imaging ultrasonic waves. The transducer is implemented by the two-layer structure or hybrid structure as described previously.

A high-frequency pulse generator 34 generates periodically signal pulses of the second fundamental frequency f2, which are applied through the switch 13, the RF amplifier 4, a switch 36, and a high-frequency matching circuit 35 to the piezoelectric elements of the ultrasonic transducer 33. Thus, ultrasonic waves for imaging intensity distribution are generated periodically. The continuous wave generator 11 generates continuously a continuous signal of the first fundamental frequency f1, which is applied through the switch 13, the RF amplifier 4, the switch 36, and a low-frequency matching circuit 37 to the piezoelectric transducer elements of the ultrasonic transducer 33. Thereby, therapeutic ultrasonic waves are generated continuously.

The same operation is performed by the system controller 9. At the time of the operation mode B in which the intensity distribution is imaged, both the switches 13 and 36 are set to the B position. At the time of the operation mode C in which treatment is performed actually, the switches 13 and 36 are both set to the C position.

In the operation mode B, the transducer 33 is driven with the second fundamental frequency f2. Ultrasonic waves for imaging intensity distribution are generated from the transducer 33 in a frequency band centered at the first fundamental frequency f2. Echoes of those ultrasonic waves contain many high-frequency components corresponding to the second frequency f2.

The imaging probe 16 has a high sensitivity to the second frequency f2.

Accordingly, the second embodiment provides the same advantages as the first embodiment.

Third Embodiment

FIG. 6 shows an arrangement of an ultrasonic therapeutic apparatus according to a third embodiment of the invention. In this figure, like reference numerals are used to denote corresponding parts to those in FIG. 1 and description thereof is omitted.

An ultrasonic diagnostic unit 40 includes an STC, a log amplifier, a detector, and an analog-to-digital converter, as does the B-mode processing unit of FIG. 1. The diagnostic unit 40 further includes a frequency information analyzer 41 for obtaining frequency information.

As with the first embodiment, in the present embodiment, the time of generating ultrasonic waves for imaging intensity distribution from the source 2 and the time of generating ultrasonic waves for ultrasonic imaging from the probe 16 are adjusted so that both the ultrasonic waves will arrive at the focus simultaneously.

The present embodiment is intended to improve the precision of this simultaneity.

A temperature sensor 42 is provided for measuring the temperature of the coupling liquid 4. A computation unit 44 computes the velocity of ultrasonic waves within the coupling liquid on the basis of the measured temperature of the coupling liquid. A position sensor 43, implemented by a rotary encoder by way of example, is provided for measuring the difference between the distance from the surface of the piezoelectric elements of the ultrasonic transducer 2 to the focus and the distance from the surface of the piezoelectric elements of the probe 16 and the focus.

The system controller 9 compensates for the phase difference (time interval A) between the first and second sync signals on the basis of the computed velocity of ultrasonic waves and the measured distance difference.

Thus, the precision of simultaneity of the arrival of the ultrasonic waves from the transducer 2 and the ultrasonic waves from the probe 16 at the focus is improved.

Figure 7:
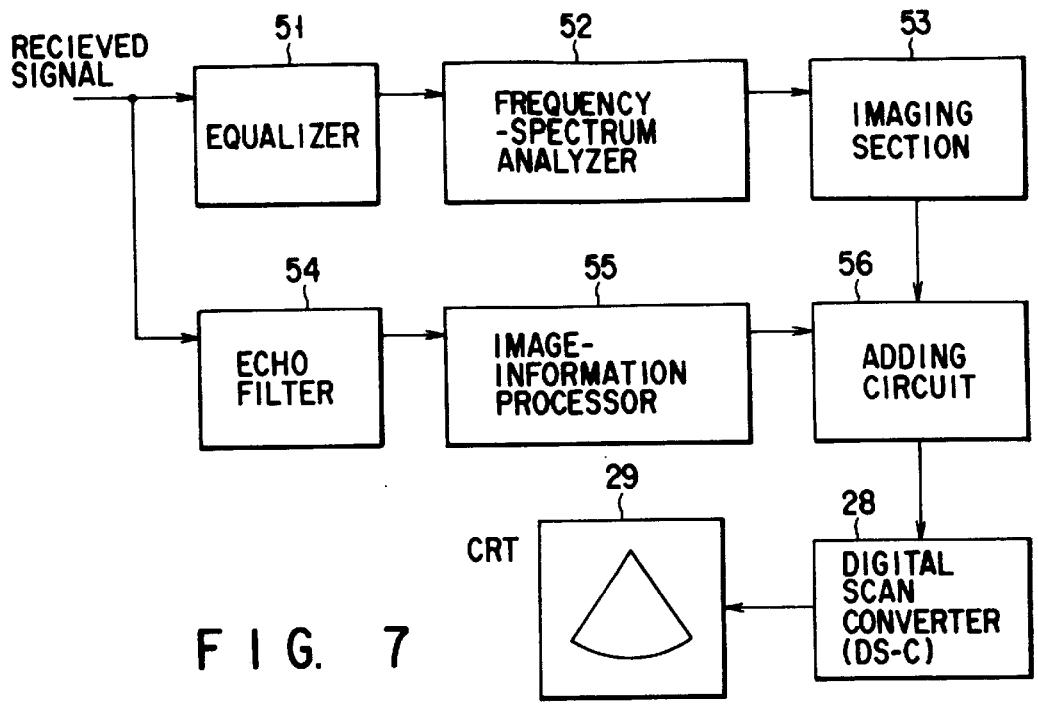
FIG. 7 is a block diagram of the ultrasonic diagnostic section of FIG. 6.

FIG. 7 shows an arrangement of the frequency information analyzer 41 of FIG. 6. The piezoelectric elements of the probe 16 have resonant characteristics by which they are highly sensitive to the second fundamental frequency f2.

This is equivalent to a highpass filter which attenuates low-frequency components that are contained in echoes of ultrasonic waves for imaging intensity distribution in great numbers and correspond to the first fundamental frequency f1. An equalizer 51 for compensating for this filter characteristic is provided to precede a frequency spectrum analyzer 50.

Figure 8:
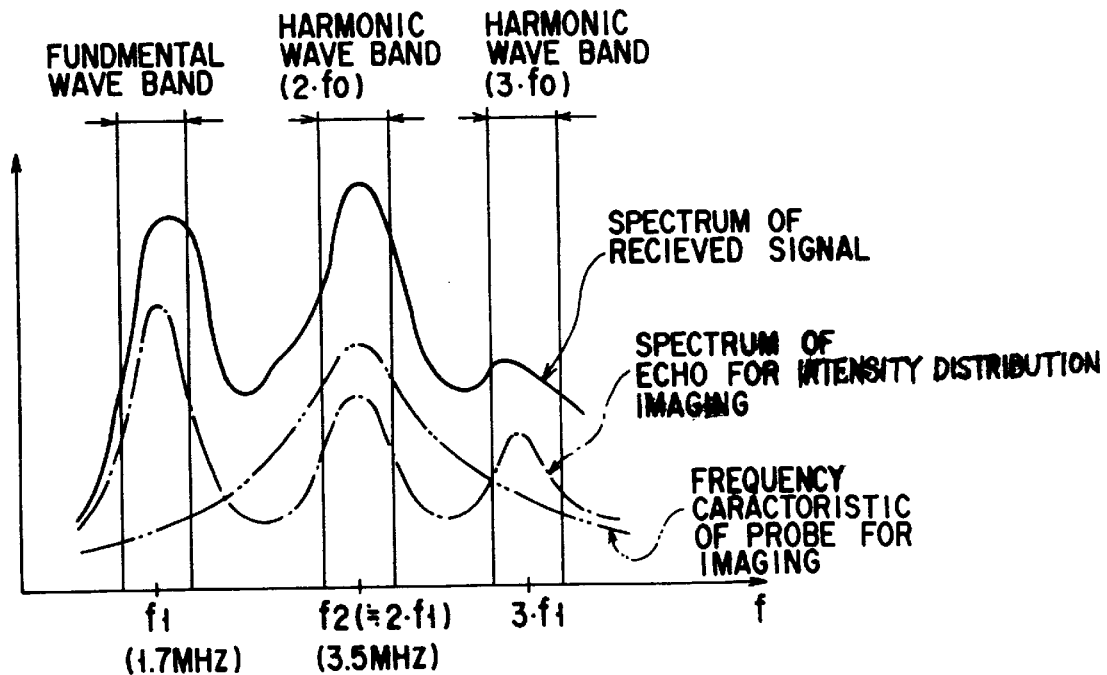
FIG. 8 shows a received signal spectrum.

The function of the equalizer 51 will be described with reference to FIG. 8. The spectral characteristic of echoes of ultrasonic waves for imaging intensity distribution is high in the fundamental frequency band centered at the first frequency f1 and harmonic frequency bands each centered at a frequency that is an integral multiple of the first frequency f1 (n×f1). The sensitivity characteristic of the probe 16 is high at the second fundamental frequency f2. The spectrum of the received signal by the probe 16 is represented as a product of the frequency spectrum of echoes of ultrasonic waves for imaging intensity distribution and the frequency characteristic of the probe 16. The equalizer 51 shapes the received signal spectrum so as to approximate to the echo spectrum.

The frequency spectrum analyzer 52 performs fast Fourier transform on the received signal from the equalizer 51 to produce its spectrum and obtain the area of a specific band. This process is performed on multiple points to produce the spatial distribution of ultrasonic energy. The specific band is the fundamental frequency band, the harmonic frequency band, or both. An imaging unit 53 assigns hue or brightness to each point in the intensity distribution according to its magnitude.

An echo filter 54 is a bandpass filter which passes high-frequency components in the high frequency band centered at the second fundamental frequency f2. An image information processing unit 55 produces a tomographic image (B-mode image) on the basis of the high-frequency components passed through the echo filter 54.

An adder 56 superposes the spatial distribution image of ultrasonic energy with the tomographic image on a frame-by-frame basis.

The frequency spectrum analyzer 52 may compute the extent to which a spectrum broadens (the extent of dispersion) for multiple points to obtain the spatial distribution of the dispersion of that spectrum. The higher the intensity of therapeutic ultrasonic waves at each point, the more the high-frequency components are generated at that point. Thus, the spatial distribution of the dispersion approximates to the intensity distribution. In addition, in the frequency spectrum analyzer 52, the position of center of gravity of the spectrum may be sought for multiple points.

The system controller 9 presumes the temperature distribution from the intensity distribution thus obtained. Tissues present at the focus of the therapeutic ultrasonic waves are heated and necrotized. The temperature depends on the ultrasonic wave absorption factor and the thermal conductivity of the tissues, the intensity of the therapeutic ultrasonic waves, the application time, etc. The absorption factor and the thermal conductivity are entered by an operator through the console 10. The absorption factor and the thermal conductivity are selectively read from a memory 45 which stores the ultrasonic wave absorption factor and the thermal conductivity for each of body regions (organs). The absorption factor may be sought by calculations on the basis of a received signal. That is, a comparison, in intensity between echoes reflected in front of the focus and echoes reflected from the focus is first made. The ultrasonic wave attenuation factor is next calculated on the basis of the result of that comparison and the diffusion parameter of ultrasonic waves dependent on the propagation distance. Finally, the ultrasonic wave absorption factor is calculated on the basis of the attenuation factor. The intensity of the therapeutic ultrasonic waves is obtained from the intensity distribution. The time of application of ultrasonic waves is set by the operator.

The system controller 9 applies the absorption factor, the thermal conductivity, the intensity of the therapeutic ultrasonic waves, and the irradiation time to the heat transport equation to presume the temperature quantitatively. This presumption is performed on multiple points in the vicinity of the focus. Thereby, the spatial distribution of the presumed temperatures, i.e., the temperature distribution, is produced. The temperature distribution is displayed superimposed on a tomographic image of tissues on the CRT 29. An area that is at temperatures above the temperature at which cancer cells thermally affected and necrotize (i.e., treated region at about 50 to 60° C. or more) may be extracted from the temperature distribution and displayed encircled by a continuous or dotted line, colored, or halftone dot meshed. The operator can predict regions that will be thermally metamorphosed, regions that will suffer damage, etc., on the basis of the temperature distribution.

It is possible for the system controller 9 to make a plan for therapy for a diseased part the region of which has been specified on a tomographic image by the operator. The system controller 9 recognizes the region of that diseased part as comprising a predetermined number of subregions. The intensity of ultrasonic waves at the focus and the application time are determined by the system controller so that the therapy for one subregion will be completed in a single operation. The treating region is enlarged/reduced taking the ultrasonic wave absorption factor and the thermal conductivity into consideration while the intensity at the focus and the application time are being changed. The intensity at the focus and the application time for the treating region when it coincides with a subregion are selected.

Further, with the present embodiment, it is possible to seek drive energy required to obtain the intensity of therapeutic ultrasonic waves at the focus (first focus intensity) that is necessary for therapy, i.e., the magnitude of a drive signal to be applied to the second piezoelectric transducer elements of the therapeutic ultrasonic transducer. This is due to the fact that, in the present invention, the intensity at the focus can be measured quantitatively. The drive energy (second drive energy) at the time of imaging of intensity distribution and the resulting intensity at the focus (second focus intensity) are stored in the memory 45. There is a substantially proportional relationship between the focus intensity and the drive energy. Thus, the first drive energy is calculated by multiplying the second drive energy and the result of division of the first focus intensity by the second focus intensity. This calculation is performed by the system controller 9. The first focus intensity can be obtained by producing a drive signal according to the first drive energy thus obtained.

Figure 9:
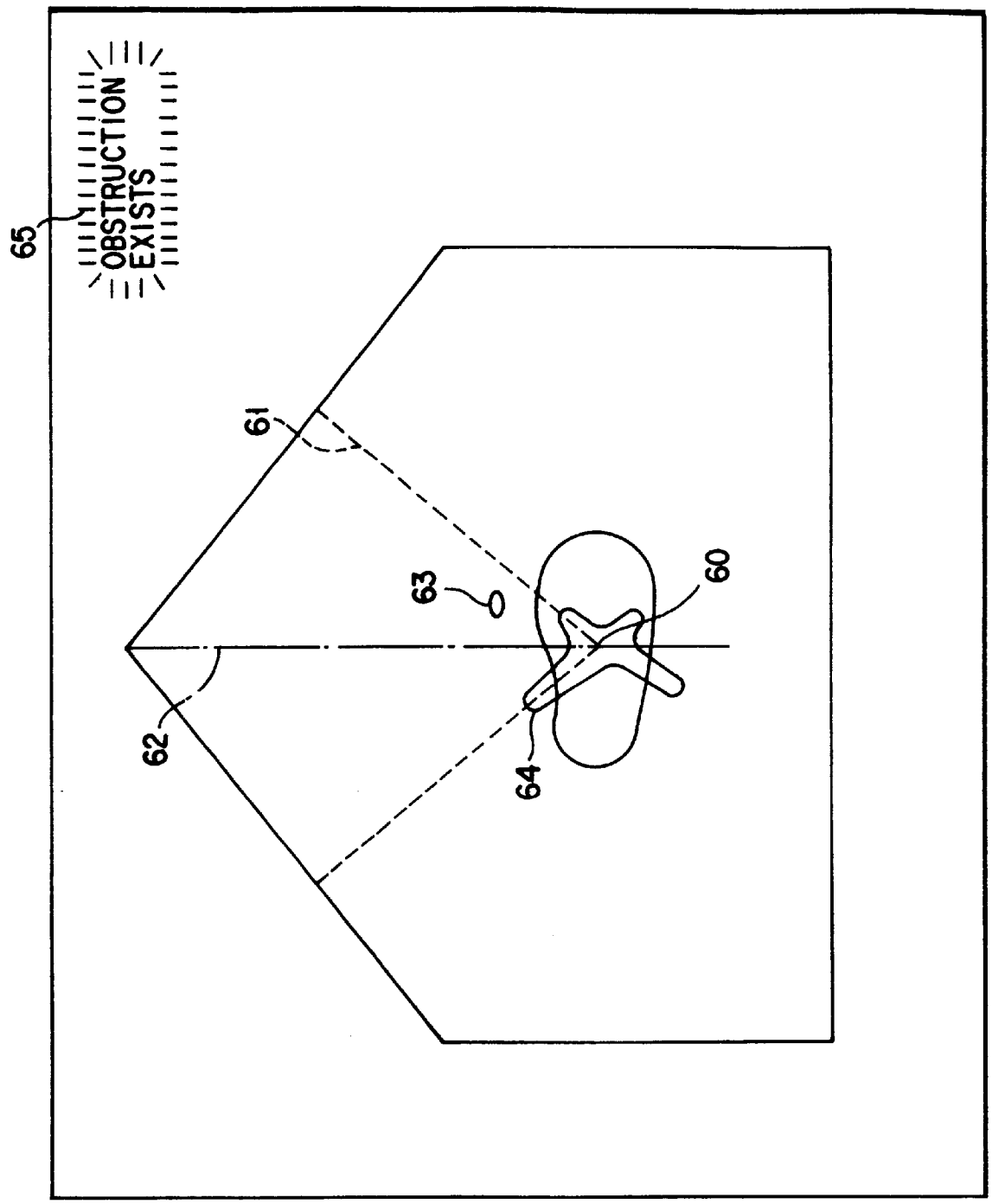
FIG. 9 shows a display image on the CRT of FIG. 7.

FIG. 9 shows the intensity distribution when there is an object that may well reflect ultrasonic waves, on the propagation paths of therapeutic ultrasonic waves. When such an object is present on the propagation path of ultrasonic waves, the intensity the waves have at the focal point is low. The object may be a bone which generates heat. The detection of the object is clinically important. In FIG. 9, the therapeutic ultrasonic waves propagate through the living body along paths 61 toward the focus 60. When a wave-reflecting object 63 is off the central axis 62 in the propagation paths 61 of ultrasonic waves, the intensity distribution 64 is distorted and gets out of bisymmetry as shown in FIG. 9. The same is true of the case where an ultrasonic wave absorber is present. One reason for the distorted distribution is that part of therapeutic ultrasonic energy is prevented from reaching the focus by the object 63. The intensity distribution is distorted not only when a wave-reflecting object is present on a two-dimensional imaging plane but also when it is present within a conical space through which therapeutic ultrasonic waves propagate. The operator can determine whether such an object or a wave absorber is present or not on the propagation paths of therapeutic ultrasonic waves on the basis of the shape of the intensity distribution 64. Alternatively, the system controller 9 may determine the presence or absence of a heated region or a wave absorber on the basis of the result of comparison between the shape of the measured intensity distribution and a previously specified shape or the bisymmetric property of the intensity distribution shape. When the presence of an obstacle is recognized, the system controller displays a system warning message 65 on the CRt 29 and makes a beep in order to inform the operator of the presence. In addition, the system controller operates a safeguard which forcibly disables the start of therapy.

Such a safeguard can also be provided by measuring the intensity of ultrasonic waves in the focus region. With this approach, an advantage can be expected even when a wave-reflecting object or wave absorber is present in a plane that passes through the central axis of a two-dimensional imaging plane and is perpendicular to that plane. As described previously, the energy in the focus region can be predicted from the second drive energy of the piezoelectric transducer elements. At this point, the energy in the focus region could be predicted more accurately by taking into consideration the ultrasonic wave attenuation factor within the living body. The intensity of ultrasonic waves in the focus region thus predicted is compared with the actually obtained intensity of ultrasonic waves in the focus region. If the difference is greater than the preset value, then it is considered that part of ultrasonic energy may be scattered by a strong reflector (or a strong absorber) before reaching the focus. In such case, the system controller informs the operator of the occurrence of abnormality as described previously. Alternatively, a safeguard that responds to such information to disable the start of therapy may be incorporated into the system.

Moreover, the system controller 9 determines the presence or absence of displacement of propagation paths of therapeutic ultrasonic waves due to refraction on the basis of the intensity distribution. In the presence of displacement, the system controller issues an warning. When the displacement is in the two-dimensional imaging plane, it can be recognized visually from the distortion of the intensity distribution. However, when the displacement is offset from the two-dimensional imaging plane, it cannot be recognized visually. The system controller makes a comparison between the actual focus intensity and the predetermined intensity calculated from the drive energy and, when the difference is not within a predetermined range, decides that the propagation paths of the therapeutic ultrasonic waves have been displaced. The system controller then informs the operator of this fact.

When the difference between the actual focus intensity and the predetermined intensity lies within a predetermined allowable range, the system controller issues a message that treatment is executable.

Next, a method of suppressing the effect of the intensity distribution imaging on a living body and improving the frame rate will be described below. The acoustic energy of the ultrasonic waves for intensity distribution imaging is made lower than that of the therapeutic ultrasonic waves and hence considered to have relatively little effect on the living body. If the number of rasters is decreased by narrowing the range of intensity distribution imaging scan to the extent that involves at least the neighborhood of the geometrical focus, then the effect on the living body can be weakened because the number of applications of the ultrasonic waves for intensity distribution imaging corresponding to one frame is decreased. Even if the scan for tomographic imaging and the scan for intensity distribution imaging are made alternately, the frame rate can be improved by narrowing the range of the intensity distribution imaging scan to thereby decrease the number of rasters. On the other hand, even if the display area of an intensity distribution image is narrowed, it has no important effect on the intensity distribution imaging because the therapeutic ultrasonic waves propagate through a region that is narrow in comparison with that for normal in vivo imaging. The switching between scan ranges is made under the control of the system controller in response to entry of a switching command by the operator into the system controller through the console 10. Further, display switching may be performed before treatment and at treatment time. For example, intensity distribution imaging is performed in full-screen before therapy and the intensity distribution imaging region is narrowed or restricted to only the focus region after the safety on the propagation paths of ultrasonic waves has been confirmed.

Fourth Embodiment

Figure 10:
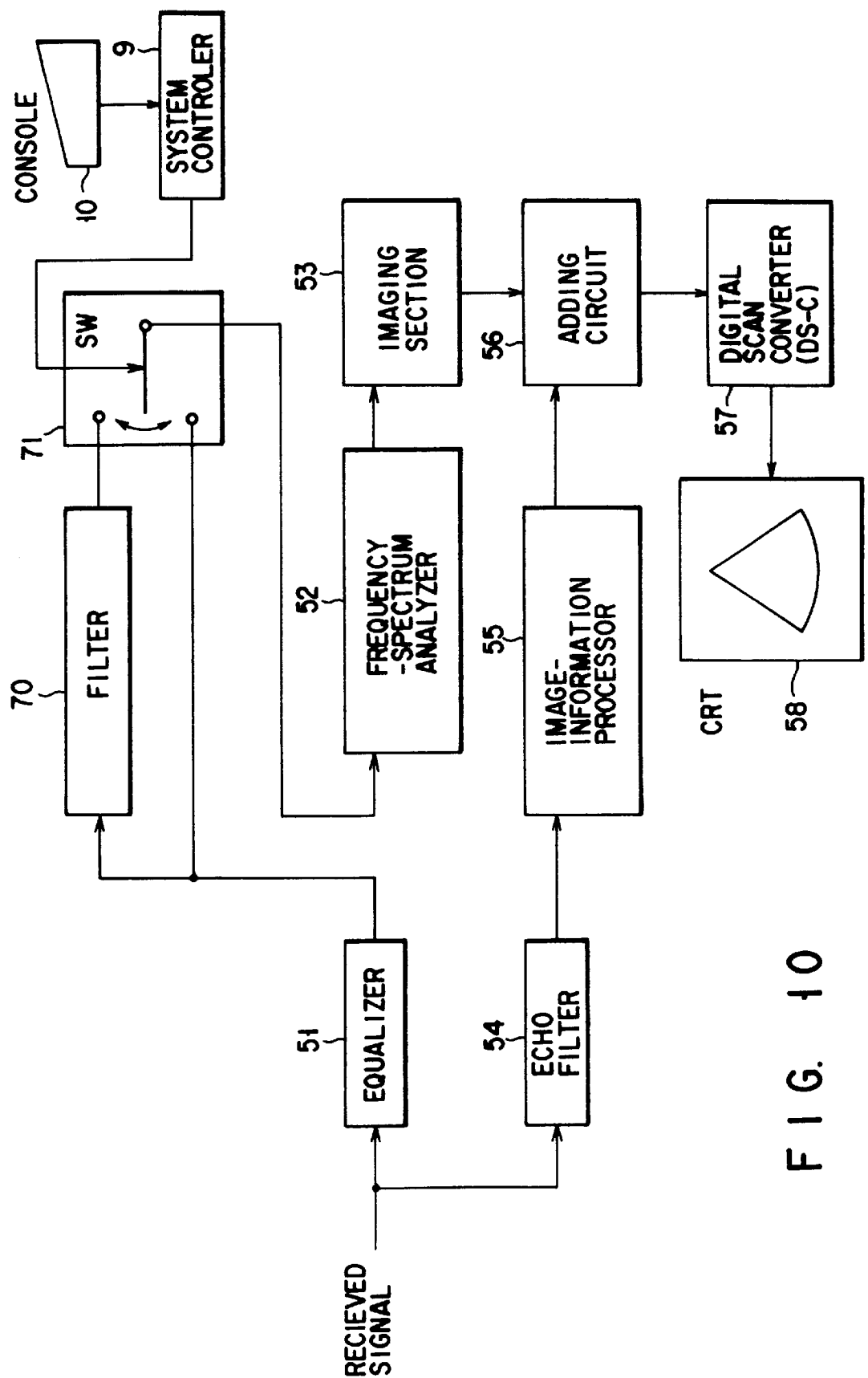
FIG. 10 shows an arrangement of an ultrasonic therapeutic apparatus according to a fourth embodiment of the invention.
Figure 11:
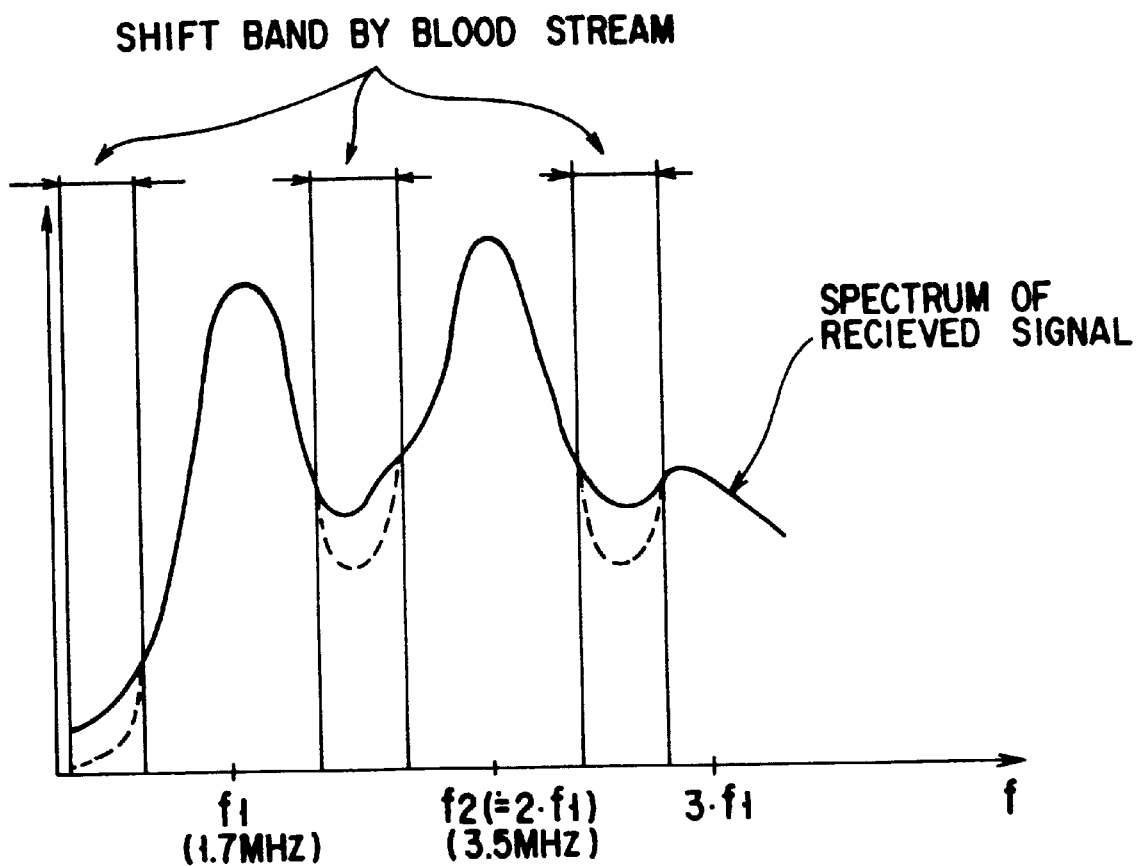
FIG. 11 shows blood-flow-shifted bands.

FIG. 10 shows an arrangement of a principal part of an ultrasonic therapeutic apparatus according to a third embodiment of the invention. In FIG. 10, like reference numerals are used to denote corresponding parts to those in FIG. 7 and description thereof is omitted. A filter 70 is provided to precede the frequency spectrum analyzer 52 with a switch 71 interposed therebetween. The filter is intended to remove chiefly blood-flow-shifted components from a received signal. The blood-flow Doppler effect shifts the frequency of ultrasonic waves by about several kilohertzs. As shown in schematically FIG. 1, the shift bands in which a shift occurs are defined as bands centered at frequencies that are several kilohertzs above and below the first fundamental frequency f0 and bands centered at frequencies that are several kilohertzs above and below the second fundamental frequency f2.

The filter 70 sufficiently attenuates or remove the shifted components within these shift bands. The filter is constructed from a plurality of highpass filters and a plurality of lowpass filters. The filter need not limited to this arrangement as long as it has a function of sufficiently attenuating the shifted components within the shift bands. The shifted components that are slightly offset from the fundamental frequencies are removed by the filter 70. The ultrasonic waves for in vivo imaging and the ultrasonic waves for intensity distribution imaging are 1 MHz or more apart from each other and contain harmonic components to cover a very broad range. Thus, even if the shifted components are removed, the signal intensity will not be decreased extremely, thus keeping high image quality. The adjustment of bands that the filter 70 eliminates permits shifted components resulting from moving objects, such as heart walls, other than blood flow to be eliminated.

The switch 71 selects between elimination and non-elimination of the shifted components. The switch is changed over by a command entered by the operator into the system controller 9 via the console 10.

Fifth Embodiment

Figure 12:
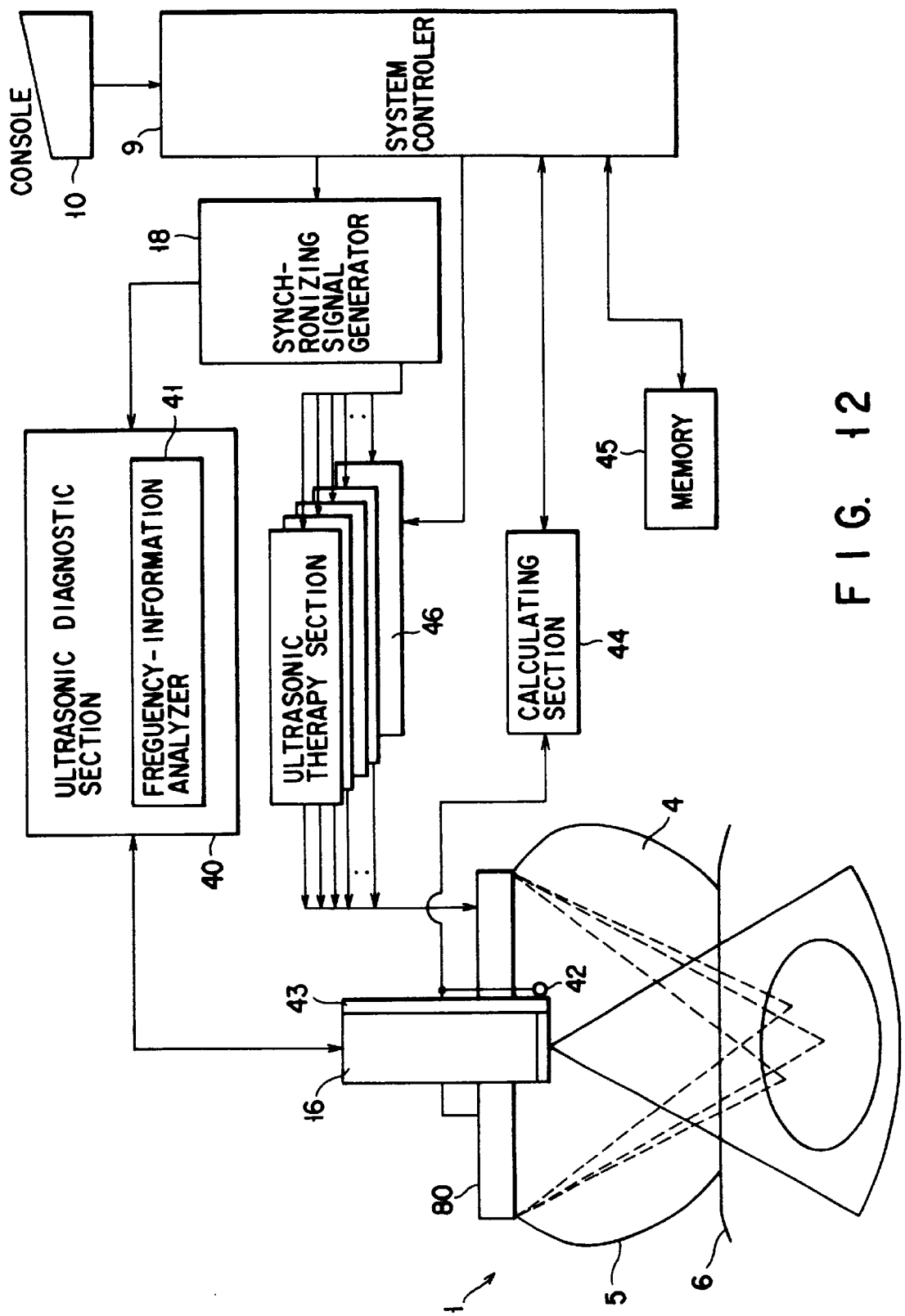
FIG. 12 shows an arrangement of an ultrasonic therapeutic apparatus according to a fifth embodiment of the invention.

FIG. 12 shows an arrangement of an ultrasonic therapeutic apparatus according to a fifth embodiment of the invention. In this figure, like reference numerals are used to denote corresponding parts to those in FIG. 6. A therapeutic ultrasonic transducer 80 is arranged, as shown in FIG. 13, such that a piezoelectric transducer element 81 in the form of a disk is divided in the direction of radius and in the direction of circumference. In other words, the transducer 89 is arranged such that a plurality of piezoelectric elements 81 are arranged in the form of a disk. A single piezoelectric element 81 is described herein as forming one channel. Of course, a plurality of adjacent piezoelectric elements may form one channel.

A plurality of ultrasonic therapeutic sections 46 are provided each of which comprises a matching circuit, an RF amplifier, a continuous wave generator, a pulse generator, and a switch circuit for switching between the continuous wave generator and the pulse generator. The piezoelectric elements 81 and the ultrasonic therapeutic sections 46 are connected in a one-to-one relationship so as to permit the piezoelectric elements 81 to be driven independently for each channel. The synchronization circuit 18 provides the ultrasonic therapeutic sections 46 with sync signals of different phases so that ultrasonic waves generated from the piezoelectric elements 81 will converge onto the focus. A point at a predetermined depth on the perpendicular from the central point of the piezoelectric element disk is referred to as the reference focus. The focus associated with standard sync signals corresponds with this reference focus.

Under the control of the system controller 9, the synchronization circuit 18 is permitted to change the phases of the sync signals applied to the ultrasonic therapeutic sections 46, The changes in the phase of the sync signals permits the focus to be shifted from the reference focus to another position. At the time the focus is shifted from the reference focus, the acoustic pressure at a new focus changes from that at the reference focus. In order to compensate for changes in acoustic pressure, the system controller 9 controls the RF amplifiers in the ultrasonic therapeutic sections 46 to thereby adjust the amplitude of the drive signals.

Consider here that the focus of the therapeutic ultrasonic waves is displaced from the set point by refraction by way of example. The ultrasonic pulses for intensity distribution and the ultrasonic waves for imaging may be refracted to different extents.

This is because these sets of waves differ in propagation path and propagation angle to living tissues. The difference in refraction is not so grate since both sets are of ultrasonic waves. In focal depth, the lateral difference is in several millimeters.

The system controller 9 then performs the following operations. The focus of the ultrasonic waves for intensity distribution imaging is shifted from the initial point. The position of the focus of the ultrasonic waves for intensity distribution imaging is changed spirally within a sphere of a radius of several millimeters centered at the position of a diseased part. The reflecting waves of the ultrasonic pulses for the intensity distribution from the focal point in the image is detected, and the intensity of the reflected waves derived from the waves for imaging is measured. The maximum intensity of a wave reflected at each focal point is selected and then compared with the presumed focus intensity to determine whether or not the difference lies within the allowable range. When the difference lies within the allowable range, the treatment can be initiated with delay control corresponding to the maximum intensity. The diffraction of the ultrasonic pulses for imaging the intensity distribution is thereby made equal to the diffraction of the ultrasonic pulses for imaging. On the other hand, when the difference is not within the allowable range, an warning is issued and the initiation of treatment is disabled.

A frequency information analyzer 41 measures a maximally heated region on the basis of the intensity distribution. The maximally heated region is spatially offset slightly from the focus. In echoes of ultrasonic waves for intensity distribution imaging are contained not only the fundamental frequency component but also harmonic components, which are signal components within harmonic frequency bands as shown in FIG. 14. The harmonic frequency bands are bands each of which is centered at an integral multiple of the first fundamental frequency f1 of the ultrasonic waves for intensity distribution imaging and the therapeutic ultrasonic waves. The more the waveform of ultrasonic waves is distorted, the higher the acoustic pressure becomes. The waveform distortion produces harmonic components. That is, a portion which contains many harmonic components corresponds to a region in which the acoustic pressure level is great. This region can be presumed to be one where heat is probably heated. The frequency information analyzer 41 extracts harmonic components from the received signal. The intensity distribution is produced on the basis of the extracted harmonic components. The region which exceeds a predetermined intensity level in the intensity distribution is extracted as the maximally heated region. The delay control is adjusted so that the position of the maximally heated region matches the position of the diseased part.

Suppose here that the maximally heated region 103 is displaced from a diseased part 102 as shown in FIG. 15. In this example, a three-dimensional ultrasonic image is produced. Techniques of producing three-dimensional ultrasonic images are well known as disclosed in Japanese Unexamined Patent Publications Nos. 61-209643 and 5-300910 and hence description thereof is omitted herein. On the CRT 29 are displayed a three-dimensional ultrasonic image, three-dimensional coordinate axes 101, the diseased part 102, and three-dimensional coordinates 104 representing the maximally heated region 103. This three-dimensional coordinate system is such that its origin (0, 0, 0) is placed at a point 105 on the three-dimensional image. Suppose that the cordinates of the diseased part 102 are (0, 8, 0) and the coordinates of the maximally heated region 103 (−1, 6, 0). On the basis of spatial displacement of the maximally heated region 103 with respect to the diseased part 102, the system controller 9 controls the synchronization circuit 18, so that intensity distribution imaging is carried out with delay control adjusted. This operation is repeated until coordinate matching is achieved between the maximally heated region 103 and the diseased part 102. When the coordinate matching is effected, treatment is initiated under the delay control at that time.

As shown in FIGS. 16A and 16B, the extracted maximally heated region 103 and the focus may be displayed by a square marker 110a and a round marker 110b, respectively, so that they can be distinguished from each other. Alternatively, they may be distinguished by colors. Further, as shown in FIG. 16C, a marker 110c may be displayed to represent intensity variations in the intensity distribution produced on the basis of harmonic components by color variations, variations in color deepness, brightness variations, or contour lines.

Although the focus of therapeutic ultrasonic waves is indicated as the maximally heated region, the intensity of ultrasonic waves may be obtained by calculations using the same principle. In this case, the wave intensity is divided into multiple levels and displayed by a graphic symbol or a color for each level. This approach is effective not only in making the purpose of irradiation definite but also in making sure the target intensity of ultrasonic waves is obtained or the apparatus is in normal operation. The differences may be displayed by different types of lines, such as a solid line, a dotted line, etc.

Sixth Embodiment

FIG. 17 shows an arrangement of an ultrasonic therapeutic apparatus according to a sixth embodiment of the invention. In this figure, like reference numerals are used to denote corresponding parts to those in FIGS. 1 and 12. A number of piezoelectric transducer elements constituting a therapeutic ultrasonic transducer 2 can each be driven individually by a corresponding driver 120. Drivers 120 are connected the system controller 9 and a driving power supply 121 and responsive to control signals from the system controller to apply a drive signal to a corresponding one of the piezoelectric elements.

Treatment for calculus will be described herein. In order to focus therapeutic ultrasonic waves onto a calculus, a diseased part (calculus) is first determined on an ultrasonic image reconstructed by the ultrasonic image diagnostic section 40 on a received signal acquired by the imaging probe 16. The position of the diseased part is entered by the operator via the console 10. The coordinates of the diseased part are calculated by the system controller 9. On the calculated coordinates of the diseased part, the system controller 9 calculates the difference in drive timing among the piezoelectric elements, i.e., delay times associated with the respective piezoelectric elements, so that the therapeutic ultrasonic waves will be focused on the diseased cart. The entry of the position of the diseased part may be made by an automatic detection and entry system as disclosed in Japanese Patent Application No. 4-261420.

Conventionally, the delay times of the drive signals to the piezoelectric transducer elements are calculated on the premise that the process of ultrasonic wave propagation has linearity. The therapeutic ultrasonic waves (shock waves) that are so strong as to break a calculus are subject to a great effect of nonlinearity in process of propagation. According to the conventional method of calculation, therefore, the actually formed focus will deviate from the position of the focus obtained by calculation. This deviation is not large on the reference line dropped vertically from the central point of the therapeutic ultrasonic transducer 2, but is large at any point off the reference line. The deviation is inevitable because the distance to the focus offset from the reference line differs from piezoelectric element to piezoelectric element.

Figure 18:
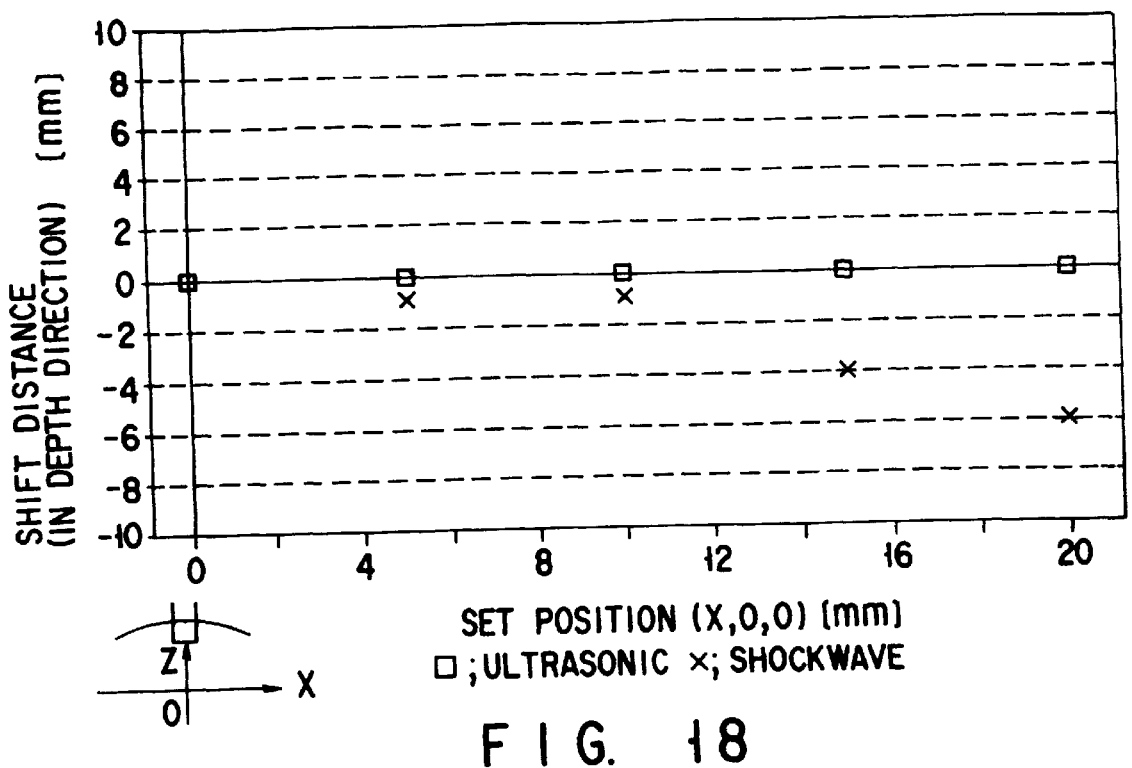
FIG. 18 shows changes in deviation between the calculated focus position and the actual focus position in the phased array technology.

FIG. 18 shows variation in amount of deviation relative to variations in distance between the axis (Z line) and the calculated focus. The deviation on the side near the therapeutic ultrasonic source is represented by positive, and the deviation on the side remote from the source of waves is represented by negative. For normal in vivo imaging ultrasonic waves, there is little deviation (□). For therapeutic ultrasonic waves much stronger than the imaging ultrasonic waves (shock waves), the deviation (x) increases with increasing distance between the reference position and the focus. This is because the effect of nonlinearity occurring in process of propagation of ultrasonic waves increases with the displacement of the propagation distance to said preset position according to the displacement, from the reference time.

In the present embodiment, the coordinates of the diseased part are corrected on the basis of the amount of deviation. The delay times associated with the piezoelectric elements are calculated as conventional so that the focus will be formed in the corrected coordinate position. Thereby, the focus of the therapeutic ultrasonic waves can be matched to the diseased part with high precision. In the memory 45 there are stored the distance from the reference line, the intensity of ultrasonic waves (magnitude of drive signals), and the amount of deviation in combination. The system controller 9 seeks the distance between the position of a specified diseased part and the reference line, reads the amount of deviation corresponding to the distance and the intensity of ultrasonic waves (magnitude of drive signals) from the memory 45, corrects she position of the diseased part according to the amount of deviation, and calculates the delay times associated with the piezoelectric elements so that the focus will be formed in the corrected position. In addition, the memory 45 may store the distance from the reference line, the intensity of ultrasonic waves, and correction values for delay times corresponding to the amount of deviation in combination. In this case, the delay times calculated as conventional for the piezoelectric elements are corrected according to the correction values so that the ultrasonic waves will be focused onto the diseased part.

The focus is not a point but formed to have some size. Thus, the possible focus position may be set discrete taking into consideration the focus size.

Instead of the amounts of deviation and the correction values being stored in the memory 45, they may be calculated by the system controller 9 according to the distance from the reference line and the ultrasonic wave intensity.

Seventh Embodiment

FIG. 19 shows an arrangement of a tracking type of ultrasonic therapeutic apparatus according to a seventh embodiment of the invention. In this figure, like reference numerals are used to denote corresponding parts to those in FIG. 17. A technique of allowing the focus of therapeutic ultrasonic waves to track a diseased part hat moves with respiration movement, such as a kidney calculus, employing the phased array technology is known as disclosed in Japanese Patent Publication No. 6-26549. A diseased part position detector 140 detects the position of a diseased part in real time. This detection technique is also known as disclosed in Japanese Patent Application No. 4-261420. For example, the position of a diseased part can be detected by taking the difference between two successive frames of an ultrasound- or CT-based image. Or, the position of a peak in echoes of ultrasonic waves can be detected as the position of a calculus.

The position detector 140 applies the position information of a diseased part to the system controller 9 constantly or periodically. The delay times associated with the piezoelectric elements are calculated so that the focus will be formed in the position of the diseased part. At this point, by using the correction described in connection with the sixth embodiment, the focus is permitted to track the diseased part with high precision.

Instead of being moved by the delay control as described previously, the focus of therapeutic ultrasonic waves may be moved by adjusting the refractive index of an acoustic lens locally.

Eighth Embodiment

The eighth embodiment is intended to eliminate noise mixed in an ultrasonic image reconstructed during treatment. The noise reduction is achieved by the ultrasonic diagnostic section 40 in the above-described embodiment.

Figure 20A:
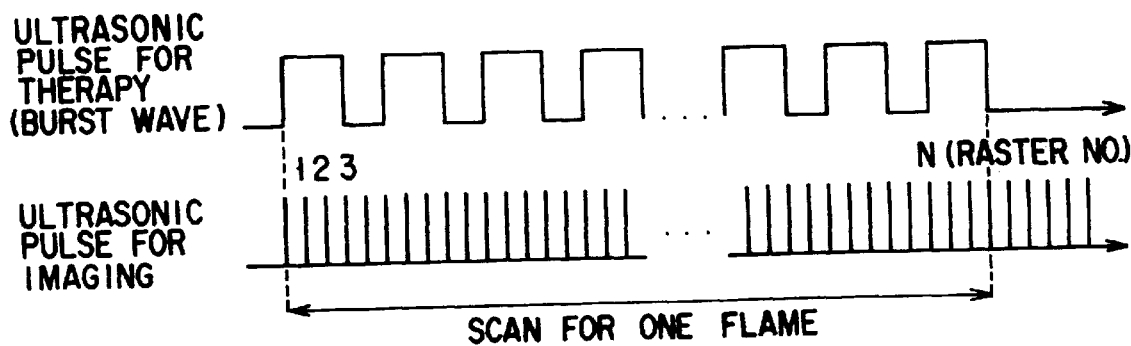
FIGS. 20A and 20B are diagrams for use in explanation of problems which are solved by an ultrasonic therapeutic apparatus according to an eighth embodiment of the invention.
Figure 20B:
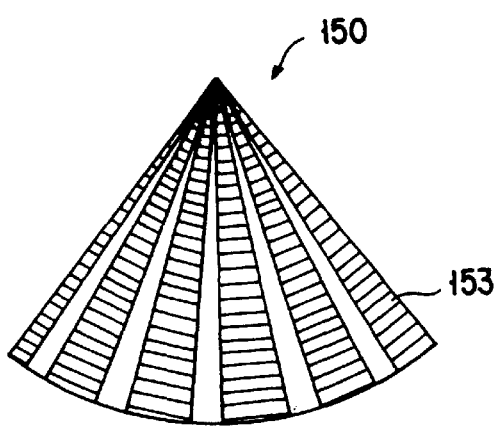

As shown in FIG. 20A, therapeutic ultrasonic waves are generated as burst waves at a first period. In vivo imaging ultrasonic pulses are generated at a second period that is considerably shorter than the first period. Echoes of each ultrasonic pulse are received prior to the transmission of the next ultrasonic pulse. The transmission/reception of imaging ultrasonic waves is repeated for N rasters. A scan is defined as a transmission/reception operation for one frame which repeats the transmission/reception of ultrasonic waves N times while changing the rasters from one to another. The echoes of the therapeutic ultrasonic pulses are significantly strong in comparison with those of imaging ultrasonic pulses. The reception gain is set for the echoes of the imaging ultrasonic pulses. For this reason, when a scan and application of therapeutic ultrasonic bursts are performed simultaneously, portions 153 of an ultrasonic image 150 that corresponds to the intervals when the high-intensity therapeutic ultrasonic waves (barst) are generated will be displayed as a region of extremely high luminance. The eighth embodiment provides several methods of removing the noise. One of the methods may be used in the apparatus; otherwise, all the methods may be incorporated into the apparatus so as to allow the operator to optionally select a desired one.

First Method

Figure 21:
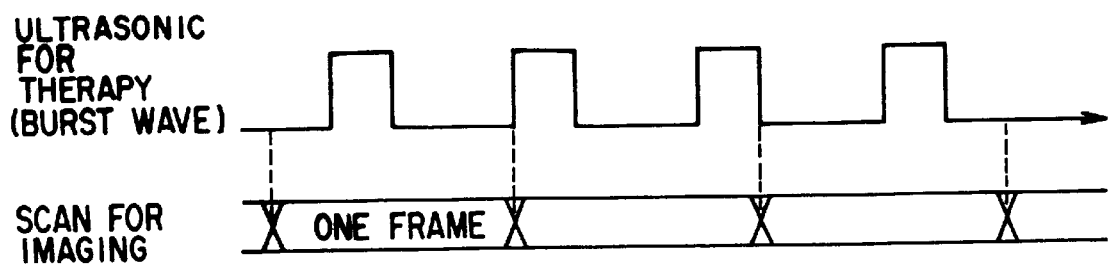
FIG. 21 shows a time relationship between therapeutic ultrasonic pulses and imaging scans.

FIG. 21 is a timing chart of the timing of therapeutic ultrasonic waves and the timing of scans. The ultrasonic waves are periodically generated at the first period. A sectional plane of a patient is periodically scanned at a period (frame period) independent of the first period.

Figures 22A, 22B, 22C:
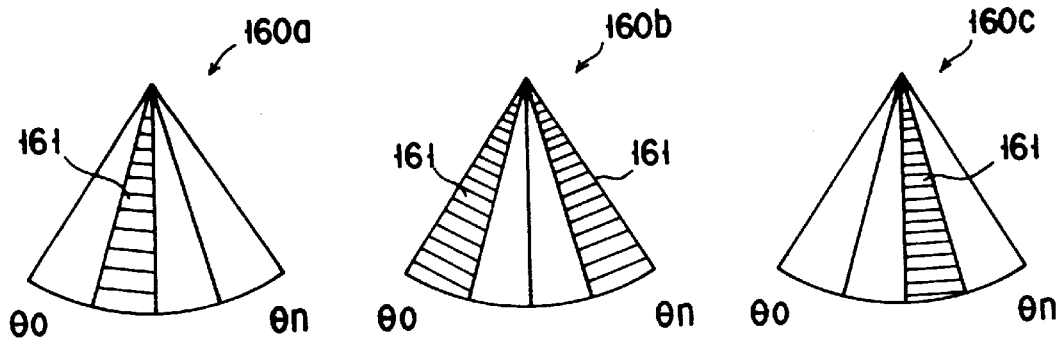
FIGS. 22A, 22B, 22C and 22D are diagrams for use in explanation of a first method of solving the problems associated with FIGS. 20A and 20B.
Figure 22D:
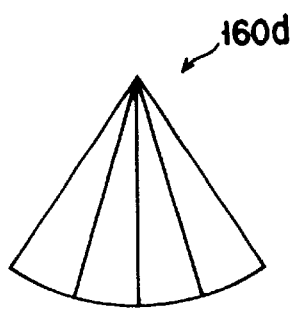

FIGS. 22A, 22B and 22C show three frames of a tissue tomographic image produced by successive scans. One frame of a tomographic image is mixed with at least one noise stripe 161 based on the therapeutic ultrasonic waves. The ultrasonic diagnostic section 40 is supplied by the system controller with sync signals for determining the timing of the therapeutic ultrasonic pulses and seeks an area on the tomographic image where the noise stripe 161 appears on the basis of the frame period and the sync signals. The section 40 removes the area of the noise stripe 161 from the image 160*c* corresponding to the latest frame and supplements that area with the corresponding areas on the images 160*a* and 160*b* produced immediately before that image 160*c*. As a result, a frame of a tomographic image 160*d* free from the noise stripe 161 is produced.

Second Method

Next, the second method will be described with reference to FIG. 23. Reference numeral 171 shows the timing of therapeutic ultrasonic bursts. The diagnostic section 40 interrupts a scan while a therapeutic ultrasonic burst is applied. When the application of a therapeutic ultrasonic pulse is stopped, the diagnostic section 40 restarts the scan from the raster next to the raster at the time of interruption.

Third Method

FIG. 24 is a diagram for use in explanation of the third method, in which 181 denotes the timing of therapeutic ultrasonic bursts. While a therapeutic ultrasonic burst is being applied, the diagnostic section 40 receives no echo, or does not write a received signal into an image memory, or does not display it on the CRT even though it has written into. Thus, a noise portion is blacked out on the image, but the white noise portion disappears.

Fourth Method

Figure 25A:
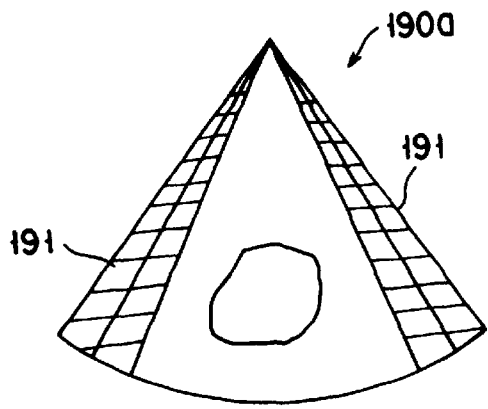
FIGS. 25A through 25F are diagrams for use in explanation of the third method of solving the problems associated with FIGS. 20A and 20B.
Figure 25B:
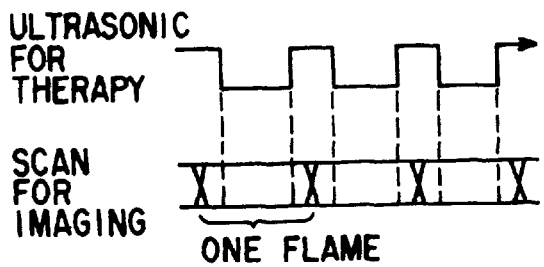
Figure 25C:
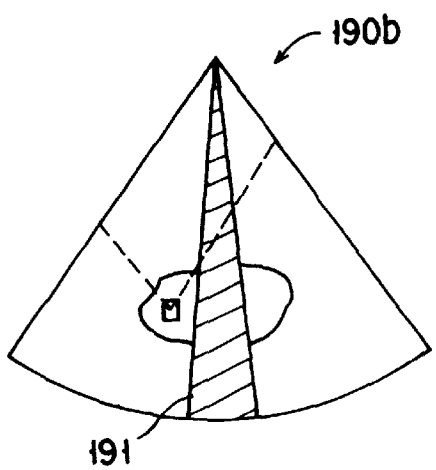
Figure 25D:
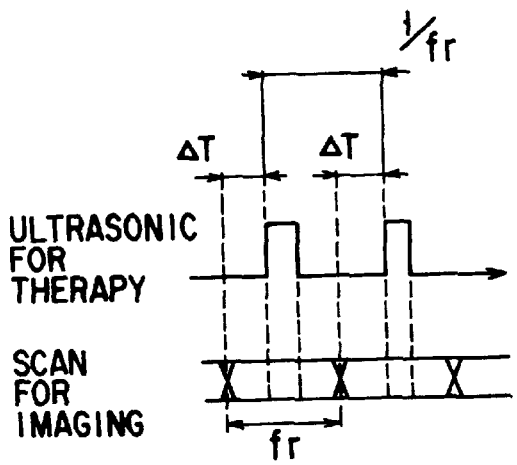
Figure 25E:
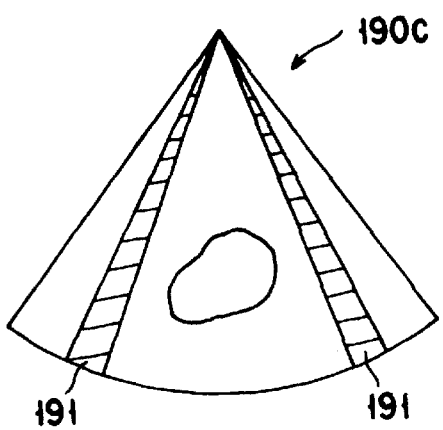
Figure 25F:
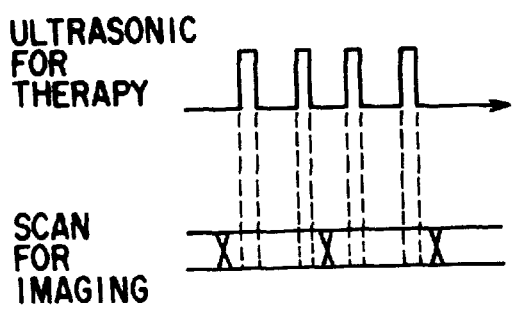

FIGS. 25A through 25F and FIGS. 26A through 26D are diagrams for use in explanation of the fourth method. FIGS. 25B, 25F, 26B and 26D, which illustrate the timing of therapeutic ultrasonic bursts and the timing of scans, correspond to FIGS. 25A, 25C, 26A and 26C, respectively. As shown in FIGS. 25A and 25B, the timing of scans with respect to therapeutic ultrasonic bursts is selected by the diagnostic section 40 such that noise stripes 191 appear at both end portions of a tomographic image 190*a*. As shown in FIGS. 25C and 25D, the diagnostic section 40 selects the timing of scans with the therapeutic ultrasonic bursts such that a noise stripe 191 appears in the central portion of a tomographic image 190*b*. As shown in FIGS. 25E and 25F, the diagnostic section 40 selects the timing of scans with the therapeutic ultrasonic bursts such that noise stripes 191 appear in portions other than the central portion and the end portions of an image 190*c*. As shown in FIGS. 26A and 26B, the diagnostic section selects the timing of scans with the therapeutic ultrasonic bursts such that a portion of interest (e.g., the focus) 201 is not hidden by a noise stripe 202 and the latter appears in the right half portion of an image 200. As shown in FIGS. 26C and 26D, the diagnostic section selects the timing of scans with the therapeutic ultrasonic bursts such that a portion of interest (e.g., the focus) 201 is not hidden by a noise stripe 202 and the latter appears in the left half portion of an image 200.

Ninth Embodiment

Figure 27:
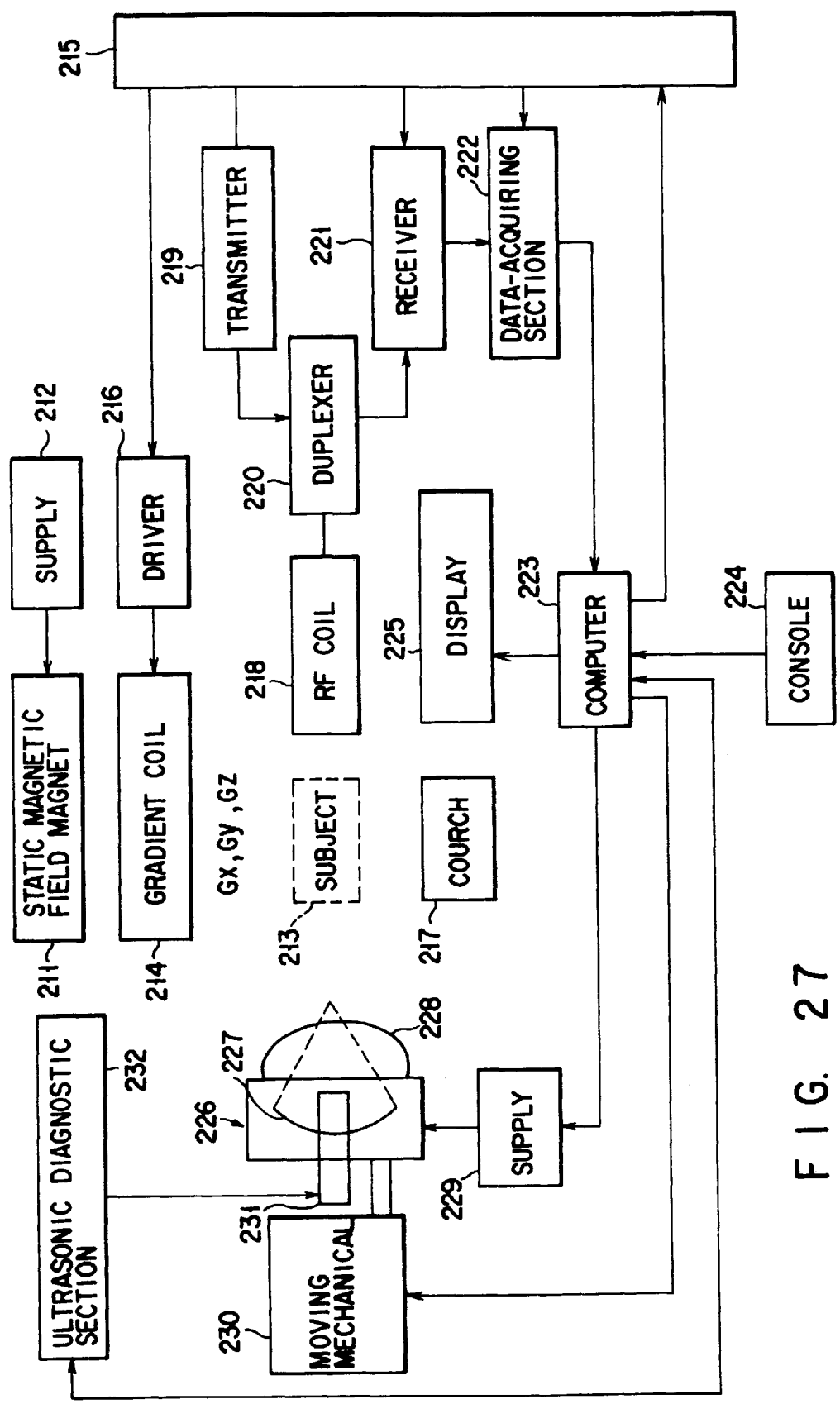
FIG. 27 shows an arrangement of an ultrasonic therapeutic apparatus according to a ninth embodiment of the invention.

FIG. 27 shows an arrangement of an ultrasonic therapeutic apparatus according to a ninth embodiment of the invention. In this embodiment, the ultrasonic therapeutic apparatus is combined with a magnetic resonance diagnostic apparatus. In the ultrasonic thermotherapy, it is important to realize highly precise positional matching between a diseased part and a heated region prior to the initiation of treatment.

The magnetic resonance diagnostic apparatus can measure the temperature distribution by employing the temperature dependence of chemical shifts and the relaxation time T1 (Y. Ishihara et al, Proc. 11th Ann. SMRM Meeting, 4803, 1992; H. Kato et al "Possible application of noninvasive thermometry for hyperthermia using NMR", International Conference on Cancer Therapy by Hyperthermia, Radiation and Drugs, Kyoto, Japan, September 1981).

In addition, the magnetic resonance diagnostic apparatus can measure a local region or a region of an arbitrary shape (C. J. Mardy and H. E. Cline, Journal of Magnetic Resonance, vol. 82, pp. 647 to 654, 1989; J. Pauly et al, "Three-Dimensional π Pulse", Proc. 10th Ann. SMRM Meeting, 493, 1991).

A living body has respiratory motion and physiological motion. It is therefore important to monitor erroneous application of ultrasonic waves to normal tissues and the present temperature of a diseased part in real time during ultrasonic thermotherapy. Researchers are experimenting with a new way to utilize the two-dimensional temperature distribution obtained by the NMR apparatus for monitoring. With thermotherapy, a diseased part is heated to a high temperature momentarily. thus, the monitoring requires fast responsibility in time (real-time property). In addition to temperature data, it is also required to obtain data indicating the therapeutic effect at a high time resolution. Thus, a time-resolution-oriented instrumentation system is needed.

In the NMR apparatus, in order to measure the temperature distribution corresponding to one frame, the spin-echo method requires the number of encoding steps times the time per excitation (repetition time). Assuming the repetition time to be two seconds and the number of encoding steps to be 128, about five minutes will be required. In the case of the field-echo method or the echo-planar method as well, both of which being faster than the spin-echo method, several seconds will be required to measure the temperature distribution for one frame. Further, a time lag of about several seconds is required for image reconstruction until the temperature distribution is output. Therefore, the real-time monitoring by the temperature distribution is difficult to implement.

Another way to increase the time resolution might be the measurement of one-dimensional temperature distribution, not two-dimensional temperature distribution. However, this way is not preferable because of the possibility that a heated region may deviate from a measurement line along which one-dimensional temperature measurement is made. In addition, the thickness of a slice causes the partial volume effect. Thus, there arises the possibility that the peak temperature may be measured to be a little low. Moreover, with the one-dimensional temperature distribution, it is impossible to determine if overheat is occurring in portions other than the measurement line.

The object of the ninth embodiment is to make it possible to monitor the temperature at high time resolution.

In FIG. 27, a static magnetic field forming magnet 211 is driven by an excitation power supply 212 to apply to a patient 213 a uniform static magnetic field in the z direction. Gradient coils 214 is placed within the static field magnet 211 and driven by a driver circuit 216 to apply to the patient gradient magnetic fields Gx, Gy and Gz in the three orthogonal x, y and z directions. A radio-frequency (RF) coil 218 is placed within the gradient coils 214 and supplied from a transmitter 219 via a duplexer 220 with a radio-frequency signal to produce a radio-frequency magnetic field. A receiver 221 receives a magnetic resonance signal from the patient via the RF coil 218 and the duplexer 220. As the RF coil use may be made of a saddle-shaped coil, a distributed-constant coil, a quadrature coil, or a surface coil. The duplexer allows the RF coil 218 to be switched between the transmitter 219 and the receiver 221. At the time of transmission, the duplexer transmits an RF signal from the transmitter 219 to the coil 218. At the time of reception, it leads a received signal from the coil 218 to the receiver 221.

A sequence controller 215 controls the driver circuit 216, the transmitter 219, and the receiver 221 so as to execute a predetermined pulse sequence. The receiver detects the received signal and limits its band. The band-limited received signal is fed into a data acquisition unit 222, which, in turn, converts the received signal into digital form for application to an electronic computer 223. The computer performs two-dimensional Fourier transform on the digital data to reconstruct an MR image and a temperature distribution image. Both the images are then applied to an image display unit 225 and displayed on its screen.

An ultrasonic applicator has a plurality of piezoelectric elements for producing therapeutic ultrasonic waves. The therapeutic ultrasonic waves are applied to the patient 213 through a coupling liquid, such as degassed water, contained in a water bag 228.

A power supply 229 for driving the applicator 226 is controlled by the computer 223. In order to allow the focus of the ultrasonic waves to move, the applicator 226 is supported by a moving mechanism 230 comprising an articulated mechanical arm. Note that the movement of the focus may be achieved by the phase control for the piezoelectric elements 227.

An ultrasonic probe 231 for in vivo imaging is mounted to the applicator 226 in its center. The probe is driven by an ultrasonic diagnostic section 232 to scan a plane section of the patient. Tissue sectional image data and intensity distribution data are reconstructed from a received signal and then displayed. The timing of scans is controlled by the computer 223. The tissue sectional image and the temperature distribution data are sent from the ultrasonic diagnostic section 232 to the computer 223. The computer combines the tissue sectional image or the intensity distribution and an MR image or a temperature distribution image.

The computer 223 seeks the maximum intensity point on the basis of the intensity distribution and, in order to obtain the applied energy of ultrasonic waves, accumulates continuously obtained intensity distribution and seeks two- or three-dimensional temperature distribution on the basis of the one-dimensional temperature distribution by the MR apparatus and the accumulated intensity distribution.

Figure 28:
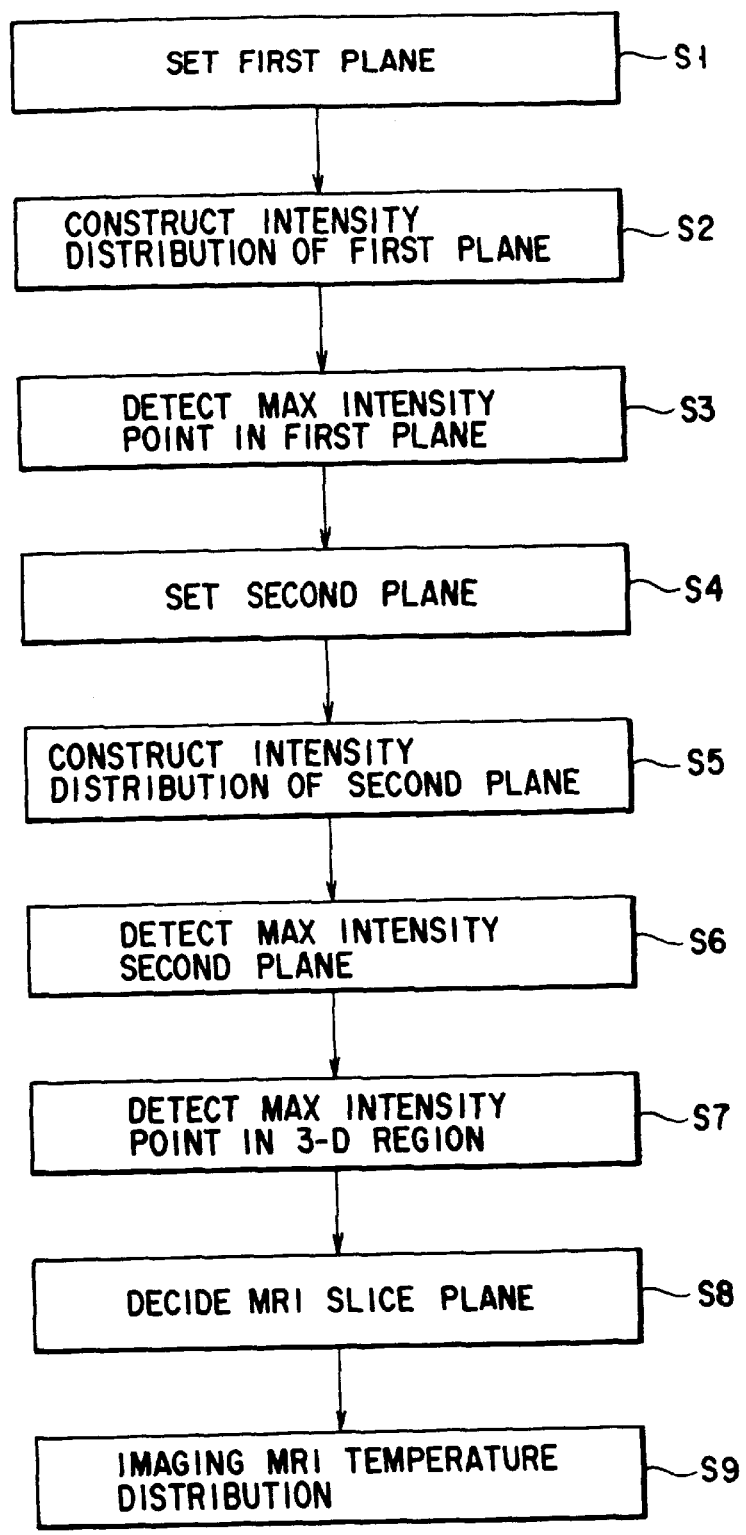
FIG. 28 is a flowchart for the determination of an MRI slice.
Figure 29:
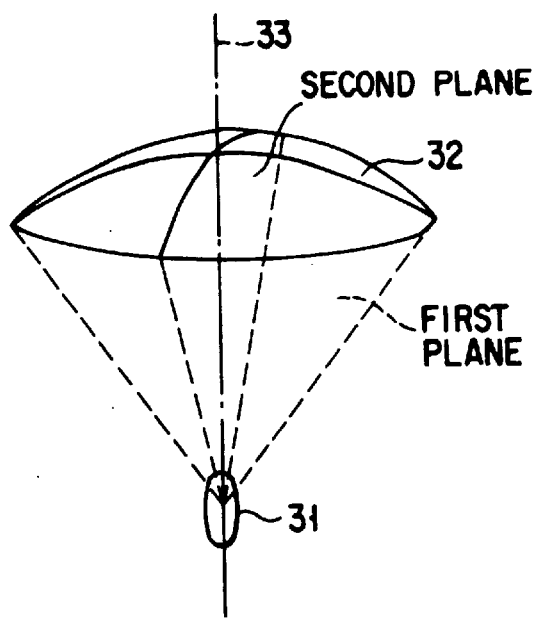
FIG. 29 show the first and second planes in FIG. 28.
Figure 31:
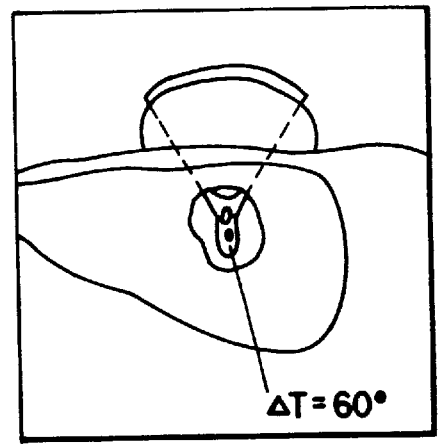
FIG. 31 shows an example of a composite image in which a B-mode image, a peak temperature, and a two-dimensional temperature distribution are combined.
Figure 30:
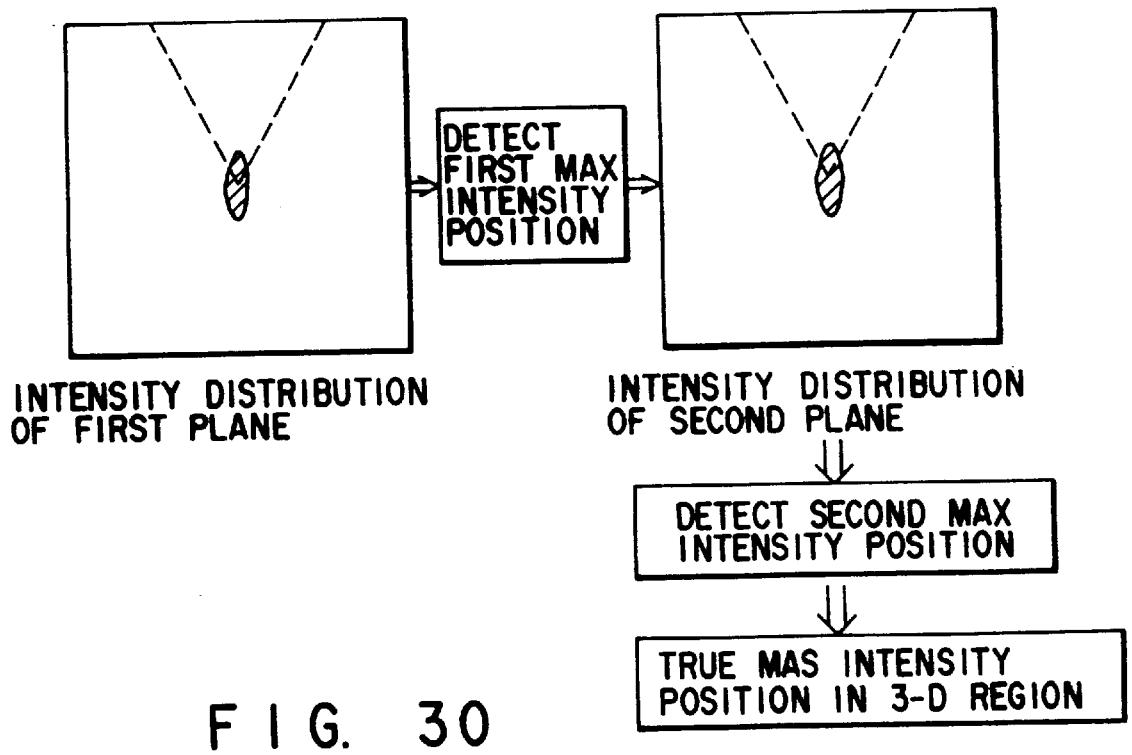
FIG. 30 is a supplementary diagram for use in explanation of the detection of three-dimensional coordinates of the point of maximum intensity.
Figure 32:
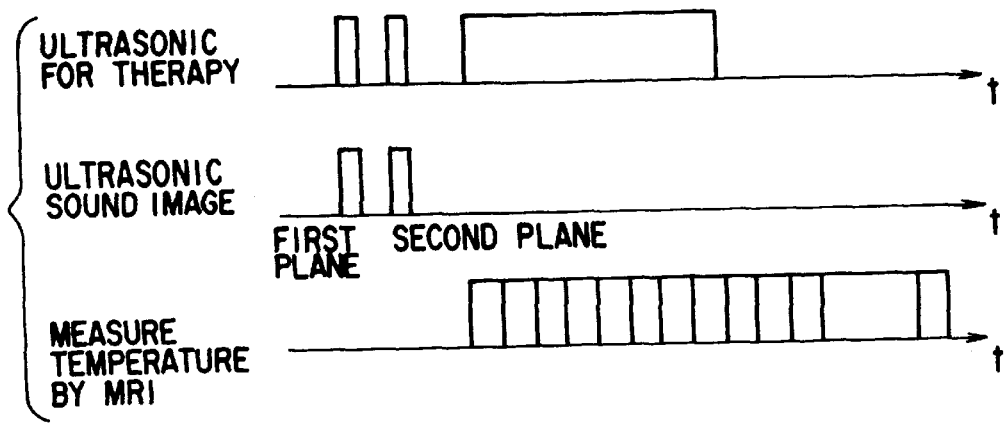
FIG. 32 is a time chart illustrating a process flow from the determination of an MRI slice to the termination of therapy.

FIG. 28 shows a slice-plane determination procedure. FIGS. 29, 30, and 31 are supplementary diagrams. The intensity distribution first intensity distribution) on a first plane containing the focus is produced (S1 and S2). The coordinates of the point of maximum intensity (first maximum intensity point) in the first plane is sought on the basis of the first intensity distribution (S3). The intensity distribution (second intensity distribution) on a second plane that contains the first maximum intensity point and is perpendicular to the first plane is produced (S4 and S5). The coordinates of the maximum intensity point (second maximum intensity point) is sought on the basis of the second intensity distribution (S6). The coordinates of the true maximum intensity point are detected on the basis of the coordinates of the second maximum intensity point and the position of the second plane (S7). A plane with the true maximum intensity point at its center is determined as the slice plane for the MR apparatus (S8). Or a line with the true maximum intensity point at its center is determined as an imaging line for the MR apparatus. The plane or line thus determined is imaged by the MR apparatus to reconstruct the two- or one-dimensional temperature distribution. The echo-planar technique is used for imaging. The temperature distribution is obtained by making the difference between phase images before and after therapy and converting the changes in phase to temperatures on the basis of the temperature dependence of chemical shifts. The temperature distribution is obtained by converting changes in an image signal to temperatures. In this case, intensity changes in an image signal is acquired in advance from changes in the relaxation time T1 with temperature.

Figure 33:
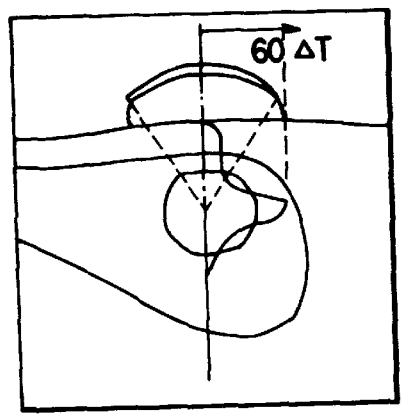
FIG. 33 shows an example of a composite image in which a B-mode image, a peak temperature, and a one-dimensional temperature distribution are combined.

The determination of a slice plane or line allows two- or one-dimensional temperature distribution centered at the maximum intensity point to be obtained. In order to remove the partial volume effect from the converted temperatures, it is preferable to make corrections based on a predicted distribution shape which has been acquired in advance. As shown in FIG. 31, the peak temperature in the temperature distribution is displayed on an MR image (tissue image). The spatial changes in temperature are displayed by hues or contour lines. If the intensity distribution is one-dimensional, it may be displayed in graphic form superimposed on an MR image as shown in FIG. 33.

The maximum intensity point of ultrasonic waves substantially coincides with the maximally heated point. Thus, the state of the maximally heated point can be monitored surely. When the temperatures or the shape of the temperature distribution differs from predetermined ones or one, it is expected that the coupling between the imaging probe 231 and the patient 213 is poor. In such case, the computer 223 stops forcibly the therapy, then makes a beep and issues a warning messages.

Figure 34:
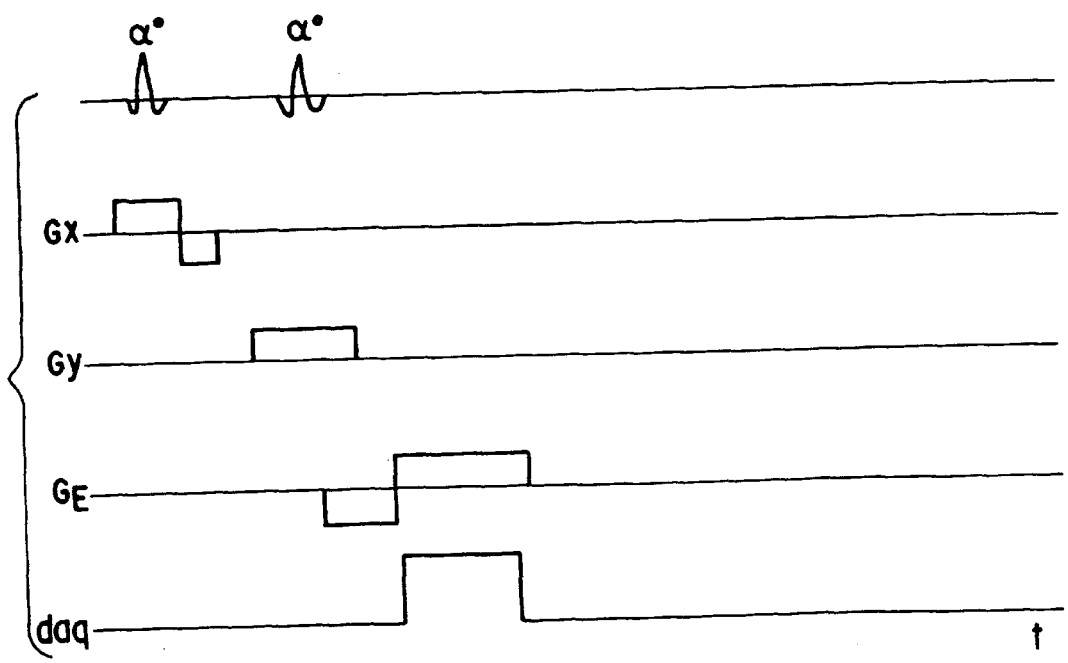
FIG. 34 shows an MRI pulse sequence for obtaining a one-dimensional temperature distribution.

FIG. 34 shows an example of a pulse sequence for obtaining one-dimensional temperature distribution. A slice selection process is first performed in the x direction and then a slice selection process is performed in the y direction, whereby an MR signal from a local region in the form of a column along the z direction is detected. The position information in the z direction is obtained by frequency encoding. Thereby, one-dimensional temperature distribution with respect to the z direction is acquired. Of course, an oblique imaging technique may be used to obtain one-dimensional temperature distribution in a desired direction.

The planes that are scanned by ultrasonic waves to search for the maximum intensity point need not be perpendicular to each other. For example, they may be parallel to each other. A comparison is made between maximum intensity points in two parallel scan planes. Another plane of intensity distribution is acquired in the vicinity of the maximum intensity point in one of the two parallel scan planes that is greater in intensity than the maximum intensity point in the other of the two parallel scan planes and then the similar comparison is made between the two planes. In this way, the comparison is repeated until a point is reached at which the maximum intensity is low. When the maximum intensity is low, the intensity distribution between the two is acquired. In this way, the maximum intensity points are searched for in sequence.

Figure 35:
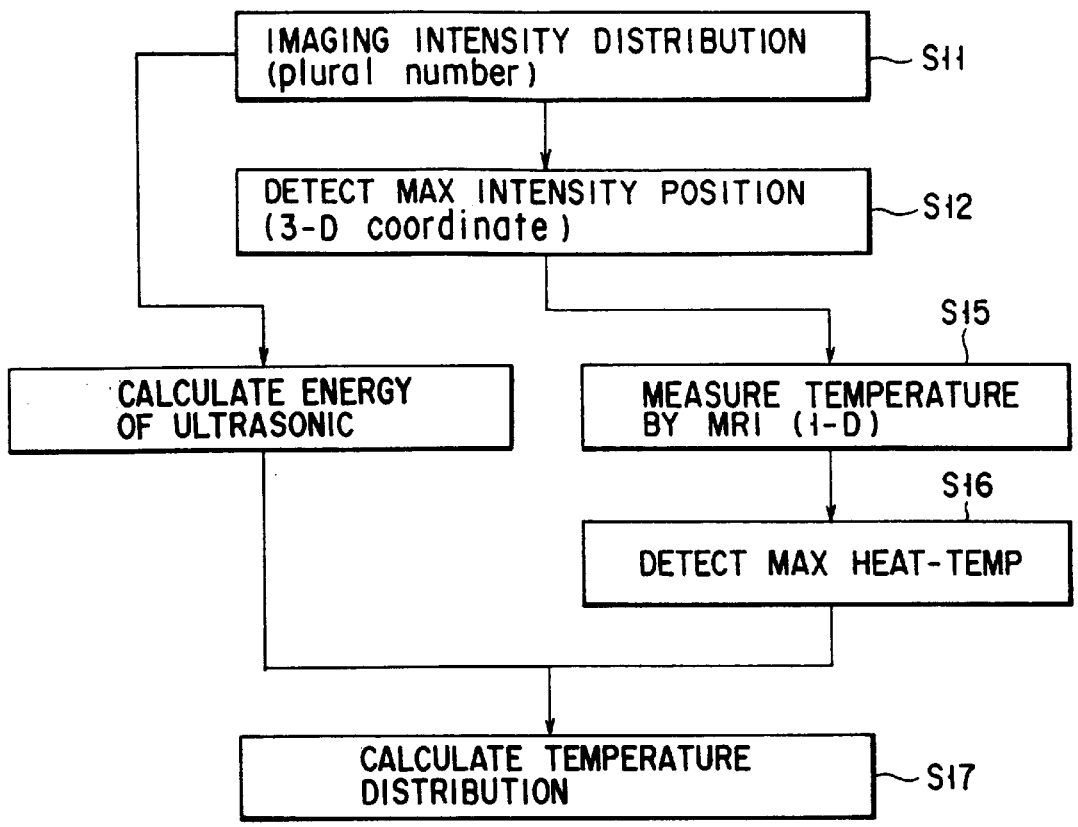
FIG. 35 is a flowchart for the presumption of a two-dimensional temperature distribution from a one-dimensional temperature distribution.

FIG. 35 shows a process flow to obtain two-dimensional temperature distribution on the basis of a one-dimensional temperature distribution and the applying time of therapeutic ultrasonic waves, by means of an MR apparatus. First, multiple intensity distributions on multiple scan planes are acquired (S11). The three-dimensional coordinates of the maximum intensity point is obtained on the basis of the intensity distributions (S12). Next, the one-dimensional temperature distribution on a line containing the maximum intensity point detected in S12 is measured (S15). The highest heating temperature in the one-dimensional temperature distribution is detected (S16). From the intensity distributions (accumulated distributions), thus calculated, and the time spent to apply therapeutic ultrasonic waves, the ultrasonic energy applied so far is obtained. The temperatures at other points are obtained based on the intensity distributions, thereby allowing the two-dimensional temperature distribution to be predicted (S17). The proportional relationship between the applied ultrasonic energy and the temperature is relatively reliable. Further, their reliability may be enhanced by detecting the maximum temperature using one-line temperature measurement method by MRI phase shift, and by feeding the highest temperature back to the calculated temperature distribution. Even if the patient moves during therapy, more accurate therapy becomes possible because the two-dimensional temperature distribution can be grasped in real time by utilizing the intensity distributions, the time spent to apply the therapeutic ultrasonic waves and the temperature detected using one-line temperature measurement method by MRI phase shift.

Figure 36:
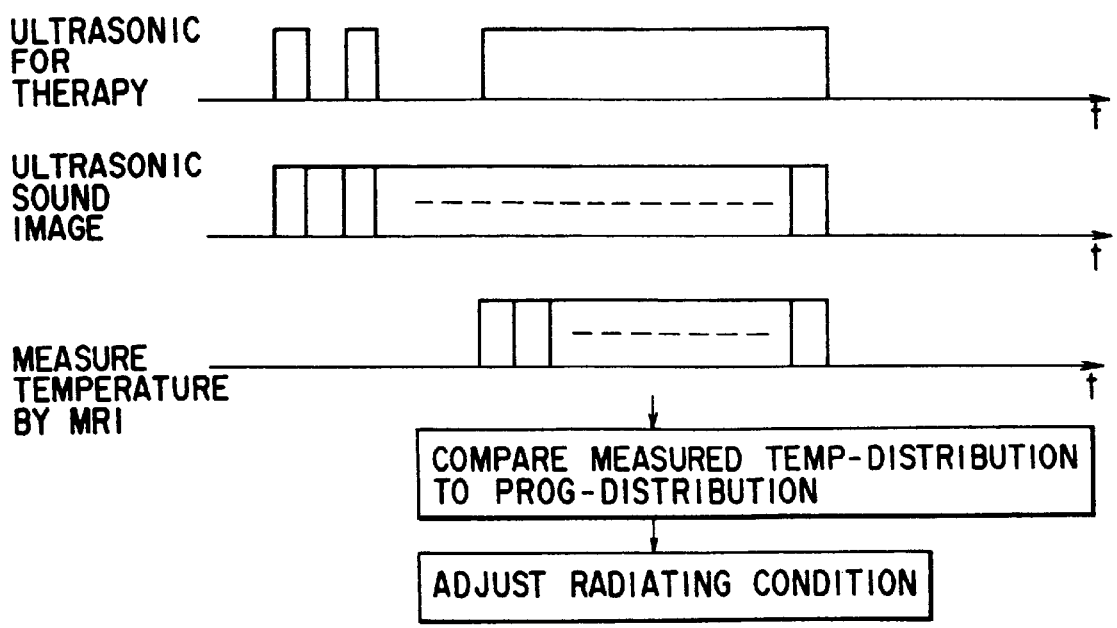
FIG. 36 is a diagram for use in explanation of real-time control of ultrasonic application conditions by comparison between a measured temperature distribution and a temperature distribution presumed from the application conditions.

The two-dimensional temperature distribution obtained in real time may be used for control of therapeutic ultrasonic wave application conditions. For example, as shown in FIG. 36, a comparison is made between the temperature distribution expected from the application conditions and the actually measured temperature distribution. When the difference between the two exceeds a threshold, or an unexpected region is overheated, the application of ultrasonic waves is stopped, or a beep is made, or an warning message is displayed. Alternatively, the intensity of ultrasonic waves is controlled so as to such a situation. For example, when the measured temperature is lower than the set temperature, the ultrasonic intensity is elevated.

According to the ninth embodiment, the ultrasonic therapeutic apparatus using MRI permits the temperature of a diseased part to be measured accurately during therapy and the temperature distribution to be acquired at high speed.

Tenth Embodiment

FIG. 37 shows an arrangement of an ultrasonic application apparatus according to a tenth embodiment of the invention. In this figure, like reference numerals are used to denote corresponding pats to those in FIGS. 1 and 6 and description thereof is omitted. The ultrasonic diagnostic section 40 is provided with an MTI (Moving Target Indication) operation unit 400, which comprises a quadrature detector, an A/D converter, an MTI filter, an autocorrelator, and an operation unit and acquires two-dimensional distribution of movement information about a moving target, such as blood flow, on the basis of the phase difference between received signals due to the motion of the target. The two-dimensional distribution of the movement information is displayed in color on the display in the ultrasonic diagnostic section 40. The MTI operation unit 400 is well known to those skilled in the art and hence the detailed description thereof is omitted here. For example, refer to Medical Ultrasonic Equipment Handbook edited by Electronic Industries Association of Japan, pp. 172 to 175, Corona company, Tokyo.

The diagnostic section 40 applies a sync signal 101 (first sync signal) to a timing signal generator 180. The sync signal 101 is defined as a pulse train of pulses with a predetermined duration and a fixed period. The ultrasonic diagnostic section 40 causes an imaging probe 16 to apply imagine ultrasonic waves upon lapse of a predetermined time (dt) from the leading edge of the first sync signal 101.

The timing signal generator 180 is responsive to the first sync signal 101 to produce a second sync signal 102, which is defined as a pulse train of pulses with a predetermined duration and the same period as the first sync signal 101. The ultrasonic waves for imaging the intensity distribution are applied at the leading edge of the second sync signal 102. Hence, the first and second sync signals are out of sync. The time difference between the first and second sync signals is set to dt. This time difference is adjusted by the system controller 9 so that in vivo imaging ultrasonic waves and ultrasonic waves for imaging the intensity distribution arrive at the focus at the same time. The basis of calculating the time difference dt is the same as the method described in connection with the first and second embodiments.

The second sync signal 102 is applied from the timing signal generator 180 to a phase shifter 47 via a switch 480. The phase shifter 470 shifts the phase of the second sync signal 102 to produce a third sync signal 103.

Figure 38:
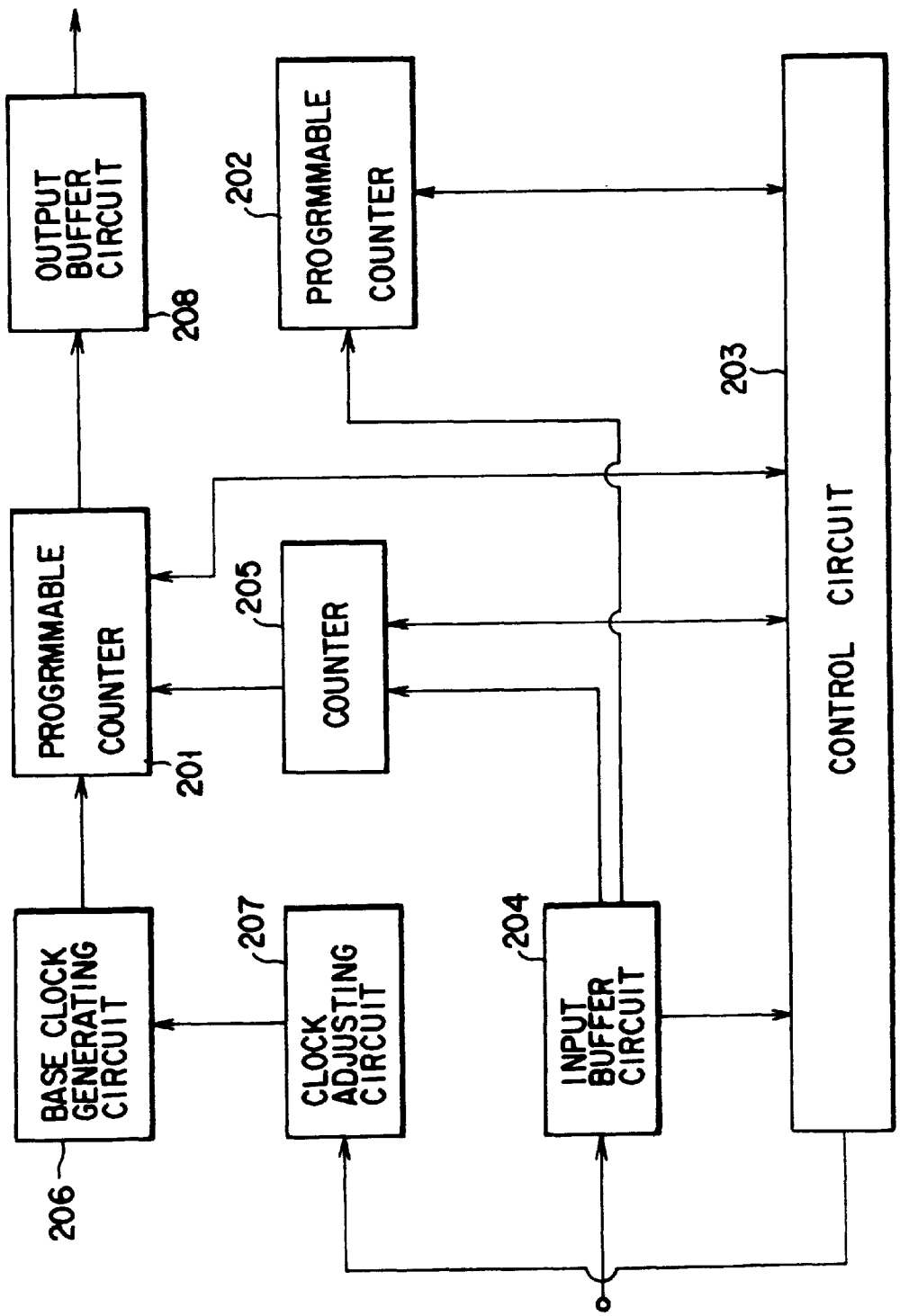
FIG. 38 is a block diagram of the phase shifter of FIG. 37.

FIG. 38 shows an arrangement of the phase shifter 470 and FIG. 39 shows a time relation between the first and third sync signals 101 and 103. The phase shifter 470 comprises programmable N-modulo counters 201 and 202, a control circuit 203 serving as the control center, an input buffer 204, a counter 205, a reference clock generator 206, a reference clock characteristic adjusting circuit 207, and an output buffer 208. The third sync signal 103 is defined as a pulse train of pulses with a predetermined duration. The reference clock generator 206 generates clocks at a period of T2. T2 is much shorter than the sync signal 102. The operator can sets $T_2$ at any value desired, for example at 1/10 of the period of the sync signal 102. The programmable N-scale counter 201 produces a pulse whenever the count of the clocks from the reference clock generator 206 reaches N. The pulse is output as the third sync signal 103 from the output buffer 208.

N set in the programmable N-scale counter circuit 201 is incremented every time a sync signal 102 is input. N is reset to 1 by a reset signal which the control circuit 203 outputs every time the period the operator has preset elapses. The operator sets $N_2$ of the sync signal 102 so that a reset signal is output every time there is an input. $N_2$ is set in the programmable N-scale counter circuit 202. When the sync signal 102 is input $N_2$ times, the programmable N-scale counter circuit 202 outputs a reset signal to the control circuit 203. The value for $N_2$ can be changed as desired.

A waveform generator 460 is responsive to the third sync signal 103 to apply drive pulses to the therapeutic ultrasonic transducer 2, thereby producing ultrasonic pulses for imaging intensity distribution.

The transmission of in vivo imaging ultrasonic waves is performed upon lapse of a predetermined time from the leading edge of the first sync signal.

The second sync signal 102 is produced by the timing signal generator 180 for the same period as the first sync signal, but is shifted by a time dt.

Produced by the phase shifter 470 according to the second sync signal, the third sync signal 103 is delayed with respect to the second sync signal by a time in the range of $T_2$ to less than $N_2 \cdot T_2$. The delay time is incremented by $T_2$ at each pulse in the second sync signal. When the maximum delay time is reached, return is made to $T_2$. The delay time is changed in such a cycle.

The ultrasonic pulses for intensity distribution imaging are produced repeatedly in response to the third sync signal. When the delay time is zero, echoes from the focus of ultrasonic pulses for imaging intensity distribution are received by the imaging probe 16 simultaneously with echoes from the focus of the in vivo imaging ultrasonic waves. When the delay time is not zero, on the other hand, the echoes from the focus of the therapeutic ultrasonic pulses are received by the imaging probe earlier than echoes from the focus of the imaging ultrasonic waves, by the above-mentioned delay time. The delay time is incremented by $T_2$ at each therapeutic ultrasonic pulse.

Thus, the phase of a received echo signal is changed at each ultrasonic pulse for intensity distribution imaging.

The echo components of the ultrasonic pulses for intensity distribution imaging pass through the MTI is filter since they are different in phase. They are then imaged as the intensity distribution on the two-dimensional distribution of movement information of moving targets by the MTI operation unit 400. In this way, the intensity distribution can be imaged along with, for example, blood flow by the MTI operation unit 400.

Depending on the connection state of the switch 480, it is possible to apply directly the second sync signal 102 to the waveform generator 460. In this case, the intensity distribution is obtained by normal B-mode processing. The arrangement of the phase shifter 470 is not limited to that FIG. 38. In the above, the delay time was described as being changed regularly in units of $T_2$. The delay time may be changed randomly. This is implemented by the provision, in place of the phase shifter 470, of a jitter circuit that makes the pulse repetition period of the second sync signal 102 irregular. In the above, the phase differences are acquired by adjusting the timing of ultrasonic pulses for imaging intensity distribution. Instead, the phase differences may be imparted to the received echo signals. In addition, the third sync signal is adjusted relative to the first sync signal. Instead, the period of the first sync signal may be changed relative to the third sync signal whose period is fixed at a constant period.

Eleventh Embodiment

FIG. 40 shows an arrangement of an ultrasonic application apparatus according to an eleventh embodiment of the invention. In this figure, like reference numerals are used to denote corresponding parts to those in FIGS. 1, 6, and 37. The ultrasonic diagnostic section 40 has a B-mode processing system and an intensity distribution system which share a transmitter/receiver 402, a digital scan converter 412, and a CRT 413.

The B-mode processing system, which is adapted to produce a B-mode image on the basis of received signals from the transmitter/receiver 402, includes a detector 409, a gain adjuster 410, and an analog-to-digital converter 411. The detector 409 detects the received signals from the transmitter/receiver 409. The gain adjuster 410 amplifies the detected signals from the detector 409. The analog-to-digital converter 411 converts the amplified detected signals into digital form.

The intensity distribution processing system, which is adapted to produce intensity distribution on the basis of received signals from the transmitter/receiver 402, includes a quadrature phase detector 414, a gain adjuster 407, and an analog-to-digital converter 408.

The quadrature phase detector 414 comprises a mixer 404 and a lowpass filter 406 to extract from the received signals the components in the highest energy band associated with ultrasonic waves for imaging intensity distribution (high energy band components). The high energy band components are components in the band (fundamental wave band) centered at the fundamental frequency f1, i.e., the fundamental wave components, or components in a band (harmonic wave band) centered at a higher frequency that is an integral multiple of the fundamental frequency f1, i.e., the harmonic wave components. The mixer 405 multiplies the received signals from the transmitter/receiver 102 and a reference signal of a reference frequency from a signal generator 502. The reference frequency is the fundamental frequency, f1, of the therapeutic ultrasonic waves or a frequency that is an integral multiple of f1, i.e., n×f1.

The quadrature detector 414 may be replaced with a bandpass filter.

The reference frequency may be sought in the following manner. That is, a spectrum analysis is made of the received signal from the imaging probe 16 in a computation unit 44, a frequency component of the highest energy is extracted from the spectrum, and that frequency component or a frequency close to that frequency is selected to be the reference frequency. In this case, the system controller 9 controls the signal generator 502 so that the reference signal will be generated at the reference frequency thus sought. By doing so, the frequency at the highest energy can be detected from the received signal. The detection of the frequency at the highest energy may be repeated during therapy each time an echo signal is received, or may be repeated at regular intervals, or may be performed once prior to therapy in which case, once sought, the reference frequency is fixed after that. Alternatively, the operator may adjust the reference frequency.

The gain adjuster 407 amplifies the detected signal from the quadrature phase detector 414. The analog-to-digital converter 408 converts the amplified detected signal into digital form.

A B-mode image produced by the B-mode processing system and an intensity distribution image produced by the intensity distribution processing system are combined into one frame of image by the digital scan converter 412 and then displayed on the CRt 413.

The B-mode image data and the intensity distribution data thus obtained are combined into one frame of image in the digital scan converter and then displayed on the CRT 413.

The intensity distribution is produced from the high-energy band components extracted from the received signal in that manner, permitting a high intensity region such as the focus to be emphasized. Thus, it becomes possible to check the positional relationship between the focus and the diseased part and to make sure that normal regions are not irradiated with strong ultrasonic waves, allowing safe and sure therapy to be implemented.

The first and second gains can be adjusted separately because the received signal and the high-energy band components extracted from the received signal are processed separately.

Twelfth Embodiment

Figure 42:
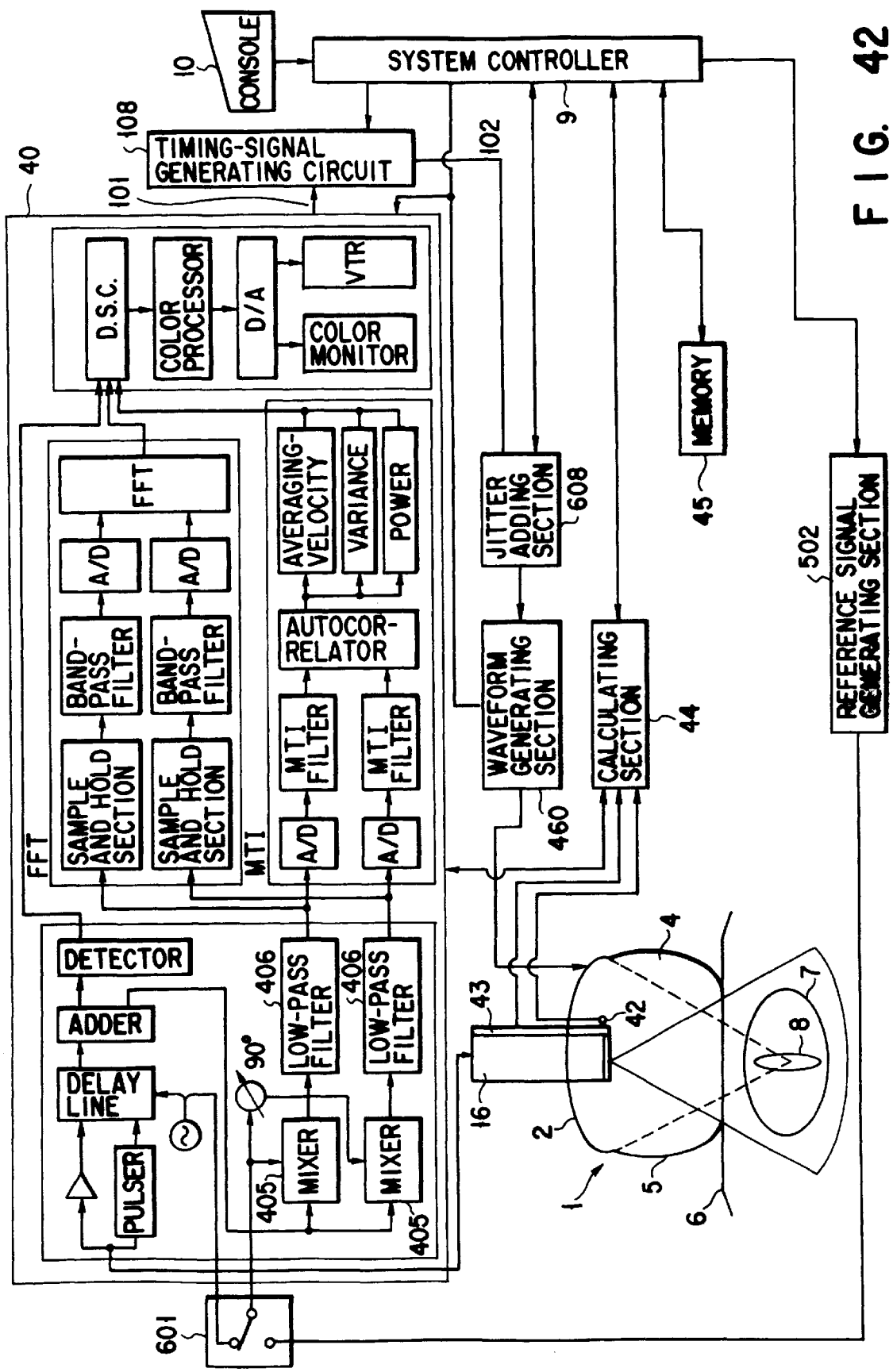
FIG. 42 shows a modification of the arrangement of FIG. 40.

FIG. 42 shows an arrangement of an ultrasonic therapeutic apparatus according to a twelfth embodiment of the invention. In this figure, like reference numerals are used to denote corresponding parts to those in FIGS. 1, 6, 37, and 40 and description thereof is omitted.

The ultrasonic diagnostic section 40 is identical in arrangement to a general ultrasonic diagnostic section comprising an analog section, an FFT section, an MTI section, and a display section. The analog section has a quadrature phase detector comprising a mixer 405 and a lowpass filter 406.

A switch 601 connects either of an oscillator and a signal generator 502 to a mixer 405 under the control of the system controller 9. The oscillator generates a first reference signal. The signal generator 502 generates a second reference signal. The frequency of the first reference signal is set to the within the band for the imaging ultrasonic waves. The frequency of the second reference signal is set within the band for the ultrasonic pulses for intensity distribution imaging.

As with the tenth embodiment, in order to allow the intensity distribution to be produced from MTI filter outputs, a jitter imparting circuit 608 is connected between a timing signal generator 180 and a waveform generator 460, which imparts a jitter to a sync signal 102 that determines the timing of ultrasonic pulses for intensity distribution imaging. Instead of providing the jitter imparting circuit, the MTI operation unit may be disconnected at intensity distribution imaging time. In this case, the number of times of transmission per raster (one line of an ultrasonic tomographic image) can be made one. Thus, the frame rate and the real-time property are improved, and the temperature elevation within a living body due to application of ultrasonic waves is checked.

At the time of two-dimensional color Doppler imaging, the first reference signal is applied from the oscillator to the mixer 405 through the switch 601. At the time of intensity distribution imaging, on the other hand, the second reference signal is applied from the signal generator 502 to the mixer 405 through the switch 601.

The two-dimensional color Doppler imaging is performed on the basis of frequency components of high energy density in echoes of in vivo imaging ultrasonic waves. On the other hand, the intensity distribution imaging is performed on the basis of frequency components of high energy density in echoes of ultrasonic waves for intensity distribution imaging.

Thus, the two-dimensional color Doppler imaging and the intensity distribution imaging can be performed with high precision.

Figure 43:
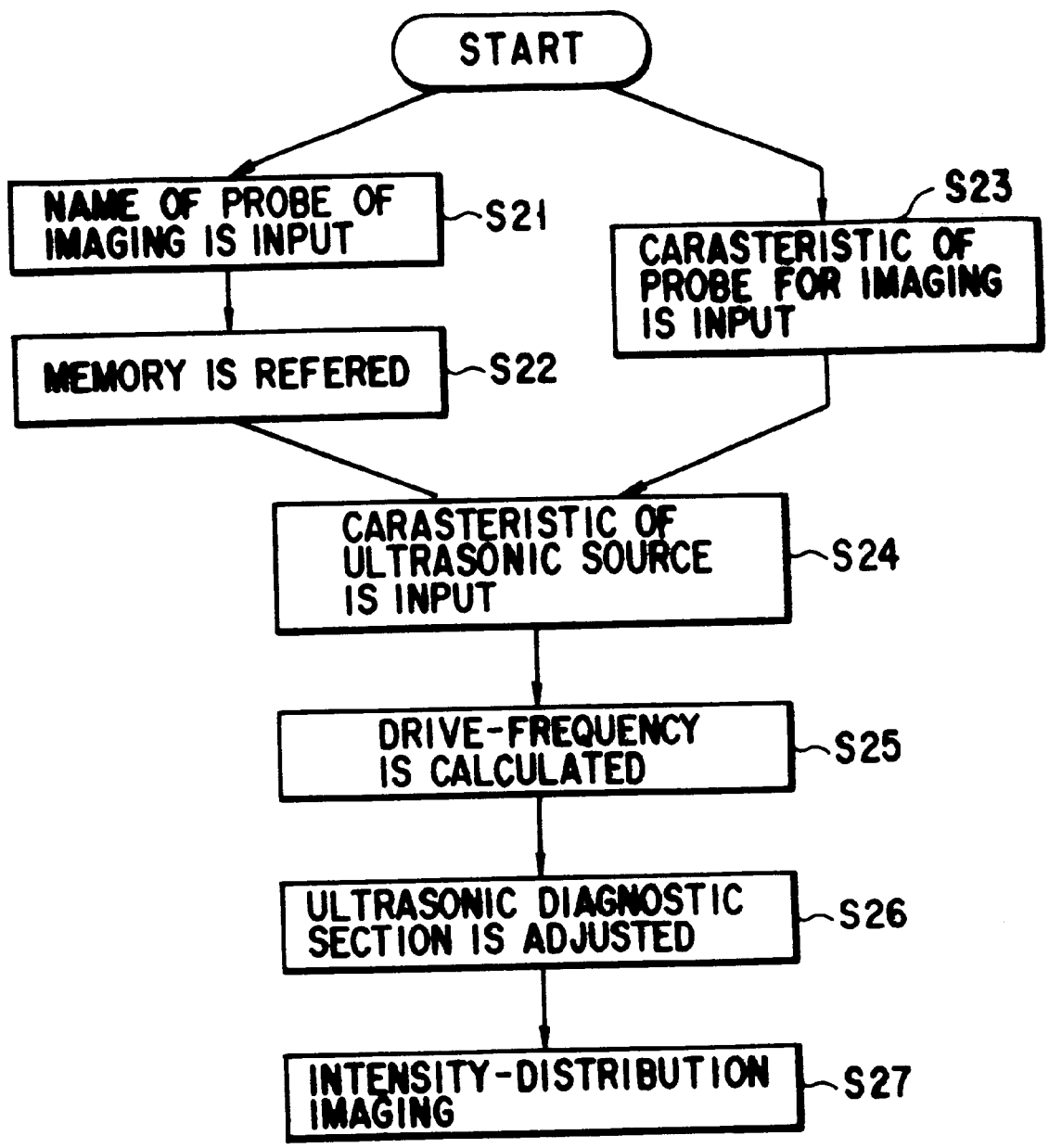
FIG. 43 is a flowchart for the determination of a driving frequency of ultrasonic waves for intensity distribution.

FIG. 43 shows a procedure leading to the intensity distribution imaging. First, the name of the imaging probe 16 connected to the ultrasonic diagnostic section 40 is entered by the operator into the system controller 9 via the console 10 (S21). The memory 45 stores the names of various types of imaging probes and their frequency characteristics. The frequency characteristic of the probe connected to the diagnostic section is read from the memory 45 into the system controller 9 (S22). The processes S21 and S22 may be replaced by a process (S23) in which the sensitivity characteristic of the probe in use is directly entered by the operator into the system controller 9 via the console 10.

Figure 44:
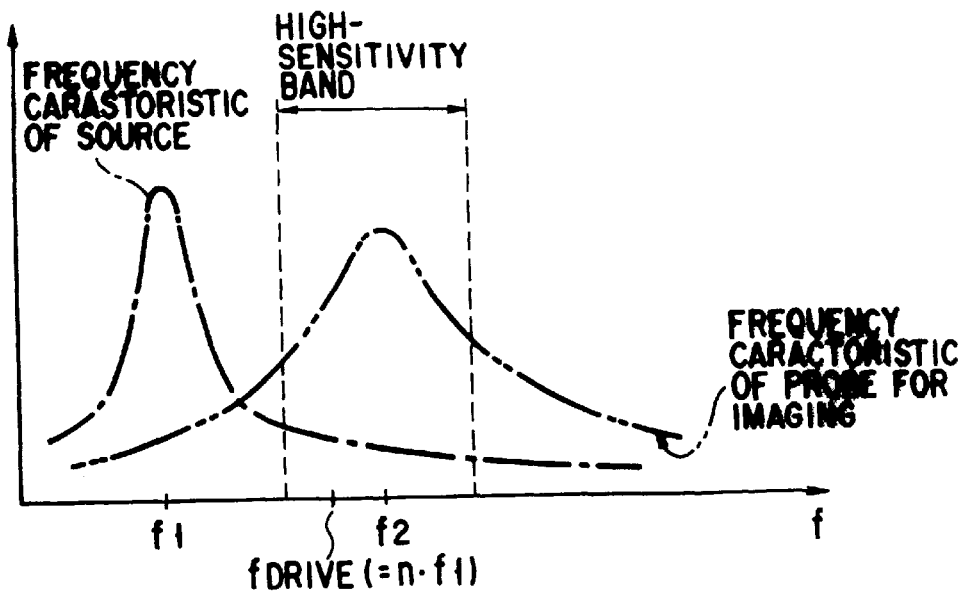
FIG. 44 shows driving frequencies of a source of therapeutic ultrasonic waves.

The frequency characteristic of the therapeutic ultrasonic transducer 2, specifically its inherent resonant frequency, is entered by the operator into the system controller 9 through the console 10 (S24). The drive frequency of the therapeutic ultrasonic transducer 2 is calculated by the system controller 9 from the frequency characteristic of the probe 16 and the resonant frequency of the therapeutic ultrasonic transducer 2 (S25). As shown in FIG. 44, the driving frequency f is the resonant frequency of the therapeutic ultrasonic wave transducer 2, within the band of the transducer 2 or is an integral multiple of the resonant frequency of the transducer 2, and does within the high-sensitivity band of the imaging probe 16.

The characteristic of the ultrasonic diagnostic section 40 are adjusted according to the drive frequency fdrive (S26). Specifically, the filtering characteristics in the diagnostic section 40 are adjusted by the system controller 9 according to the drive frequency fdrive. The intensity distribution imaging is initiated next (S27).

Driving the therapeutic ultrasonic transducer 2 at the drive frequency fdrive at the time of intensity distribution imaging allows the overall efficiency including the efficiency of transmission by that transducer and the efficiency of reception by the imaging probe 16 to be increased.

Figure 45:
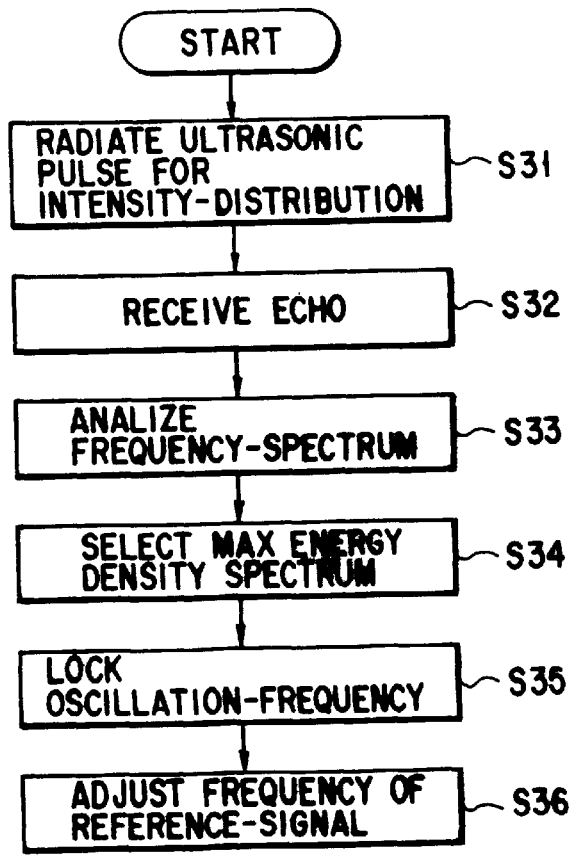
FIG. 45 is a flowchart for the search of receiving frequencies.

FIG. 45 shows a procedure of setting the reference frequency. Intensity distribution imaging ultrasonic pulses are applied from the therapeutic ultrasonic transducer 2 (S31). The echoes are received by the imaging probe 16 (S32). The received echo signal is subjected to fast Fourier transform in the computation unit 440, so that a frequency spectrum is obtained (S33). In this frequency spectrum, the frequency of the highest energy density is selected by the computation unit 440 (S34). The oscillation frequency of the signal generator 502 is locked in to a frequency that is slightly offset from that selected frequency (S35). The reference signal at the locked frequency is applied from the signal generator 502 to the mixer 405 (S36).

Although the therapeutic ultrasonic transducer and the imaging probe are provided separately, the probe can be used to produce therapeutic ultrasonic waves and ultrasonic pulses for intensity distribution imaging. In this case, in order to produce ultrasonic pulses for imaging intensity distribution and imaging ultrasonic waves simultaneously, a drive signal for piezoelectric elements is required to have an in-vivo electric signal for imaging intensity distribution and an electric signal for imaging, which are superimposed.

Thirteenth Embodiment

Figure 46:
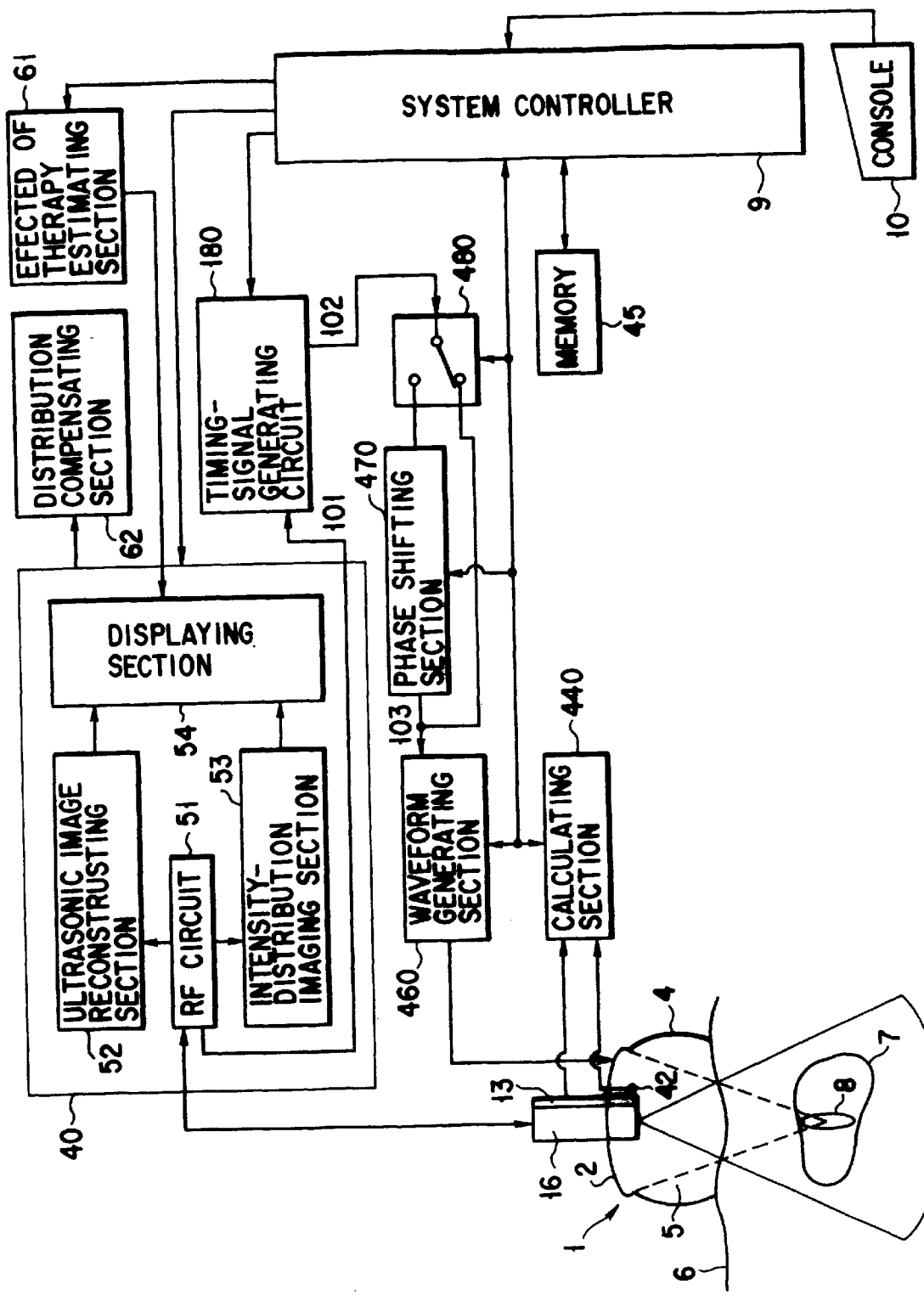
FIG. 46 shows an arrangement of an ultrasonic wave application apparatus according to a twelfth embodiment of the invention.

FIG. 46 shows an arrangement of an ultrasonic therapeutic apparatus according to a thirteenth embodiment of the invention. In this figure, like reference numerals are used to denote corresponding parts to those in FIGS. 1, 6, and 37. The ultrasonic diagnostic section 40 includes an RF circuit 51 for transmitting/receiving ultrasonic waves through the imaging probe 16, an image reconstruction section 52 for reconstructing a B-mode image of a patient from a received echo signal by the probe, an ultrasonic condition imaging section 53 for imaging the intensity distribution of ultrasonic waves from the received echo signal by the probe, and a display section 54 for displaying the B-mode image and the intensity distribution.

The RF circuit 51 applies drive signals to the probe 16 at predetermined times and amplifies received echo signals from the probe 16. In addition, the RF circuit extracts signal components adapted for intensity distribution from the received echo signal for subsequent application to the ultrasonic distribution condition imaging section 53. This extraction process is performed by a lowpass filter, a bandpass filter, or a quadrature detector.

To the display section 54 are connected a therapeutic effect estimation section 61 and a distribution correction section 62. As a result of cavitation, variations in acoustic characteristic of tissues due to thermal metamorphosis and so on, a treating region where thermal metamorphosis and necrosis actually occur will shift from the focus to the side of the applicator 1. The size of treating region and depends on the time spent to apply acoustic energy and is not equal to the size of the focus.

The therapeutic effect estimation section 61 determines the size and position of the treating region and performs on the display section 54 a process required to display a treating region indicating marker in the determined size and the determined position.

The distribution correction section 62 performs on the display section 54 a process required to correct spatial displacement of the intensity distribution relative to the B-mode image. The amount of correction for the spatial displacement of intensity distribution differs from scan plane to scan plane. The amount of correction is calculated in advance and stored in an internal memory of the distribution correction section 62. The amount of correction is calculated as follows. Regard the therapeutic ultrasonic transducer 2 as a cluster of tiny sources of sound. By superimposing an ultrasonic wave from each source, the state of waves in homogeneous medium can be obtained for each position. The amount of correction is calculated on the basis of the state of waves. Although, in FIG. 46, the distribution correction section 62 receives position information about the intensity distribution from the display section 54, it may receive the position information from the system controller 9.

The operation of the present embodiment will be described next. First, the plane section containing the diseased part 7 is scanned by ultrasonic waves emitted from the imaging probe 16, so that the diseased part appears on a B-mode image. At this point, treatment can be given in accordance with a plan for treatment which has been made in advance on the basis of the form of the diseased part that was measured by using CT or MRI. In this case, the operator is allowed to operate the apparatus in accordance with the contents of that plan displayed on a CRT that is prepared separately. Alternatively, the contents of that plan may be stored in the memory 45 in advance so that the system controller 9 can read them in sequence for subsequent treatment. In addition, a treatment plan making apparatus and an actual treatment room may be on-line connected to allow treatment based on a plan for treatment and fast amendment to the plan in the event of an unforeseen situation during treatment.

The position or angle of the imaging probe 16 with respect to the patient is changed to shift the scan plane of the patient. By using a plurality of B-mode images or a three-dimensional image constructed from a plurality of B-mode images, the three-dimensional form of the diseased part 7 and the presence of an important organ or a bone on the propagation paths of ultrasonic waves are determined. All the B-mode image data is stored in the memory 45.

Next, application conditions of therapeutic ultrasonic waves are adjusted by the system controller 9 on the basis of at least one of the amplitude and the energy in a predetermined band of echo components of the therapeutic ultrasonic waves from the diseased part 7 that are contained in the received echo signal. The application conditions include the application intensity, i.e., the amplitude (peak voltage) of a drive signal applied to the transducer 2, and the application time, i.e., the duration of the drive signal. The echo components are extracted from the received echo signal by the computation unit 440. The echo components can be extracted by gating the received echo signal at the time corresponding to the depth of the diseased part 7. For this purpose only, the ultrasonic diagnostic section 40 need not be of the B-mode type. It is allowed to be of the M-mode type.

The application intensity and the application time are determined by the system controller 9 on the basis of the intensity of echo components from the diseased part 7, the ultrasonic absorption factor of the diseased part, the attenuation factor of ultrasonic waves at the diseased part, the presence of an important organ or bone on ultrasonic propagation paths, etc.

The size of a treating region is calculated by the therapeutic effect estimation section 61 on the basis of a plurality of parameters including the intensity of echo components from the diseased part, the ultrasonic absorption factor and the thermal conductivity of the diseased part, the attenuation factor of ultrasonic waves at the diseased part, the presence of an important organ or bone on the propagation paths, the application intensity, and the application time. Instead of this calculation, data indicative of the sizes of treating regions each of which corresponds to a respective one of various combinations of those parameters may be stored in the memory 45. The data is read from the memory by the system controller when necessary.

The amount of shift of a treating region (i.e., a region to be treated) from the focus to the side of the applicator 1 is calculated by the therapeutic effect estimation section 61 on the basis of a plurality of parameters of the intensity of echo components from the diseased part, the ultrasonic absorption factor and the thermal conductivity of the diseased part, the attenuation factor of ultrasonic waves at the diseased part, the presence of an important organ or bone on the propagation paths, the application intensity, and the application time. Instead of this calculation, data indicative of the amounts of shift of treating regions each of which corresponds to a respective one of various combinations of those parameters may be stored in the memory 45. The data is read from the memory by the system controller when necessary.

The therapeutic effect estimation section 61 causes the display section 54 to display a treating region indicating marker in the determined size and in the determined position. In FIG. 47, there is shown an example of a display image on the CRT in the display section 54.

It is evident that the display of a treating region estimated on the basis of the intensity distribution is more useful to sure treatment than the focus 8 of therapeutic ultrasonic waves is displayed as it is. As a result of an experiment under the conditions that a therapeutic ultrasonic transducer is used that consists of a single piezoelectric element of 110 mm in aperture diameter, 42 mm in diameter of interal hole, 100 mm in radius of curvature and 1.65 MHz in resonance frequency, and the applied electric energy to that transducer is 400W, and the application time is 10 sec., it has become evident that a treating region is shifted relative to the focus by about 2 mm toward the ultrasonic transducer. Under such parameters, the treating region indicating marker is displayed shifted by 2 mm from the focus 8 obtained in the intensity distribution imaging to the side of the applicator 1.

The marker may be displayed in a specific color or displayed in a light color or by half-tone dot meshing so that the B-mode image will not disappear. Alternatively, the treating region may be displayed by its contour only or by contour lines to fit the intensity distribution. A simpler geometric shape such as a cross or rectangle may be used for the marker. In this case, the size of the graphic form may be made to correspond to the size of a planned region for treatment. At this point, the actual focus of therapeutic ultrasonic waves may be displayed simultaneously. Further, the planned intensity and planned application time of ultrasonic waves may be displayed. If the peak intensity of echoes from the focus 8 obtained in the intensity distribution imaging is displayed in real time (numerical display, color bar display, or A-mode display), then the operator will be allowed to easily find the state in which the peak intensity becomes maximal while adjusting the coupling state, the tilt angle of the applicator, and the direction of approach. In that state, the efficiency of application of energy to the focus is highest, i.e., the most efficient ultrasonic application condition is achieved.

Next, a determination is made if the diseased part is larger than the focus 8 can be treated in its entirety while the focus is shifted little by little. The shift of the focus can be made electronically, or mechanically, or in combination. The pitch of shift is specified by the operator or calculated by the computation unit 440. The focus may be shifted to each adjacent region in sequence or on a diagonal line so as to suppress the effect of cavitation.

In either case, by setting the adjacent focus points so that treating regions corresponding to the foci of individual ultrasonic waves overlap ultimately, it becomes possible to necrotize all tumor cells. However, this will not apply to the case where the strong ultrasonic therapy is combined with another therapy. For example, there is a case where the edge of a tumor is cauterized by the present method and its center is treated by another method. A temperature rise in the treating region may be calculated from all energy applied, the heat diffused and cooling achieved by the blood flow, and the focus points may then be spaced at appropriate intervals determined from the temperature rise thus obtained.

In either case, by performing imaging of the intensity distribution within the diseased part according to the procedure of therapy prior to actual therapy and displaying individual predicted treating regions collectively, the ultimate treating region can be determined easily. FIG. 47 shows the case where the ultimate treating region is displayed half-tone dot meshed. This allows the presence or absence of an untreated region to be determined easily. The coupling state of the applicator 1 and the living body, the presence or absence of a strong reflector or absorber on the propagation paths of ultrasonic waves and whether the sufficient ultrasonic energy is applied to the focus 8 can be predicted by intensity distribution imaging in each focus position, improving the safety and reliability of therapy. The display of a treating region is performed for each of images of different planes as shown in FIG. 47. The operator can thus understand a predicted treating region three-dimensionally. These images may be displayed in sequence or in the form of a three-dimensionally constructed image.

When the conditions are recognized as being unsuitable for therapy, the operator can be notified of it with display or beep. In a more advanced way, the apparatus can be locked not to enter the therapy mode.

In the above, the intensity distribution imaging is performed with each scan by focus scanning of the diseased part 7 in its entirety prior to therapy and the resulting data such as application parameters are recorded and then read at the time of actual therapy. Alternatively, as a straightforward method, representative data that is obtained by intensity distribution imaging when the center of the focus 8 is made coincident with the center of the diseased part 7 may be used to determine the application parameters. In addition, it is also possible to perform intensity distribution imaging during actual therapy, that is, immediately before application of ultrasonic waves to each focus and determine the ultrasonic application conditions from the resulting data.

Next, the correction of spatial distortion of the intensity distribution obtained by the intensity distribution imaging by the distribution correction section 62 will be described. By causing both the therapeutic ultrasonic transducer 2 and the imaging probe 17 to emit ultrasonic pulses and the imaging probe 16 to receive echoes returned from within a living body under examination, a B-mode image and intensity distribution are acquired simultaneously. The timing of emitting of the ultrasonic pulses is selected such that the ultrasonic pulse from the transducer 2 and the ultrasonic pulse from the probe 16 will arrive at the center of the focus 8 at the same time.

As shown schematically in FIG. 48, the difference between the distance A over which the imaging ultrasonic waves travel from the probe 16 to a point P of reflection and from that point to the probe and the distance B over which the therapeutic ultrasonic waves travel from the transducer 2 to the point P and from that point to the transducer becomes greater as the point P goes farther away from the focus 8. In the ultrasonic diagnostic, since the depth is recognized by associating an axis in the direction of depth with the time axis of a received signal, the intensity distribution is distorted. For example, in FIG. 48, the point P is recognized on the intensity distribution as being a point P' that is nearer to the probe than that point P is. This amount of displacement is calculated by the system controller 9 or the computation unit 44 on the basis of the velocity of sound and the propagation path.

The intensity distribution is shifted in position by a correction value corresponding to that amount of displacement and then combined with a B-mode image. The amount of displacement is a function of spatial position. Thus, the substitution of position and sound velocity into the function will allow the amount of distortion to be calculated immediately. With the velocity of sound regarded as constant as in general ultrasonic diagnostic apparatus, the amounts of correction corresponding to the respective spatial positions could be recorded in the memory 45 to speed up the correction for each position. In addition to the method for making corrections in combining two types of images, there is a method for acquiring position data by splitting a signal by time gating and allowing for the amount of displacement in advance in acquiring position data in the direction of depth. In either case, except the case where echoes from the center of the focus are acquired, echoes used to reconstruct a B-mode image and echoes for reconstructing an intensity distribution image will represent data at different depths even if they are obtained in the same time gate.

Fourteenth Embodiment

FIG. 49 shows an arrangement of an ultrasonic therapeutic apparatus according to a forty-third embodiment of the invention. In this figure, like reference numerals are used to denote corresponding parts to those in FIGS. 1, 6, 37, and 46 and description thereof is omitted. In this embodiment, the distortion of the intensity distribution is corrected by adjusting the timing of ultrasonic pulses for imaging intensity distribution. A distribution correction section 62 is connected to a timing signal generator 180.

Figure 50A:
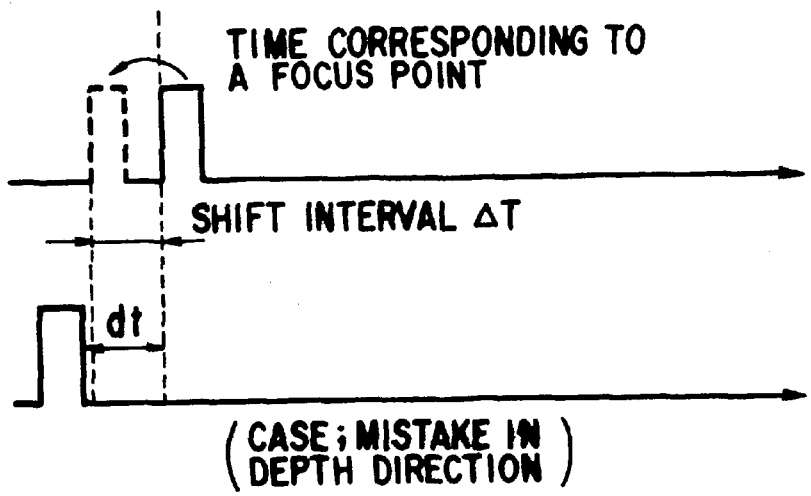
FIGS. 50A and 50B are diagrams for use in explanation of adjustment of the timing of ultrasonic waves for intensity distribution and the timing of ultrasonic waves for imaging.
Figure 50B:
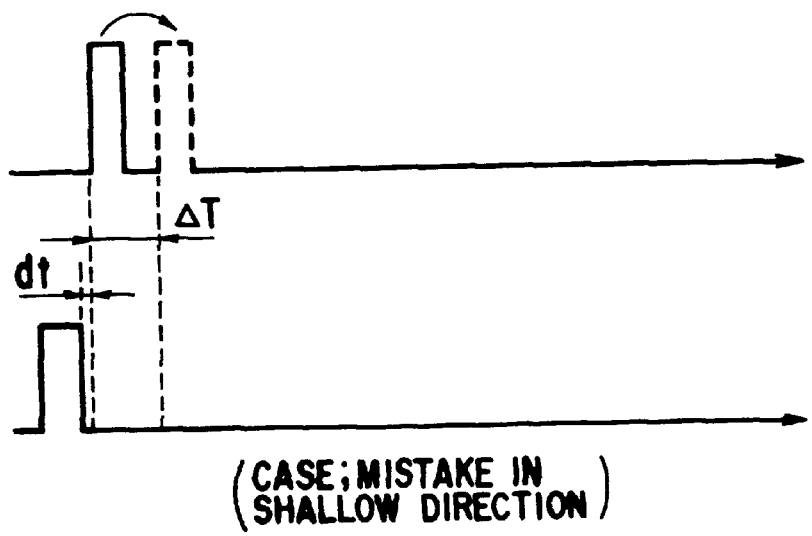

The applicator 1 is constructed from the therapeutic ultrasonic transducer 1 placed on a concave plane having a hole in its center and the imaging probe 16. Such a construction allows the focus region to be formed in a three-dimensional form that would be obtained by rotating the character "X" about its center line. In this case, a distribution form with no practical problem can be obtained by making positional corrections taking into consideration only points where ultrasonic waves are strong even if the spatial distortion at points where the ultrasonic waves are weak is sacrificed. That is, the distortion is corrected with each point on the character "X" being allowed for. To this end, as shown in FIGS. 50A and 50B, the amount of correction is converted from the dimension of distance to the dimension of time and the timing of ultrasonic pulses for imaging intensity distribution from the therapeutic ultrasonic transducer 2 is changed by ΔT. More specifically, the amount of positional displacement at the point of maximum intensity on the character "X" is divided by the sound velocity with each raster scan. The timing of intensity distribution imaging ultrasonic pulses is changed from the timing for the focus position by the result of the division, ΔT. When, in this case, there are multiple points on the "X" for some raster, the point closest to the focus is selected as the criterion.

A simulation (focus shift and intensity distribution imaging) immediately prior to therapy is carried out using the present method and then actual thermotherapy is initiated. At the time of therapy, ultrasonic bursts whose energy is high enough to thermally metamorphose and necrotize tissues in less than one second are applied as therapeutic ultrasonic waves. A that point, the therapy is carried out in accordance with the contents of the above-described therapeutic simulation, whereby safe and reliable therapy is realized.

That is, the parameters of the pitch of the focus shift, the application intensity, the application time, etc., are set as in the therapeutic simulation. In the application sequence of ultrasonic waves in the therapy mode, the focus shift, the intensity distribution imaging, the application of therapeutlc ultrasonic waves, the intensity distribution imaging, the focus shift, etc., are performed in this order. Besides this sequence, there are various combinations of the intensity distribution imaging and the application of therapeutic ultrasonic waves. For example, the intensity distribution imaging may be performed only after the application of therapeutic ultrasonic waves. Or the intensity distribution imaging may be performed each time the application of the therapeutic ultrasonic waves is performed a previously set number of times. The operator is allowed to select among the combination patterns according to the situation. The case where the intensity distribution imaging is performed before and after the application of the therapeutic ultrasonic waves will be described herein.

First, the focus shift is performed to fit a treating region to the target position. Next, the intensity distribution is performed with reference to the application conditions determined by the simulation. After reconfirmation that sufficient energy has been applied to the focus and no strong reflector or absorber is present on the propagation paths of therapeutic ultrasonic waves, the process goes to the application of therapeutic ultrasonic waves. In this case, the application of therapeutic ultrasonic waves according to the cavitation suppressing application method as disclosed in Japanese Patent application No. 6-248480 could provide a reliable therapeutic result (thermally metamorphosed region). After the application of therapeutic ultrasonic waves, the intensity distribution imaging is performed again, which allows a determination of whether a thermally metamorphosed region has been obtained.

That is, since the thermally metamorphosed region is greatly different in acoustic characteristics from unmetamorphosed regions, strong echoes are obtained at the interface between the thermally metamorphosed region and unmetamorphosed regions. Thus, a treated region (i.e., a region already treated) can be detected by receiving and analyzing such echoes. To this end, echoes from the same position are compared before and after therapy. A region which makes a great difference can be regarded as a treated region. In a more general way, the A mode may be used to determine whether the therapy has been provided reliably. Alternatively, the difference in brightness between B-mode images before and after therapy may be detected to find a treated region.

As described above, since the safety of the propagation paths of ultrasonic waves and the application conditions of energy to the focus 8 can be checked again prior to the application of therapeutic ultrasonic waves and a determination of whether the therapy has been achieved reliably can be made by using the intensity distribution after the application of therapeutic ultrasonic waves, the safety and reliability of therapy can be improved. This work can be done in a short time because it involves only analysis of echo data obtained by intensity distribution imaging that is performed for each individual focus position. Next, the focus 8 is shifted to the next treating region in accordance with the focus scan sequence previously set and then the same operation as above is repeated for the next therapy. If treated regions are stored and colored differently at the time of display so that they can be visually recognized immediately, then a determination of whether the entire diseased part has been subjected to therapy can be made at a glance.

At the time of therapy, patient's movement may cause a serious problem. The movement of the patient in the middle of therapy will make unclear the positional relationship among the diseased part 7, treated regions, and the focus 8. This will make it impossible to proceed with the therapy as planned. In such case, there are the following countermeasures: the therapeutic plan is changed to restart the therapy from the beginning; a new therapeutic plan for the remaining region is made to restart the therapy; and return is made to the original state. The first approach is most convenient but it increases the time required for therapy. The second or third approach requires treated regions to be specified. The suitable method therefor would be to detect reflected ultrasonic waves from the boundaries of treated regions. To this end, the intensity distribution imaging can be used. In this case, the use of the body surface as the reference point permits a treated region to be specified even if the patient moves.

To be specific, the timing of receiving of echoes from the body surface of the patient 6 or the water bag 4 and the timing of receiving of echoes from a treated region (i.e., a region already treated) are measured in advance in the intensity distribution imaging immediately after the application of therapeutic ultrasonic waves. Since there is a propagation medium 5 just in front of the body surface or the water bag, the body surface or the water bag can easily be detected. Immediately after therapy the echoes from the boundary of a treated region have a great amplitude in comparison with those immediately before therapy. Thus, the detection of the timing of receiving of echoes from a treated region is easy. The relationship between the body surface or water bag and the boundary of a treated region with respect to time allows the treated region to be easily detected again even if the patient moves. To specify the treated region, B-mode brightness information and the previous data including RF data) may be employed. The movement of the patient can be detected by movement detecting means such as an optical supervisory camera, resistance-change detecting method using and elastic resistor wrapped around the patient, photoelectric pulsation method, or the like.

Figure 51:
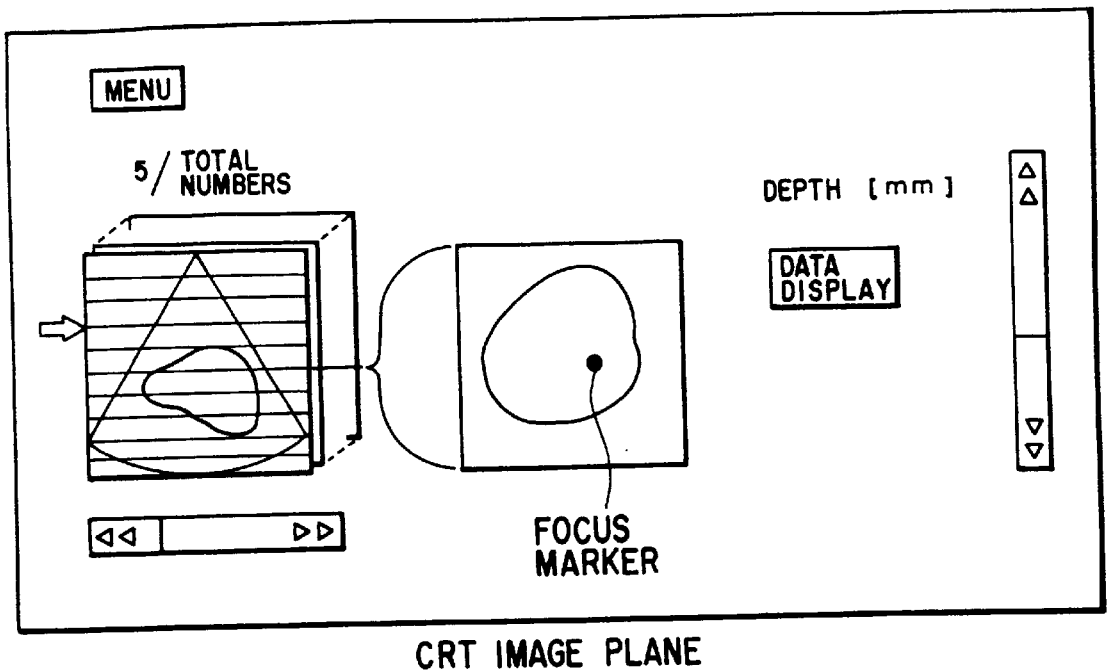
FIG. 51 shows another example of a display image on the display unit of FIG. 46.

Next, a method of display will be described with reference to FIG. 51 illustrating an example of a display image. With therapy based on strong ultrasonic waves, it is desirable to cauterize tissues in sequence from the point farthest from the therapeutic ultrasonic transducer 2, i.e., from the bottom surface of a volume to be treated, as disclosed in Japanese Patent Application No. 6-246843. The reason is that when the acoustic characteristics of a tissue vary due to thermal metamorphosis, ultrasonic waves reflect from its boundary, and the thermally metamorphosed region absorbs the energy. Hence the energy of ultrasonic waves becomes difficult to reach regions behind the thermally metamorphosed region. Since a plane that undergoes treatment intersects a two-dimensional B-mode tomogram in this method, it is difficult to take it as an image for treatment.

To solve the difficulty, a B-mode image corresponding to a plane to which treatment is provided actually is reconstructed from a plurality of B-mode images for different sectional planes and displayed.

The positional relationship between the probe 16 and the display image is displayed. The B-mode images have been acquired during the simulation prior to therapy with the focus 8 shifted in sequence.

Figure 52:
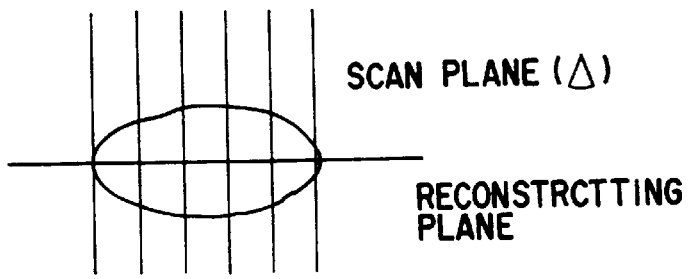
FIG. 52 is a diagram for use in explanation of the reconstruction of an image of a plane orthogonal to an imaging scan plane.

FIG. 52 shows a plurality of scan planes. B-mode image data has been acquired for all the scan planes. The data corresponds to a cluster of two-dimensional images. An image has one-dimensional image information at a constant depth. Extraction of the one-dimensional image information from each image of data permits a B-mode image at a depth of interest to be reconstructed. At the time of therapy based on that C-mode image, markers representing the focus 8 and a region to be treated are displayed on that image. In this case, the focus marker is displayed in the form of a circle, a dot, a cross, or the like.

A sector type of imaging probe is used herein. This probe may be replaced by a convex-type one. With this type of probe, at a point an imaging region is displayed narrower than at another point that is farther from the probe. In other words, the width of an ultrasonic image varies with depth. In order to obtain an ultrasonic image the width of which is not dependent on the depth, therefore, it is preferable to use a linear type of imaging probe (either mechanical scan type or electronic scan type). Alternatively, a three-dimensional ultrasonic image may be reconstructed to reconstruct a false translucent image. In this case, a plane or volume which corresponds to a plane or volume that is treated by one-time application of ultrasonic waves may be colored with a light color or may be enclosed by a line to thereby emphasize a plane or volume of interest.

As an example, specifying a treating region with reference to a B-mode image will be described next. A plurality of B-mode images are acquired to include the entire region of a diseased part 7 for which therapy is planned. At this point, the operator specifies a treating region on each of the B-mode images using a light pen, a mouse, a joystick, or a trackball. The application of therapeutic ultrasonic waves on the basis of the treating regions thus specified allows reliable therapy to be achieved up to details of the boundary surface of the application region. Here, a three-dimensional image may be constructed from the B-mode images. Instead of using ultrasonic images to specify treating regions, X-ray CT or MRI may be used.

Next, a method of depicting accurately the focus in the actual focus position will be described. As described previously, at the time of intensity distribution imaging, in vivo imaging ultrasonic pulses are synchronized with intensity distribution imaging ultrasonic pulses so that an imaging ultrasonic pulse is emitted from the imaging probe at the instant the wave front indicating the peak intensity of an intensity distribution imaging ultrasonic pulse passes the probe. The accuracy of the synchronization determines the accuracy of the position of the focus to be depicted in the intensity distribution imaging. Here, an ultrasonic probe is provided to pick up the intensity distribution imaging ultrasonic pulses. The probe may be arranged in the same plane as the imaging probe 16, or may be adjusted in its characteristics so that it may function in the same way as it located in that plane. Alternatively, the imaging probe 16 is used as a pickup probe. If the timing of the intensity distribution imaging ultrasonic pulses from the therapeutic ultrasonic transducer is determined by feedback control of the intensity distribution ultrasonic pulses that are actually picked up, the focus position can be depicted with very high precision.

Next, a method of quantifying the intensity of echoes received during intensity distribution imaging will be described. The deeper an ultrasonic wave propagates within a living body, the more it attenuates. Likewise, the deeper the reflective point of an ultrasonic wave is, the lower its intensity when it emerges from the body surface becomes due to the energy loss in propagation. It is therefore preferable to weight the intensity of echoes received by the imaging probe 16 according to the depth from the body surface to display the intensity distribution. For example, at the time of B-mode image reconstruction, the amplification factor is generally increased according to the depth.

It is also possible to display patient information on the CRT. In this case, it is convenient to display information on a treating region, its position information and the size, the history of the power and time of applied ultrasonic waves obtained so far according to the present method. The information may be updated each time new treatment is provided. The information can be connected to the therapy plan making apparatus on-line or through a recording medium, helping to make a plan for therapy.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic therapeutic apparatus comprising:

a source of therapeutic ultrasonic waves;

an ultrasonic probe;

means for driving said source of therapeutic ultrasonic waves;

means for driving said ultrasonic probe to generate imaging ultrasonic waves;

receiving means for receiving echoes of first ultrasonic waves generated by said therapeutic ultrasonic wave generating source and echoes of second ultrasonic waves generated by said ultrasonic probe through said ultrasonic probe;

first filtering means for extracting a first component within a first specific band corresponding to the fundamental frequency of said first ultrasonic waves from an output of said receiving means;

second filtering means for extracting a second component within a specific band corresponding to the fundamental frequency of said second ultrasonic waves from said output of said receiving means;

means for amplifying each of said first and second components individually; and means for forming an image on the basis of said first and second components amplified by said amplifying means.

2. An ultrasonic therapeutic apparatus comprising:

a source of therapeutic ultrasonic waves;

an ultrasonic probe;

drive means for driving said source of therapeutic ultrasonic waves to generate ultrasonic waves that converge onto a focus;

drive means for driving said ultrasonic probe to generate in vivo imaging ultrasonic waves;

constructing means for constructing the intensity distribution of said ultrasonic waves and a tomographic image of a subject on the basis of echoes of said ultrasonic waves from said source and echoes of said imaging ultrasonic waves from said ultrasonic probe received through said ultrasonic probe; and means for detecting a focal region of therapeutic ultrasonic waves on the basis of said intensity distribution;

means for forming the focus of therapeutic ultrasonic waves in a first focal position and a second focal position; and means for displaying a combined region of a first focal region corresponding to said first focal position and a second focal region corresponding to said second focal position on the tomographic image.

* * * * *